(12) United States Patent
Berkowitz et al.

(10) Patent No.: US 8,859,614 B2
(45) Date of Patent: Oct. 14, 2014

(54) ANALOGUES OF (−)-PICROPODOPHYLLIN, SYNTHESIS AND USES THEREOF

(75) Inventors: David B. Berkowitz, Lincoln, NE (US); Sylvain Broussy, Lincoln, NE (US)

(73) Assignee: University of Nebraska—Lincoln, Lincoln, NE (US)

( * ) Notice: Subject to any disclaimer, the term of this patent is extended or adjusted under 35 U.S.C. 154(b) by 736 days.

(21) Appl. No.: 12/367,946

(22) Filed: Feb. 9, 2009

(65) Prior Publication Data

US 2009/0271879 A1     Oct. 29, 2009

Related U.S. Application Data

(63) Continuation of application No. PCT/US2009/033416, filed on Feb. 6, 2009.

(60) Provisional application No. 61/027,459, filed on Feb. 9, 2008, provisional application No. 61/122,945, filed on Dec. 16, 2008.

(51) Int. Cl.
*A61K 31/357*     (2006.01)
*C07D 317/70*     (2006.01)
*C07D 493/04*     (2006.01)

(52) U.S. Cl.
CPC ............ *C07D 493/04* (2013.01); *C07D 317/70* (2013.01); *A61K 31/357* (2013.01)
USPC .......................................... 514/463; 549/432

(58) Field of Classification Search
CPC .............................. A61K 31/357; C07D 317/70
USPC ...................... 549/298, 457, 432; 514/463
See application file for complete search history.

(56) References Cited

U.S. PATENT DOCUMENTS

| | | | |
|---|---|---|---|
| 4,122,092 | A | 10/1978 | Kende et al. |
| 4,294,763 | A | 10/1981 | Kende et al. |
| 5,739,114 | A | 4/1998 | Gordaliza et al. |
| 7,629,381 | B2 | 12/2009 | Larsson et al. |
| 7,662,851 | B2 | 2/2010 | Larsson et al. |
| 7,709,526 | B2 | 5/2010 | Larsson et al. |
| 2004/0167208 | A1 | 8/2004 | Larsson et al. |
| 2004/0186169 | A1 | 9/2004 | Larsson et al. |
| 2007/0123491 | A1 | 5/2007 | Axelson et al. |
| 2009/0326248 | A1 | 12/2009 | Larsson et al. |
| 2010/0216728 | A1 | 8/2010 | Larsson et al. |
| 2010/0227797 | A1 | 9/2010 | Axelson et al. |
| 2011/0178050 | A1 | 7/2011 | Axelson et al. |

FOREIGN PATENT DOCUMENTS

| WO | WO 02/102805 | 12/2002 |
|---|---|---|
| WO | WO 2004/054996 | 7/2004 |
| WO | WO 2004/055022 | 7/2004 |
| WO | WO 2004/093781 | 11/2004 |

OTHER PUBLICATIONS

Liu, Micellar electrokinetic capillary chromatographic separation of diastereoisomers of podophyllum lignans at the C4 position, 2002, Chromatgraphia, vol. 56, No. 11/12, p. 687-691.*
Liu, STN Record of journal article—Micellar electrokinetic capillary chromatographic separation of diastereoisomers of podophyllum lignans at the C4 position found in Chromatgraphia, CA Plus DN 139:185779, entry date: Jan. 7, 2003; Citied compounds, entry date: Sep. 5, 2003.*
ASO, 1989, Chem. Pharm. Bull, vol. 37, No. 2, p. 422-424.*
Asselin-Labat ML, et al., "Steroid hormone receptor status of mouse mammary stem cells," *J Natl Cancer Inst.* (2006); 98(14):1011-4.
Asselin-Labat ML, et al., "Gata-3 is an essential regulator of mammary-gland morphogenesis and luminal-cell differentiation," *Nat Cell Biol.* (2007); 9(2):201-9.
Baserga R, "The insulin-like growth factor-I receptor as a target for cancer therapy," *Expert Opin Ther Targets.* (2005); 9(4):753-68.
Blum G, et al., "Development of new insulin-like growth factor-1 receptor kinase inhibitors using catechol mimics," *J Biol Chem.* (2003); 278(42):40442-54.
Booth BW, et al., "Alveolar progenitor cells develop in mouse mammary glands independent of pregnancy and lactation," *J Cell Physiol.* (2007); 212(3):729-36.
Cardiff RD, et al., The mouse in Medical Research (2007), vol. II: *Diseases*, Second edt., eds. Fox JG et al., (Elsevier, New York), pp. 581-622.
Carey LA, et al., "The triple negative paradox: primary tumor chemosensitivity of breast cancer subtypes," *Clin Cancer Res.* (2007); 13(8):2329-34.
Charafe-Jauffret E, et al., "Gene expression profiling of breast cell lines identifies potential new basal markers," *Oncogene.* (2006); 25(15):2273-84.
Chen YF, et al., "Detection of circulating cancer cells with K-ras oncogene using membrane array," Cancer Lett. 2005; 229(1):115-22.
Chin K, et al., "Genomic and transcriptional aberrations linked to breast cancer pathophysiologies," *Cancer Cell* (2006); 10(6):529-41.
Chong YM, et al., "Insulin-like growth factor 1 (IGF-1) and its receptor mRNA levels in breast cancer and adjacent non-neoplastic tissue," *Anticancer Res.* (2006); 26(1A):167-73.
Clark GJ and Der CJ, "Aberrant function of the Ras signal transduction pathway in human breast cancer," *Breast Cancer Res Treat.* (1995); 35(1):133-44.
Cleator S, et al., "Triple-negative breast cancer: therapeutic options," *Lancet Oncol.* (2007); 8(3):235-44.
Cristofanelli B, et al., "Cooperative transformation of 32D cells by the combined expression of IRS-1 and V-Ha-Ras," *Oncogene.* (2000); 19(29):3245-55.
D'Ambrosio C, et al., "A soluble insulin-like growth factor I receptor that induces apoptosis of tumor cells in vivo and inhibits tumorigenesis," *Cancer Res.* (1996); 56(17):4013-20.
Da Silva L, et al., "Demystifying basal-like breast carcinomas," *J Clin Pathol.* (2007); 60(12):1328-32.

(Continued)

*Primary Examiner* — Rebecca Anderson
*Assistant Examiner* — Karen Cheng
(74) *Attorney, Agent, or Firm* — Banner & Witcoff, Ltd.

(57) ABSTRACT

Analogs of (−)-Picropodophyllin, synthesis thereof, and uses in pharmaceuticals as inhibitors of IGF1RK.

10 Claims, 10 Drawing Sheets

(56) References Cited

OTHER PUBLICATIONS

Figure 5A:
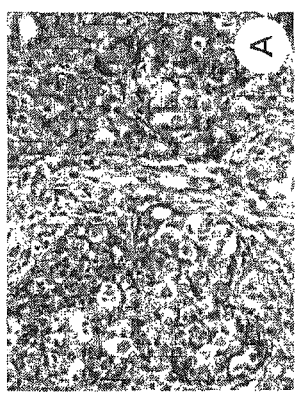
Figure 5B:
Figure 5C:
Figure 5D:
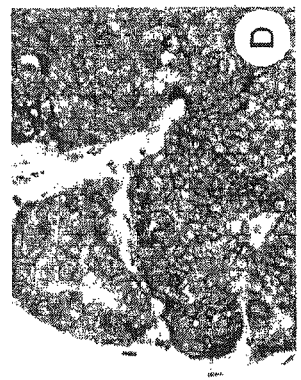

Dati C, et al., "c-erbB-2 and ras expression levels in breast cancer are correlated and show a co-operative association with unfavorable clinical outcome," *Int J Cancer*. (1991); 1; 47(6):833-8.

Dunn SE, et al., "Insulin-like Growth Factor 1 (IGF-1) Alters Drug Sensitivity of HBL100 Human Breast Cancer Cells by Inhibition of Apoptosis Induced by Diverse Anticancer Drugs," *Cancer Res* 1997 57: 2687-2693.

Efstratiadis A, "Genetics of mouse growth," *Int J Dev Biol*. (1998); 42(7):955-76.

Farmer P, et al., "Identification of molecular apocrine breast tumours by microarray analysis," *Oncogene*. (2005); 24(29):4660-71.

Finnegan TJ and Carey LA, "Gene-expression analysis and the basal-like breast cancer subtype," *Future Oncol*. 2007; 3(1):55-63.

García-Echeverría C, et al, "In vivo antitumor activity of NVP-AEW541-A novel, potent, and selective inhibitor of the IGF-IR kinase," *Cancer Cell*. (2004); 5(3):231-9.

Garcia-Echeverria C, "Medicinal chemistry approaches to target the kinase activity of IGF-1R," *IDrugs*. (2006); 9(6):415-9.

Girnita A, et al., "Cyclolignans as inhibitors of the insulin-like growth factor-1 receptor and malignant cell growth," *Cancer Res*. (2004); 64(1):236-42.

Girnita A, et al., "The insulin-like growth factor-I receptor inhibitor picropodophyllin causes tumor regression and attenuates mechanisms involved in invasion of uveal melanoma cells," Clin Cancer Res. (2006); 12(4):1383-91.

Gray SG, et al., "The insulin-like growth factors and insulin-signalling systems: an appealing target for breast cancer therapy?" *Horm Metab Res*. (2003); 35(11-12):857-71.

Gupta S, et al., "Binding of ras to phosphoinositide 3-kinase p110alpha is required for ras-driven tumorigenesis in mice," *Cell*. (2007); 129(5):957-68.

Hartog H, et al., The insulin-like growth factor 1 receptor in cancer: old focus, new future, *Eur J Cancer*. (2007); 43(13):1895-904.

Herschkowitz JI, et al., "Identification of conserved gene expression features between murine mammary carcinoma models and human breast tumors," *Genome Biol*. (2007); 8(5):R76.

Hoffman et al., "In vitro and in vivo profiling of selective and potent IGF-IR kinase inhibitors," *AACR* Annual Meeting (2003), Abstract #3798.

Hollestelle A, et al., "Phosphatidylinositol-3-OH kinase or RAS pathway mutations in human breast cancer cell lines," *Mol Cancer Res*. (2007); 5(2):195-201.

Hubbard RD and Wilsbacher JL, "Advances towards the development of ATP-competitive small-molecule inhibitors of the insulin-like growth factor receptor (IGF-IR)," *ChemMedChem*. (2007); 2(1):41-6.

Kozma SC, et al., "The human c-Kirsten ras gene is activated by a novel mutation in codon 13 in the breast carcinoma cell line MDA-MB231," *Nucleic Acids Res*. (1987); 15(15):5963-71.

Lerma E, et al., "Immunohistochemical heterogeneity of breast carcinomas negative for estrogen receptors, progesterone receptors and Her2/neu (basal-like breast carcinomas)," *Mod Pathol*. (2007); 20(11):1200-7.

Li Y, et al., "Evidence that transgenes encoding components of the Wnt signaling pathway preferentially induce mammary cancers from progenitor cells," *Proc Natl Acad Sci U S A*. (2003); 100(26):15853-8.

Macaulay VM, et al., "Downregulation of the type 1 insulin-like growth factor receptor in mouse melanoma cells is associated with enhanced radiosensitivity and impaired activation of Atm kinase," *Oncogene*. (2001); 20(30):4029-40.

Malaney S and Daly RJ, "The ras signaling pathway in mammary tumorigenesis and metastasis," *J Mammary Gland Biol Neoplasia*. (2001); 6(1):101-13.

Matulka LA, et al., "Parity-induced mammary epithelial cells are multipotent and express cell surface markers associated with stem cells," *Dev Biol*. (2007); 303(1):29-44.

Menu E, et al., "Targeting the IGF-1R using picropodophyllin in the therapeutical 5T2MM mouse model of multiple myeloma: beneficial effects on tumor growth, angiogenesis, bone disease and survival," *Int J Cancer*. (2007); 121(8):1857-61.

Miyakis S, et al., "Differential expression and mutation of the ras family genes in human breast cancer," *Biochem Biophys Res Commun*. 1998; 251(2):609-12.

Nielsen TO, et al., "Immunohistochemical and clinical characterization of the basal-like subtype of invasive breast carcinoma," *Clin Cancer Res*. (2004); 10(16):5367-74.

Ornskov D, et al., "Insulin induces a transcriptional activation of epiregulin, HB-EGF and amphiregulin, by a PI3K-dependent mechanism: identification of a specific insulin-responsive promoter element," *Biochem Biophys Res Commun*. (2007); 354(4):885-91.

Perou CM, et al., "Molecular portraits of human breast tumours," *Nature* (2000); 406(6797):747-52.

Pollak MN, et al., "Insulin-like growth factors and neoplasia," *Nat Rev Cancer*. (2004); 4(7):505-18.

Politi K, et al., "'Designer' tumors in mice," *Oncogene*. (2004); 23(8):1558-65.

Reis-Filho JS and Tutt AN, "Triple negative tumours: a critical review," *Histopathology*. (2008); 52(1):108-18.

Richardson AL, et al., "X chromosomal abnormalities in basal-like human breast cancer." *Cancer Cell*. (2006); 9(2):121-32.

Riedemann J, et al., "The EGF receptor interacts with the type 1 IGF receptor and regulates its stability," *Biochem Biophys Res Commun*. (2007); 355(3):707-14.

Ryan PD and Goss PE, "The emerging role of the insulin-like growth factor pathway as a therapeutic target in cancer," *Oncologist*. (2008); 13(1):16-24.

Sachdev D and Yee D, "Inhibitors of insulin-like growth factor signaling: a therapeutic approach for breast cancer," *J Mammary Gland Biol Neoplasia*. (2006); 11(1):27-39.

Sachdev D and Yee D, "Disrupting insulin-like growth factor signaling as a potential cancer therapy," *Mol Cancer Ther*. (2007); 6(1):1-12.

Sarkisian CJ, et al., "Dose-dependent oncogene-induced senescence in vivo and its evasion during mammary tumorigenesis," *Nat Cell Biol*. (2007); 9(5):493-505.

Sell C, et al., "Simian virus 40 large tumor antigen is unable to transform mouse embryonic fibroblasts lacking type 1 insulin-like growth factor receptor," *Proc Natl Acad Sci U S A*. (1993); 90(23):11217-21.

Sell C, et al., "Effect of a null mutation of the insulin-like growth factor I receptor gene on growth and transformation of mouse embryo fibroblasts," *Mol Cell Biol*. (1994); 14(6):3604-12.

Sørlie T, et al., "Gene expression patterns of breast carcinomas distinguish tumor subclasses with clinical implications," *Proc Natl Acad Sci U S A*. (2001); 98(19):10869-74.

Sørlie T, et al., "Repeated observation of breast tumor subtypes in independent gene expression data sets," *Proc Natl Acad Sci U S A*. (2003); 100(14):8418-23.

Sørlie T, et al., "Distinct molecular mechanisms underlying clinically relevant subtypes of breast cancer: gene expression analyses across three different platforms," *BMC Genomics*. (2006); 7:127.

Srinivas S, et al., "Cre reporter strains produced by targeted insertion of EYFP and ECFP into the ROSA26 locus," *BMC Dev Biol*. (2001); 1:4.

Stingl J et al., "Purification and unique properties of mammary epithelial stem cells," *Nature*. (2006); 439(7079):993-7.

Sweet-Cordero A et al., "An oncogenic KRAS2 expression signature identified by cross-species gene-expression analysis," *Nat Genet*. (2005); 37(1):48-55.

Vaillant F, et al., "The emerging picture of the mouse mammary stem cell," *Stem Cell Rev*. (2007); 3(2):114-23.

Vasilcanu R, et al., "Picropodophyllin induces downregulation of the insulin-like growth factor 1 receptor: potential mechanistic involvement of Mdm2 and beta-arrestin1," *Oncogene*. (2008); 27(11):1629-38.

Vitale-Cross L, et al., "Conditional expression of K-ras in an epithelial compartment that includes the stem cells is sufficient to promote squamous cell carcinogenesis," *Cancer Res*. (2004); 64(24):8804-7.

Von Lintig FC, et al., "Ras activation in human breast cancer," *Breast Cancer Res Treat*. (2000); 62(1):51-62.

(56) References Cited

OTHER PUBLICATIONS

Wagner KU, et al., "Cre-mediated gene deletion in the mammary gland," *Nucleic Acids Res.* (1997); 25(21):4323-30.

Warshamana-Greene GS, et al., "The insulin-like growth factor-I (IGF-I) receptor kinase inhibitor NVP-ADW742, in combination with STI571, delineates a spectrum of dependence of small cell lung cancer on IGF-I and stem cell factor signaling," *Mol Cancer Ther.* (2004); 3(5):527-35.

Warshamana-Greene GS, et al., "The insulin-like growth factor-I receptor kinase inhibitor, NVP-ADW742, sensitizes small cell lung cancer cell lines to the effects of chemotherapy," *Clin Cancer Res.* (2005); 11(4): 1563-71.

Welm BE, et al., "Sca-1(pos) cells in the mouse mammary gland represent an enriched progenitor cell population," *Dev Biol.* (2002); 245(1):42-56.

Wijnhoven SW, et al., "Mice expressing a mammary gland-specific R270H mutation in the p53 tumor suppressor gene mimic human breast cancer development," *Cancer Res.* (2005); 65(18):8166-73.

Xuan S, et al., "Defective insulin secretion in pancreatic beta cells lacking type 1 IGF receptor," *J Clin Invest.* (2002); 110(7):1011-9.

Yamamoto A, et al., "The ons and offs of inducible transgenic technology: a review," *Neurobiol Dis.* (2001); 8(6):923-32.

Yang SX, et al., "Gene expression patterns and profile changes pre- and post-erlotinib treatment in patients with metastatic breast cancer," *Clin Cancer Res.* (2005); 11(17):6226-32.

Yehiely F, et al., "Deconstructing the molecular portrait of basal-like breast cancer," *Trends Mol Med.* (2006); 12(11):537-44.

Gensler, et al.,"Compounds Related to Podophyllotoxin. X. Synthesis of Picropodophyllin," *J. Am. Chem. Soc.* (1960); 82: 1714-1727.

U.S. Appl. No. 12/851,287, filed Aug. 5, 2010, (Abandoned).

Maxime Vitale et al., JOC Article, New Picropodophyllin Analogs via Palladium-Catalyzed Allylic Alkylation-Hiyama Cross-Coupling Sequences, J. Org. Chem, vol. 73, pp. 5795-5805, dated Apr. 2, 2008.

Zhiping Che et al, Insight into dihalogenation of E-ring of podophyllotoxins, and their acyloxyation derivatives at the C4 position as insecticidal agents, Bioorganic & Medicinal Chemistry Letters, vol. 23, pp. 5592-5598, dated 2013.

Changqu Zhao et al, Two New Podophyllotoxin Glucosides from Sinopodophyllum emodi (WALL.) Ying, Chem. Pharm. Bull. vol. 49(6), pp. 773-775, dated 2001.

Eckart Eich et al, (–)-Arctigenin as a Lead Structure for Inhibitors of Human Immunodeficiency Virus Type-1 Integrase, J. Med. Chem. vol. 39, pp. 86-95, dated 1996.

David E. Jackson et al, Biosynthesis of Podophyllum Lignans-II. Interconversions of Aryltetralin Lignans in Podophyllum Hexandrum, Phytochemistry, vol. 23, No. 5, pp. 1037-1042, dated 1984.

Gerard W. M. Visser et al, Synthesis of 18 F-Labelled VP 16-213 and Podophyllotoxin Using Acetyl Hypofluorite, Appl. Radiat. Isot., vol. 40, No. 1, pp. 47-51, dated 1989.

\* cited by examiner

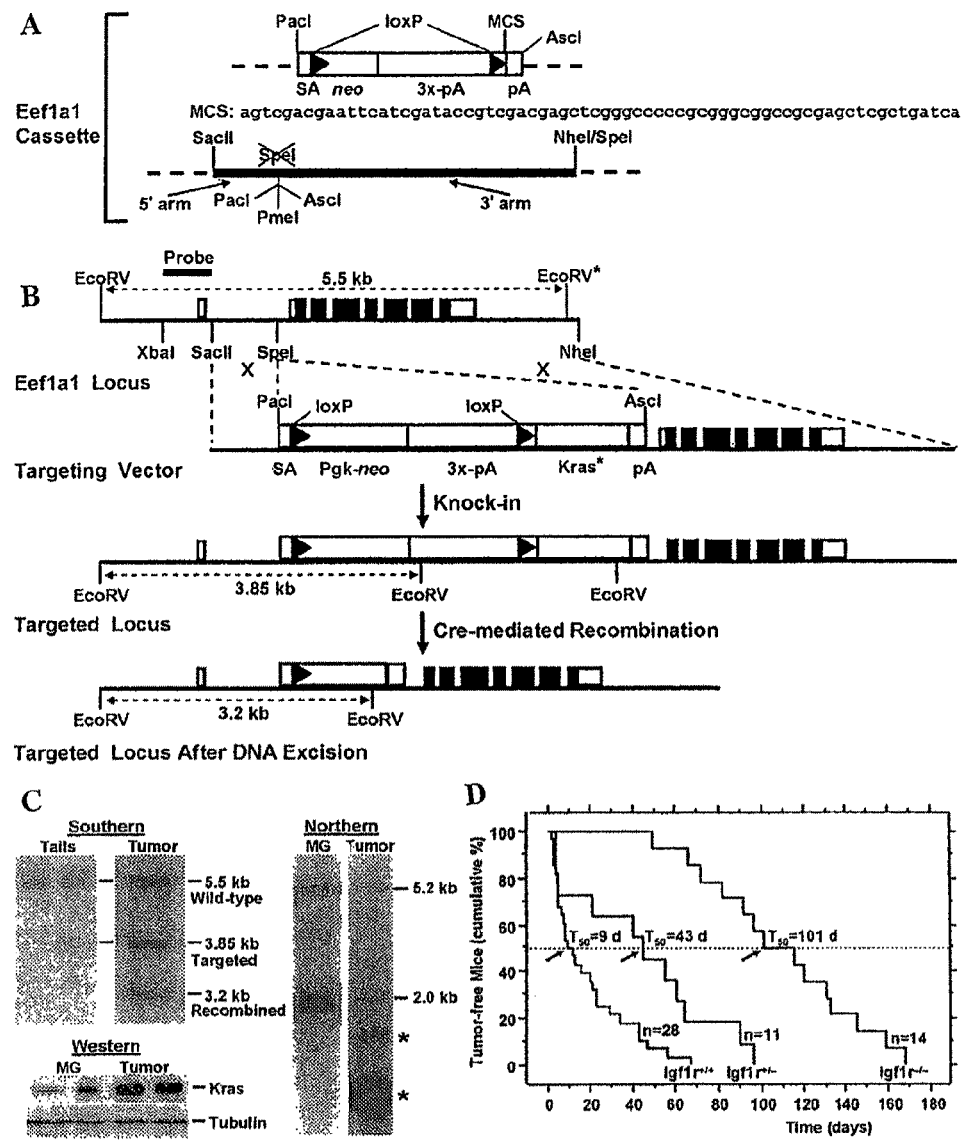
FIGURE 1A-D

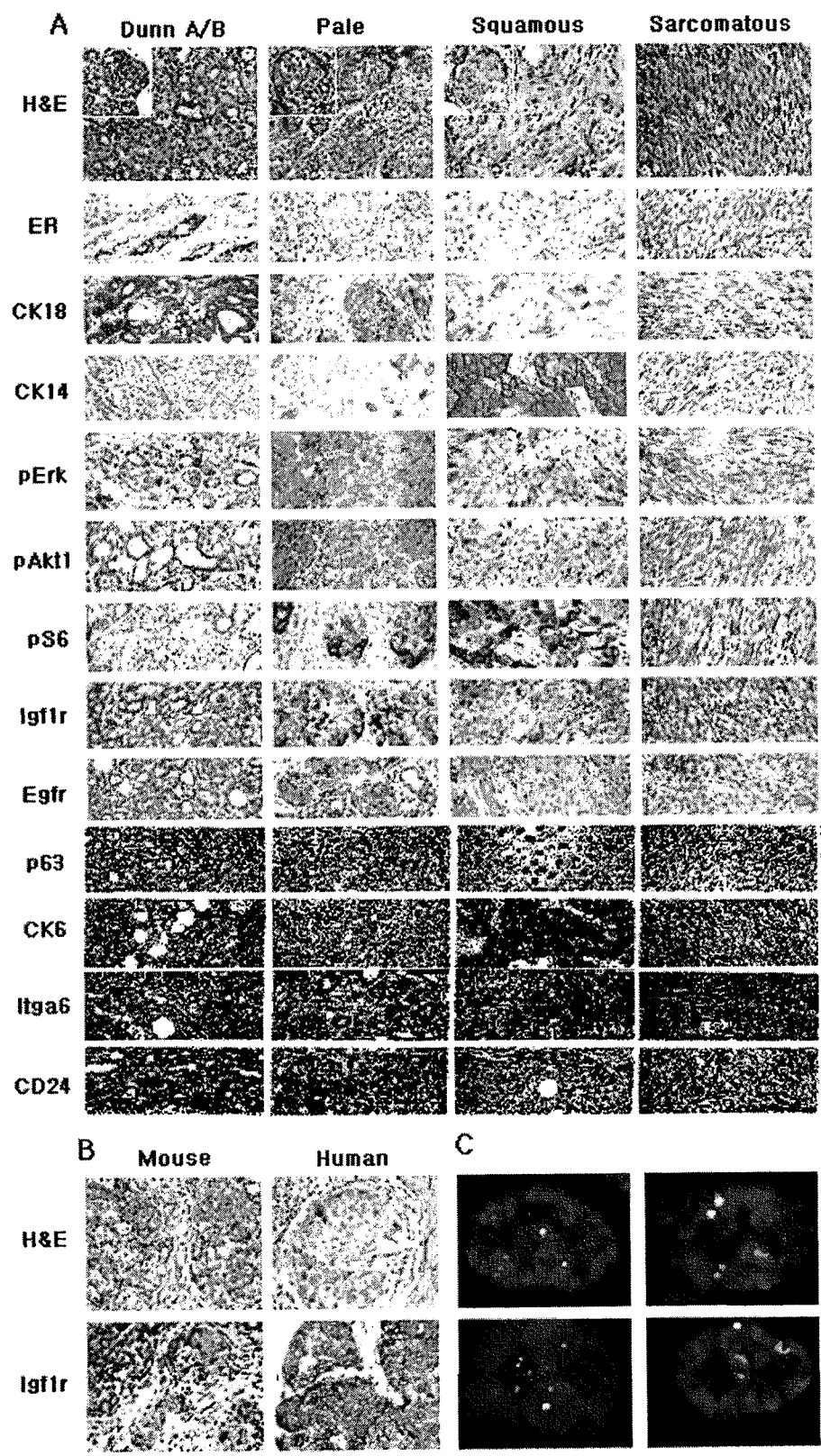
FIGURE 2A-C

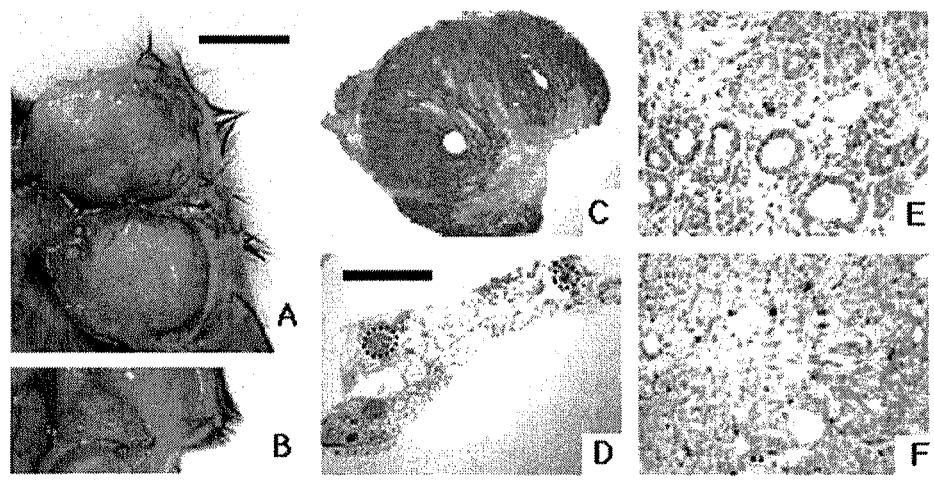
FIGURE 3A-F

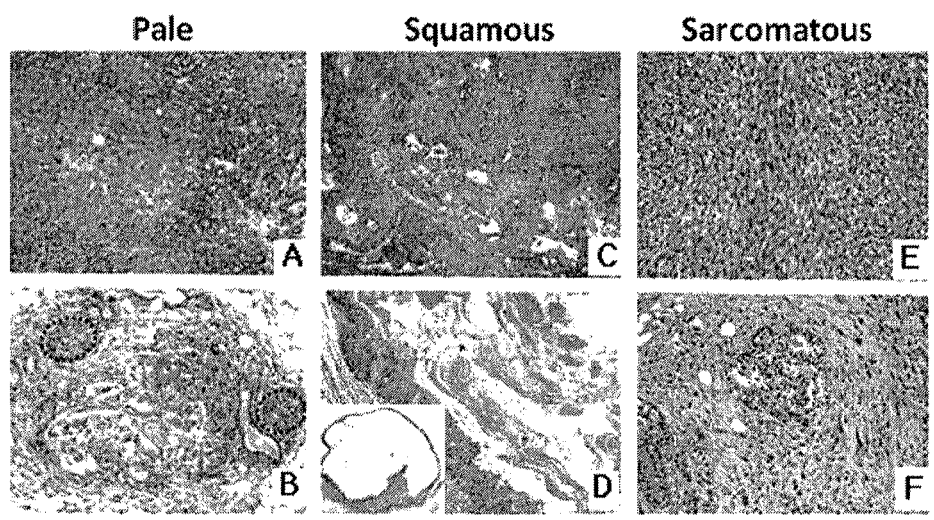
FIGURE 4A-F

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Combined DNA/RNA molecule: siRNA duplex R4
      sense strand
<220> FEATURE:
<223> OTHER INFORMATION: siRNA duplex R4 sense strand

<400> SEQUENCE: 1
caaugaguac aacuaccgct t                                                21

<210> SEQ ID NO 2
<211> LENGTH: 21
<212> TYPE: DNA
<213> ORGANISM: Artificial Sequence
<220> FEATURE:
<223> OTHER INFORMATION: Combined DNA/RNA molecule: siRNA duplex R4
      antisense strand
<220> FEATURE:
<223> OTHER INFORMATION: siRNA duplex R4 antisense strand

<400> SEQUENCE: 2
gcgguaguug uacucauugt t                                                21

<210> SEQ ID NO 3
<211> LENGTH: 21
<212> TYPE: DNA
<213> ORGANISM: Artificial Sequence
<220> FEATURE:
<223> OTHER INFORMATION: Combined DNA/RNA molecule: scrambled control
      duplex Scr4 sense strand
<220> FEATURE:
<223> OTHER INFORMATION: scrambled control duplex Scr4 sense strand

<400> SEQUENCE: 3
gucacaccga uaagucacat t                                                21
```

```
<210> SEQ ID NO 4
<211> LENGTH: 21
<212> TYPE: DNA
<213> ORGANISM: Artificial Sequence
<220> FEATURE:
<223> OTHER INFORMATION: Combined DNA/RNA molecule: scrambled control
      duplex Scr4 antisense strand
<220> FEATURE:
<223> OTHER INFORMATION: scrambled control duplex Scr4 antisense strand

<400> SEQUENCE: 4
ugugacuuau cggugugact t                                             21
```

ANALOGUES OF (−)-PICROPODOPHYLLIN, SYNTHESIS AND USES THEREOF

CROSS-REFERENCE TO RELATED APPLICATION

This application is a continuation of International Application PCT/US09/033,416, filed Feb. 6, 2009 and also claims priority to U.S. Provisional Patent Application Ser. No. 61/027,459, filed Feb. 9, 2008 and U.S. Provisional Patent Application Ser. No. 61/122,945, filed Dec. 16, 2008, the contents of which are hereby incorporated in their entireties herein.

GRANT INFORMATION

The subject matter of this application was developed at least in part under National Institutes of Health Grant No. NIH/1PO1CA097403, so that the United States Government has certain rights herein.

SEQUENCE LISTING

The specification further incorporates by reference the Sequence Listing submitted herewith via EFS on Feb. 20, 2009. Pursuant to 37 C.F.R. §1.52(e)(5), the Sequence Listing text file, identified as "0700503731.TXT," is 1,3661 bytes and was created on Feb. 20, 2009. The Sequence Listing, electronically filed herewith, does not extend beyond the scope of the specification and thus does not contain new matter.

1. INTRODUCTION

The invention relates to (−)-picropodophyllin analogues, methods of synthesizing said analogues and uses thereof. In certain non-limiting embodiments, the invention provides for methods of treating cancers using (−)-picropodophyllin analogues, including basal-like cancers of the breast.

2. BACKGROUND OF THE INVENTION

The compound (−)-picropodophyllin binds tightly to the human Insulin-like Growth Factor I Receptor Kinase (IGF1 RK) domain and inhibits its kinase activity. Such binding has the effect of inhibiting the anti-apoptotic signal pathways that are associated with IGF1 RK activity. This inhibition tends to decrease cancer cell growth and may also render cancer cells more susceptible to chemotherapy. Importantly, the compound, (−)-picropodophyllin, shows exquisite selectivity for the IGF1 RK over the structurally highly homologous Insulin Receptor Kinase (IRK) domain, the inhibition of which would give an undesired diabetes-type phenotype. This selectivity could lead to a new class of chemotherapeutic drugs.

At present, there is no drug on the market that acts upon the IGF1 RK. Development of such a drug is, therefore, an emerging macromolecular target of great current interest in the pharmaceutical community.

Human breast cancers have been molecularly classified by gene expression profiling into three major subtypes: luminal, ERBB2+ and basal-like. The luminal cancers are estrogen receptor-positive (ER+), whereas the cancers of the other two classes, which either overexpress ERBB2(HER2/NEU) or exhibit phenotypic features of basal/myoepithelial cells, are ER-negative (Perou et al., *Nature* (2000), 406, 747-52; Sorlie et al., *Proc. Natl. Acad. Sci. U.S.A.* (2001), 98, 10869-74; Sorlie et al., *Proc. Natl. Acad. Sci. U.S.A.* (2003), 100, 8418-23). Basal-like cancers also lack progesterone receptor (PR) and ERBB2 (ER−/PR−/ERBB2−; "triple negative breast cancers"), but frequently express EGFR and basal markers, such as cytokeratins 5/6 and/or 14 and p63 (Nielsen et al., *Clin. Cancer Res.* (2004), 10, 5367-74). The basal-like class (15-20% of all breast cancers; recently reviewed by Yehiely et al., *Trends Mol. Med.* (2006), 12, 537-44; Finnegan and Carey, *Future Oncol.* (2007), 3, 55-63; Da Silva et al., *J. Clin. Pathol.* (2007), 60, 1328-32) includes high proportions of BRCA1-associated and also medullary and metaplastic subtypes. The latter group is heterogeneous and consists of squamous and spindle cell carcinomas and other forms. Basal cancers appear to have extremely bad prognosis (Sorlie et al., *Proc. Natl. Acad. Sci. U.S.A.* (2001), 98, 10869-74), especially in the early years of follow-up after diagnosis and treatment, although this was not clearly evident in some patient cohorts (Chin et al., *Cancer Cell* (2006), 10, 529-41). In addition, these aggressive cancers pose a serious problem to targeted therapies, considering that the use of antiestrogens in combination with an anti-ERBB2 antibody (trastuzumab) is not an option, while there is no clear choice for chemotherapeutic intervention (see, for example, Cleator et al., *Lancet Oncol.* (2007), 8, 235-44; Carey et al, *Clin. Cancer Res.* (2007), 13, 2329-34).

Interestingly, an association between basal cancers and Kras amplification is now emerging. Ras-family members, apparently serving overlapping but also distinct cellular functions, act as molecular switches in signaling pathways regulating proliferation or apoptosis, and become constitutively active and, thus, oncogenic by mutation (usually at codons 12, 13 or 61). Although Kras is overall the most frequently mutated isoform, there is tissue-specificity and variable incidence of mutations in Ras tumorigenic action, as different human tumors harbor different mutant family members. In contrast to pancreatic ductal adenocarcinoma, in which Kras mutations (most commonly in codon 12) can be found at frequencies as high as 90% (Almoguera et al., *Cell* (1988), 53, 549-54), the incidence of Kras mutations in breast cancer appears to be low (~7% on average; reported frequencies of 1/40, 1/25, 4/61 and 3/10; Rochlitz et al., *Cancer Res.* (1989), 49, 357-360; Prosperi et al., *Cancer Lett.* (1990), 51, 169-74) Myaikas, et al. *Biochem. Biophys. Res. Commun* (1998), 251, 609-612; Chen, et al., *Cancer Lett.*, (2005), 229, 115-22). In human breast cancer cell lines, however, the observed frequency was higher (~13%; 5/40; Hollestelle et al., *Mol. Cancer. Res.* (2007), 5, 195-201). Signaling elicited by non-mutated, but overexpressed Ras can also collaborate with other deregulated pathways in tumor progression and invasion (Clark and Der, *Breast Cancer Res. Treat.* (1995), 35, 133-44). For example, in comparison with control breast tissue, 11 of 20 breast cancers exhibited a 2- to 6-fold increase in enzymatically measured Ras activation (relative amount of GTP-bound form; von Lintig et al., *Breast Cancer Res. Treat.* (2000), 62, 51-62), while Western analysis indicated that in ~70% of primary breast cancer specimens (n=132) the level of Ras was higher than in normal breast tissue (Dati et al., *Int. J. Cancer* (1991), 47, 833-38). Notably, in 56% (9/16) of examined basal-like human breast cancers identified by expression profiling, the Kras locus was amplified and, thus, overexpressed (Herschkowitz et al., *Genome Biol.* (2007), 8, R76).

The IGF signaling system, which is the major determinant of mammalian organismal growth (Efstratiadis A *Int. J. Dev. Biol.* (1998), 42:955-976), has also been implicated in the pathogenesis of various human cancers (Pollak M N, et al., *Nat. Rev. Cancer* (2004), 4:505-518.), including breast tumors (Sachdev D and Yee D, *J Mammary Gland Biol Neoplasia* (2006), 11:27-39). A seminal observation, in this regard, was that cells lacking Igf1r, the tyrosine kinase receptor mediating the effects of insulin-like growth factors, cannot be transformed by any one of several tested oncoproteins (Sell C, et al. *Proc. Natl. Acad. Sci. USA* (1993), 90:11217-11221; Sell C, et al. *Mol. Cell. Biol.* (1994), 14: 3604-3612; Baserga R, *Expert Opin. Ther. Targets* (2005), 9:753-768). Signaling through Igf1r does not appear to be an oncogenic component per se, but a crucial prerequisite for tumorigenesis because, among other actions such as the promotion of cellular proliferation by stimulation of the Ras/MAPK/ERK pathway, it exerts strong PI3 kinase-dependent and independent antiapoptotic effects that are necessary for tumor growth (Baserga R, *Expert Opin. Ther. Targets* (2005), 9:753-768). Moreover, the IGF system appears to be involved in resistance to certain anticancer regimes (Ryan P D and Goss P E, *Oncologist* (2008), 13:16-24). On the basis of these considerations, potential therapeutic approaches for cancer treatment involving blocking of IGF signaling with small molecules or antibodies are currently under development (Sachdev D and Yee D, J *Mammary Gland Biol Neoplasia* (2006), 11:27-39; Baserga R, *Expert Opin. Ther. Targets* (2005), 9:753-768; Ryan P D and Goss P E. *Oncologist* (2008), 13:16-24; Garcia-Echeverria C. *IDrugs* (2006), 9:415-419; Hartog H, et al., *Eur. J. Cancer* (2007) 43:1895-1904).

3. SUMMARY OF THE INVENTION

The present invention provides for compounds, compositions, methods of making, and methods of using analogues of (−)-picropodophyllin, as well as a transgenic animal model and its use for identifying anticancer agents. It is based, at least in part, on the discoveries that (i) Igf1r was overexpressed in mammary tumors advantageously induced extremely rapidly by oncogenic Kras in a mouse model, and (ii) breast-specific genetic ablation of Igf1r expression demonstrated that the cognate signal transduction pathway is causally involved in tumorigenesis.

In particular non-limiting embodiments, the present invention provides for methods of treating a cancer in a subject comprising administering, to the subject, an effective amount of an analogue of (−)-picropodophyllin. In particular, non-limiting embodiments, the cancer cells demonstrate a mutation in Kras. In a specific, non-limiting embodiment, the cancer is a basal-like cancer of the breast.

4. BRIEF DESCRIPTION OF THE FIGURES

FIG. 1A-D. Application of a general method for tissue-specific expression of oncoproteins in mice. (A) Inserts (in pBSK) or two plasmids used for construction of a targeting vector for knock-in of a chosen cDNA into the Eef1a locus ("Eef1a1 cassette"). The first plasmid consists of a splice acceptor site (0.2 kb), a floxed segment that includes a neo selectable marker (0.8 kb) linked to a "stop" sequence (sx-pA; triple polyA; 1.5 kb), and a polylinker (multiple cloning sites; MCS) followed by an additional polyadenylation signal (pA; 0.25 kb). A chosen cDNA is cloned into the MCS, and then the entire compound insert is excised by digestion with PacI and AscI and cloned into the corresponding sites of the second plasmid that provides 5' and 3' homology arms to the final targeting vector. The engineered PacI and AscI sites (separated by a PmeI site) have replaced a SpeI site in the first intron of Eef1a1. The experiments described herein utilized an older version of the first plasmid, in which the neo gene was driven by the Pgk promoter. (B) Homologous recombination in ES cells ("knockin"; indicated by X symbols) using a targeting vector that was constructed by inserting into the MCS of the Eef1a cassette an oncogenic Kras* cDNA. A simplified restriction map and the noncoding and coding exons of the locus (open or filled rectangles, respectively) are indicated. Excision of the "floxed" block from the targeted allele by Cre-mediated recombination (using in this case a Wap-cre transgene for specific expression of the recombinase in mammary glands) allows excision of the "stop" sequence and consequent Kras* transcription driven by the Eef1a promoter. (C) Molecular analysis. Southern analysis was performed using EcoRV-digested DNA that was extracted in the examples shown either from tails of a wild-type or a transgenic animal, or from a Kras*-induced tumor that developed after Wap-cre-mediated recombination. Northern analysis shows that, in addition to the two endogenous Kras mRNAs which are transcribed from the intact allele in wild-type mammary glands (MG), the targeted allele expresses in tumors two new Kras* transcripts (marked by asterisks in the figure). Western analysis using an antibody recognizing the Kras4B isoform encoded by Kras* indicates that the amount of the oncoprotein is significantly higher in mammary tumors than in normal glands. (D) Kaplan-Meier tumor-free mouse survival curves. The survival of female mice from the day of the first parturition until the day of detection of palpable Kras*-induced tumors is compared between animals carrying the oncogenic transgene either in the presence of wild-type Igf1r or in a genetic background in which one or both floxed Igfr1 alleles have been conditionally ablated. In mice possessing at least one intact Igfr1 allele, tumors appear immediately after a single pregnancy, in contrast to the animals with Igfr1 nullizygous mammary epithelial cells (three pregnancies).

FIG. 2A-C. Histology and immunophenotyping of mammary carcinomas. (A) Kras*-induced mouse mammary tumors exhibit four histopathological forms. The insets in the H&E-stained sections (first row) show CISs of the corresponding invasive carcinomas. For details about the immunostaining results, see Example 3 and Table 4. (B) Examples of mouse and human pale breast cancers. A mouse Kras*-induced pale cell carcinoma exhibits a strong histological similarity (H&E staining) with a specimen of human atypical medullary breast cancer and both tumor types are strongly positive for Igf1r immunostaining. (C) KRAS copy gains in some atypical medullary breast cancers with pale cells. The dual color FISH analysis using KRAS (red/lighter) and chromosome 12 centromeric (green/brighter) probes shows that, in cells from three different human pale breast cancer specimens (the right panels are from the same tumor), there are copy gains of the 12p12.1 region (up to 6 KRAS copies).

FIG. 3A-F. Drug treatment of Kras*-induced mammary carcinomas. Examples of tumor development in mice carrying an activated Kras* oncogenic transgene, which were injected either with vehicle ("V", panels A, C and E) or with picropodophyllin ("PPP", designated "P" in the figure, panels B, D, and F). Examination of tumors macroscopically (A, B) and histologically (C, D) after three weeks of treatment showed that, in comparison with the controls (A and C, vehicle), the PPP-treated tumors were dramatically smaller (B and dotted circles in D). Compared to vehicle (E), administration of PPP for 3 days increased ~9-fold the level of apoptosis detected in the pale component, as assayed by activated caspase 3 immunohistochemistry (brown staining). Scale bar=1.0 cm (A and B); scale bar=5.0 mm (C and D). Original magnifications: ×20 (C and D); ×400 (E and F).

FIG. 4A-F. Effects of PPP administration for 3 weeks (P: panels B, D and F) compared to vehicle injection (V, panels A, C and E) on the components of Kras*-induced carcinomas. The PPP treatment diminishes the size of pale cell tumors (B, dotted circles) and results in extensive keratinization (D) and vaculolation (D inset) of the squamous component. Original magnifications: ×200 (A-D); ×40 (D inset); ×400 (E, F).

FIG. 5A-G. Similarity of mouse and human pale breast cancers. A mouse Kras*-induced pale cell carcinoma (A) exhibits a strong histological similarity (H&E staining) with an example of a human atypical medullary breast cancer (C) and both tumor types (B and D, respectively) are strongly positive for Igf1r immunostaining. The dual color FISH analysis using KRAS (red) and chromosome 12 centromeric (green) probes (panels E, F and G; individual cells from three different human pale breast cancer specimens like the one in C) shows amplification of the 12p12.1 region (up to six KRAS copies).

Figure 6:
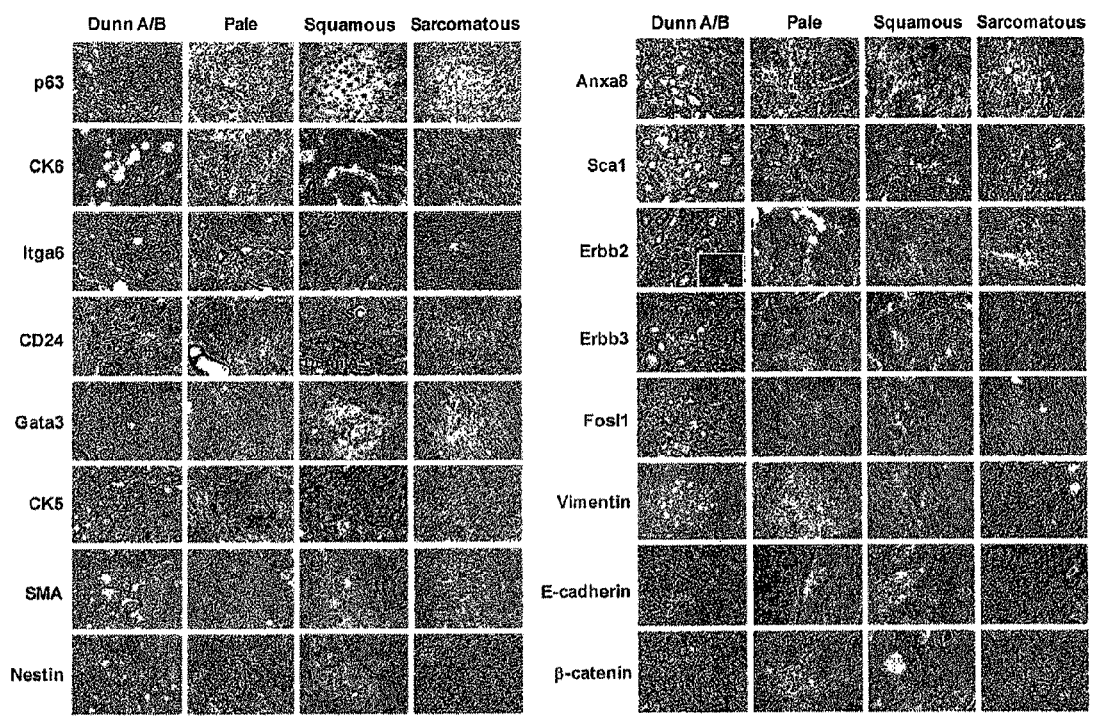

FIG. 6. Immunophenotyping of Kras*-induced mouse mammary carcinomas (Part II).

Figure 7:
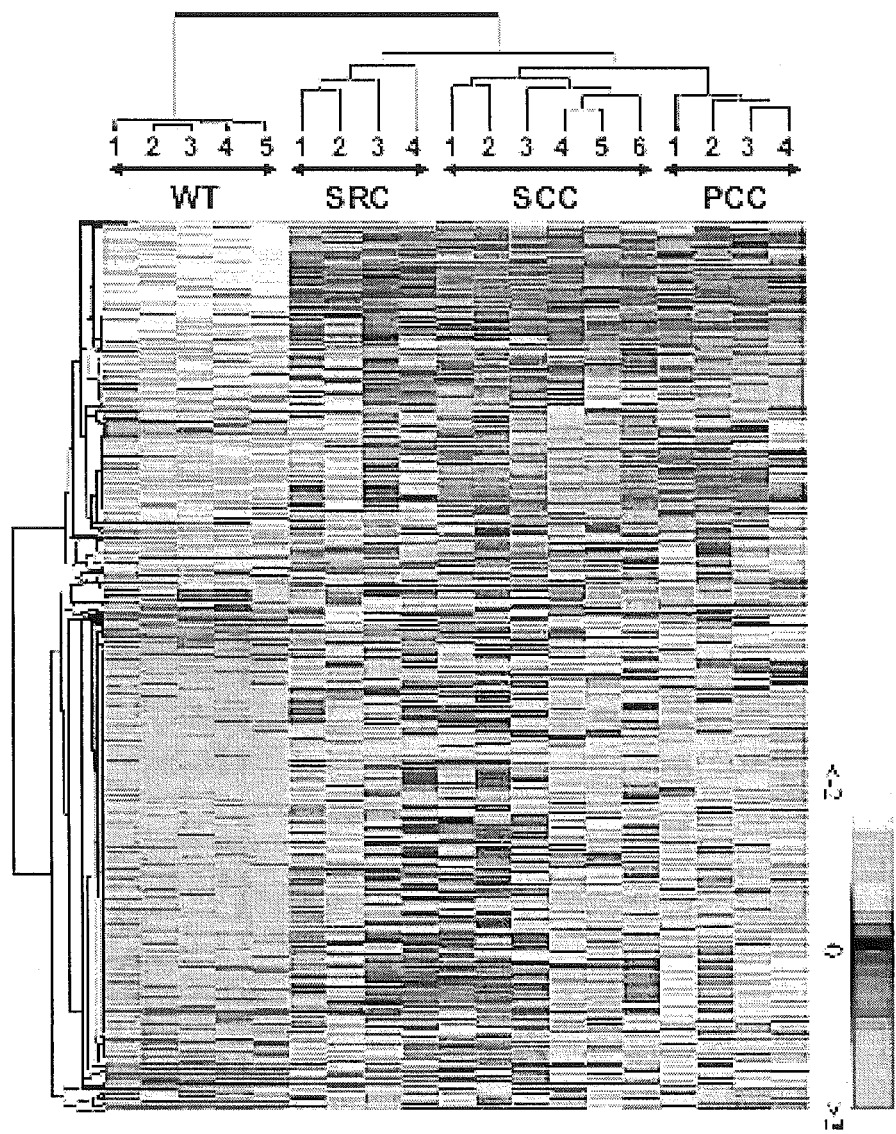

FIG. 7. Hierarchical clustering of genes (rows) and specimens (columns). The dendrogram shown (derived by unsupervised analysis using CYGWIN software) reveals that there is clear discrimination in gene-expression patterns between normal (WT) mammary glands and tumor specimens stratified according to the degree of their enrichment in one of the three basal-like components (sarcomatous, SRC; squamous, SCC; and pale, PCC). A scale is shown on the right.

Figure 8:
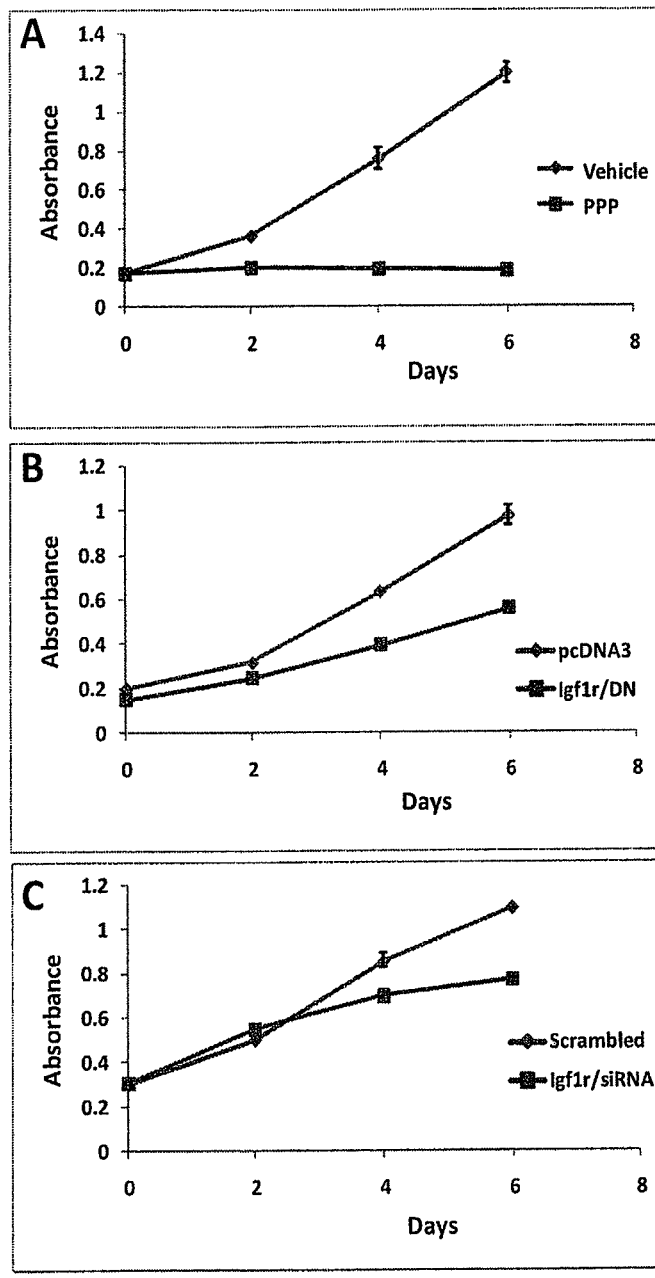

FIG. 8A-C. In vitro inhibition of Igf1r action. Representative experiments of pharmacological inhibition of IGF1R in MDA-MB-231 cells by picropodophyllin (A) or by IGF1R knockdown using a dominant-negative construct (B) or siRNA (C). The absorbance (mean values±S.E.M.) reflects cell numbers estimated from duplicate samples using the MTT assay (see Experimental Procedures). (A) MDA-MB-231 cells were seeded in 24-well plates at 10% confluence (day 0) and treated with vehicle (DMSO; final concentration 0.1%) or PPP dissolved in DMSO (final concentration 500 nM). (B) Plasmid 486Stop (encoding dominant-negative IGF1R) or a control plasmid (pcDNA3) were introduced in MDA-MB-231 cells by nucleofection following the manufacturer's protocol (1.5 μg of plasmid DNA per 106 cells; Amaxa Biosystems). The same method was used to introduce into these cells a 19-bp RNA duplex (R4) targeting IGR1R mRNA or a scrambled control duplex (Scr4; see SI Materials and Methods, for details). The efficiency of nucleofection under our conditions (estimated by adding to the samples a GFP-expressing plasmid) was ~60%.

Figure 9:
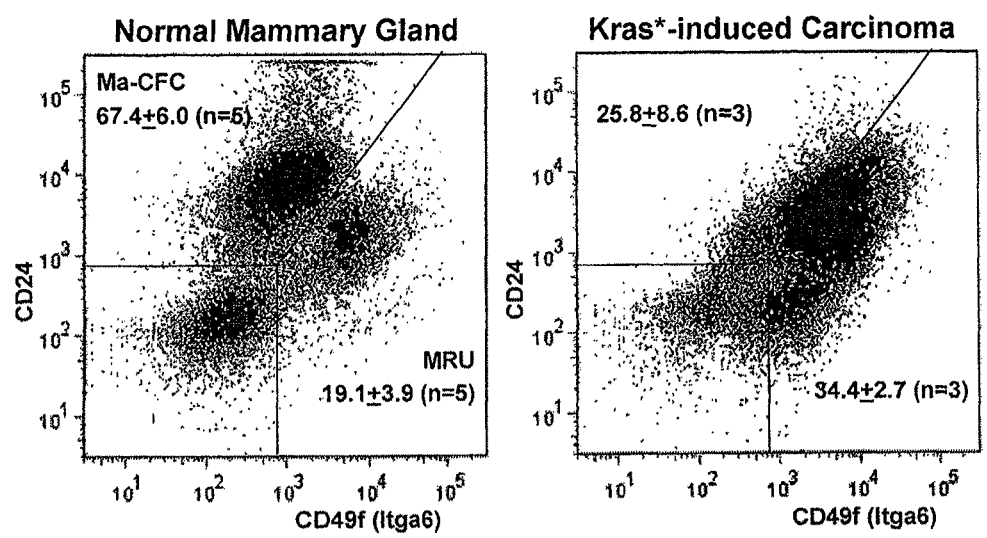

FIG. 9. Example of FACS Analysis of Mammary Cell Suspensions. Cells were isolated from normal mammary glands of parous animals or from invasive mammary carcinomas that developed in mice carrying a Kras* oncogenic transgene. Flow-sorting of progenitor cell populations was performed as described (Stingl, J. et al. *Nature* (2006), 439: 993-997). The MRU fraction (mammary repopulation units) is enriched in mammary stem cells, whereas the Ma-CFC fraction (mammary colony-forming cells) is enriched in luminal cell precursors. Ma-CFCs are CD24$^+$ CD49f$^{medium}$, whereas MRUs are CD24$^+$ CD49f$^{high}$. The percentages of cells in these populations are indicated.

Figure 10:
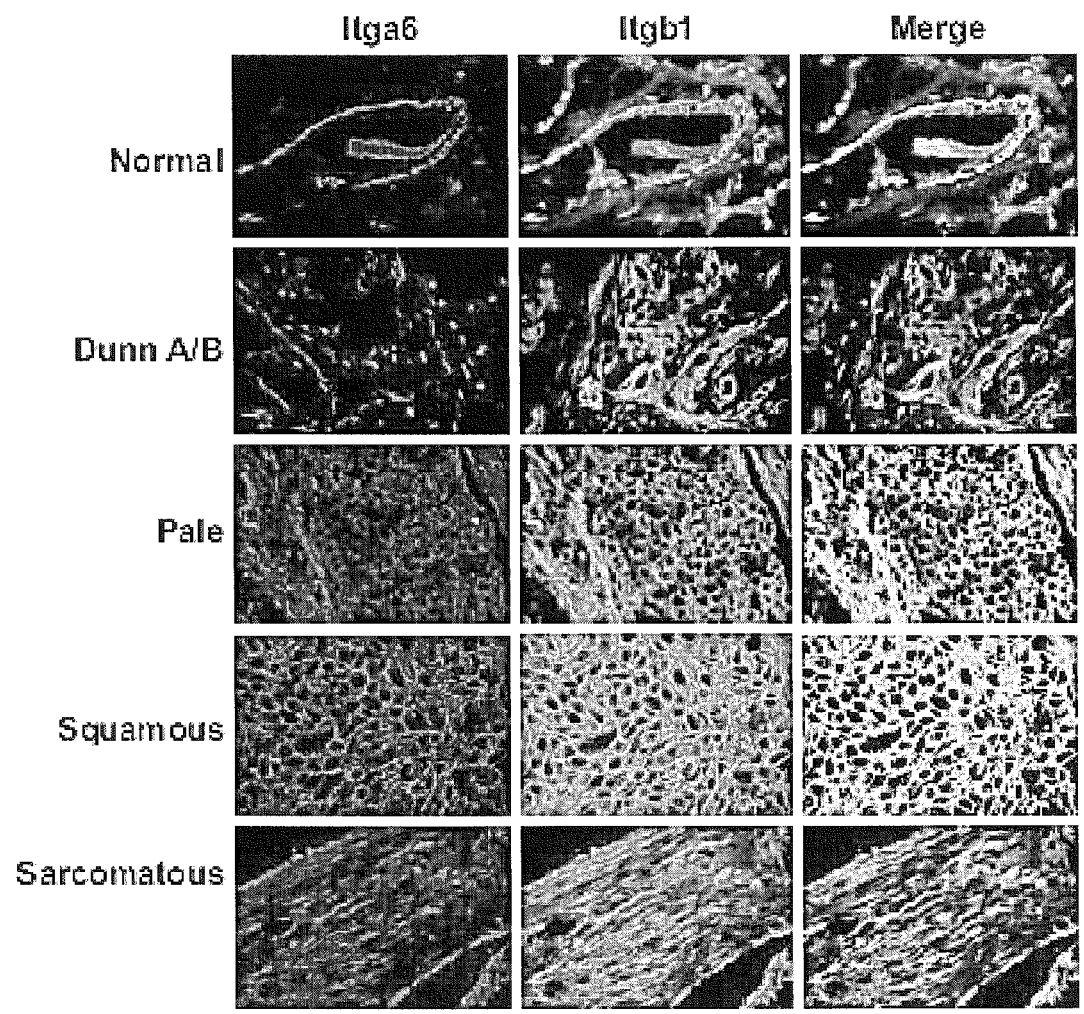

FIG. 10. Localization of integrins α6 (CD49f) and β1 (CD29). The distribution of Itga6 and Itgb1 in normal mammary glands and in the four histopathological forms of Kras*-induced invasive carcinomas was determined by double immunofluorescence using the antibodies listed in Table 9. Both markers were found co-localized in the basement membrane of the myopithelial layer in normal glands. Itgb1 was also present in the basolateral, but not the luminal aspect of luminal cells. This distribution was maintained in microacinar adenocarcinomas, but only for Itgb1, whereas the basal-like forms had altered patterns. Thus, all SCC cells exhibited intense labeling for both markers co-localized circumferentially, while the intensity of signal in PCC and SRC was variable and did not involve all cells.

5. DETAILED DESCRIPTION OF THE INVENTION

The invention provides inhibitors of IGF1RK as well as methods of synthesizing the inhibitors and using them therapeutically. As therapeutics, these small molecules have advantages over antibodies, including circumventing possible immune responses associated with the latter, as well as permitting oral administration and potentially increasing biological half-life. Production cost is also likely to be much lower.

An aspect of the invention is directed to analogues and a method for the synthesis of analogues of the natural product (−)-picropodophyllin with control of both absolute and relative stereochemistry. Absolute and relative stereochemistry are important for biological activity in lignans.

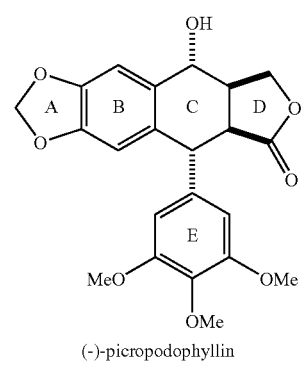

(−)-picropodophyllin

Thus, (−)-podophyllotoxin, the C-2-epimer of (−)-picropodophyllin, features a structurally distinct trans-fused lactone in the D-ring. (−)-Podophyllotoxin acts as an antimitotic and does so by binding tightly to tubulin, thereby preventing its polymerization in spindle formation. The structure of the (−)-podophyllotoxin-tubulin complex has been established by x-ray crystallography.

If one inverts the C-4 center one arrives at the family of epipodophyllotoxins [i.e. epimers at both C-2 and C-4 of (−)-picropodophyllin], including etoposide, teniposide, and TOP-53. These compounds act by binding to the enzyme topoisomerase II and inhibiting the religation step along the enzymatic reaction coordinate. This leads to a build up of a covalent enzyme-DNA complex that serves as a cellular signal, triggering apoptosis.

Thus, while members of all three of these lignan families are of interest as potential medicinal agents, if one wishes to develop chemotherapeutics that target the IGF1 RK, control of stereochemistry is important, and represents an important feature of this invention.

The natural product (−)-picropodophyllin is shown above as 1.

Aspects of the present invention are directed to analogues of (−)-picropodophyllin having modified E-rings as shown below in formula I.

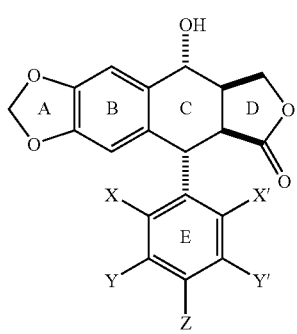

I

Many types of substitutents are available for ring E due to the late addition of ring E during synthesis of the compounds.

X, X', Y, Y' and Z are ring E substituents and X, X', Y, Y' and Z may be independently hydrogen; deuterium; tritium; a $C_1$-$C_8$ saturated or unsaturated, alkyl or cycloalkyl group; a hydroxyl group; an ether-protected hydroxyl group bearing a $C_1$-$C_8$ saturated or unsaturated alkyl or cyclic alkyl group; a carboxylate ester-protected hydroxyl group derived from a $C_1$-$C_8$ saturated or unsaturated, cyclic or acyclic, carboxylic acid; a hydroxyl group protected as a phosphate mono-, di- or triester, the di-, or triester having $C_1$-$C_4$ saturated or unsaturated alkyl group(s); a $C_1$-$C_8$ alkoxy, a $C_1$-$C_4$ alkoxy, a phosphonate mono- or diester-protected hydroxyl group derived from a $C_1$-$C_8$ saturated or unsaturated, cyclic or acyclic, phosphonic acid wherein the diester also contains a $C_1$-$C_8$ saturated or unsaturated alkyl group; a phosphinate ester-protected hydroxyl group derived from a phosphinic acid bearing two $C_1$-$C_8$ saturated or unsaturated, cyclic or acyclic, alkyl groups; a hydroxyl group protected as a sulfate mono- or diester bearing a $C_1$-$C_4$ saturated or unsaturated alkyl group; a hydroxyl group protected as a sulfonate ester derived from a sulfonic acid bearing a $C_1$-$C_8$ saturated or unsaturated, cyclic or acyclic, alkyl group; an amino group; a primary or secondary amine bearing 1 to 2 $C_1$-$C_8$ saturated or unsaturated alkyl group(s), respectively; a carboxamide-protected, unsubstituted or primary amine bearing a $C_1$-$C_4$ saturated or unsaturated alkyl group; an amino group derived from a $C_1$-$C_8$ saturated or unsaturated, cyclic or acyclic, carboxylic acid; a carboxylic acid; a carboxylate ester bearing a $C_1$-$C_4$ saturated or unsaturated alkyl group; a phosphonic acid; a phosphonate mono- or diester bearing 1 to 2 $C_1$-$C_4$ saturated or unsaturated alkyl group(s), respectively; a phosphinic acid having a $C_1$-$C_8$ saturated or unsaturated, cyclic or acyclic, alkyl group or ester bearing a $C_1$-$C_4$ saturated or unsaturated alkyl group; a formyl group; an acetyl group; a benzoyl group; a carboxamide group derived from ammonia or from a primary or secondary amine bearing 1 to 2 $C_1$-$C_4$ saturated or unsaturated alkyl group(s), respectively; a sulfhydryl group; a thioether bearing a $C_1$-$C_8$ saturated or unsaturated, cyclic or acyclic, alkyl group; a sulfonic acid, a sulfonate ester bearing a $C_1$-$C_4$ saturated or unsaturated alkyl group; an alkylsulfonyl group bearing a $C_1$-$C_8$ saturated or unsaturated, cyclic or acyclic, alkyl group; a phenylsulfonyl group; a sulfoxide bearing a $C_1$-$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group with the proviso that when X and X' are H, Y, Y', and Z cannot all be methoxy.

In further aspects, X, X', Y, Y' and Z are independently hydrogen, a $C_1$-$C_8$ alkyl or $C_1$-$C_8$ alkoxy group. In further aspects, X, X', Y, Y' and Z are hydrogen, methyl, or methoxy with the proviso that when X and X' are H, Y, Y', and Z cannot all be methoxy.

In further aspects, the present invention is directed to (−)-picropodophyllin analogues with modified E-rings as shown below.

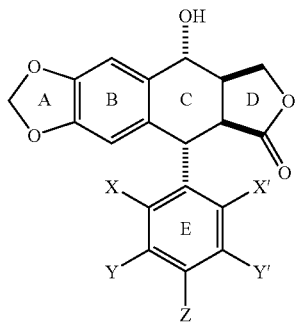

Wherein
(1) X, X', Y, Y'=H, and Z=OCH$_3$ (compound 19, below)
(2) X, X', Y', Z=H, and Y=OCH$_3$;
(3) X, X', Y, Z=H, and Y'=OCH$_3$ (compound 18, below)
(4) X, X', Y'=H, and Y, Z=OCH$_3$;
(5) X, X', Y=H, and Y', Z=OCH$_3$ (compound 20, below)
(6) X, X', Z=H, and Y, Y'=OCH$_3$ (compound 21, below)
(7) X, X', Y, Y'=H, and Z=CH$_3$
(8) X, X', Y, Y'=H, and Z=CH$_3$, C(4)-epimer-4-epi-picropodophyllin analaogue)

The present invention is also directed to enantiomerically enriched compounds which do not occur naturally and are not readily available from (−)-picropodophyllin. Enantiomerically enriched means that the enantiomeric ratio is at least 95:5, preferably at least 97:3, prior to recrystallization.

The present compounds may be prepared by first preparing a compound of formula (a) by any suitable means such as starting from readily available piperonal, utilizing (i) bromination, (ii) acetalization and (iii) installation of a hydroxymethyl group (halogen/metal exchange and aryllithium trapping with paraformaldehyde).

In the presence of acetic acid, formula (a) cyclizes and, upon losing two molecules of MeOH, transiently provides the highly reactive isobenzofuran (b), which reacts, in situ, via a Diels-Alder reaction with DMAD (dimethyl acetylenedicarboxylate) to form Diels-Alder adduct (c).

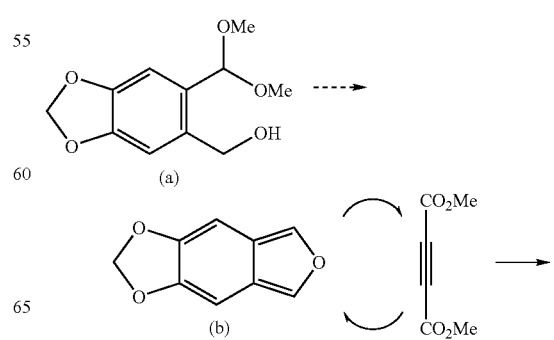

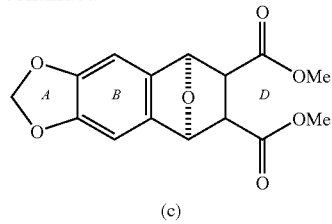

(c)

Diels-Alder adduct (c) can be selectively hydrogenated, reduced to the diol with LiAlH$_4$ and acetylated to provide meso diacetate (d).

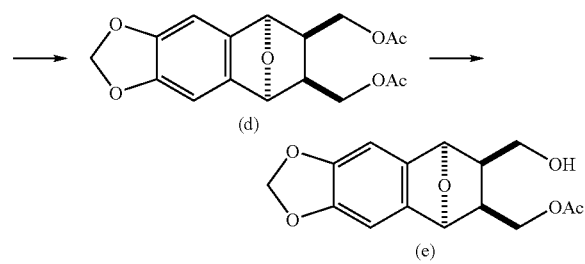

The achiral and symmetrical system bearing all carbons of the target cyclolignan A-D rings is efficiently desymmetrized with porcine pancreatic lipase (PPL) to produce (e) in synthetically useful enantiopurity level.

The compound of formula (e) is subjected to silylation, deacetylation, and oxidation to produce a compound of formula (f) without loss of optical activity. Silylation occurs with a silylating agent, R$^9$X, including but not limited to TIPSCl (triisopropylsilyl chloride), TBDMSCl (tert-butyldimethylsilyl chloride), and TBDPSCl (tert-butyldiphenylsilyl chloride), in the presence of an appropriate base such as imidazole or NEt$_3$. Deacetylation is carried out under standard conditions (e.g. Et$_2$O, NaHCO$_3$, or K$_2$CO$_3$, MeOH or Na, MeOH or NH$_3$, MeOH.) The aldehyde is then oxidized under mild two-electron oxidation conditions (e.g. Swern or Moffatt oxidation (DMSO as oxidant), Ley oxidation (TPAP=tetrapropylammonium perrhuthenate as oxidant) or Dess-Martin oxidation (Dess-Martin periodinane as oxidant.))

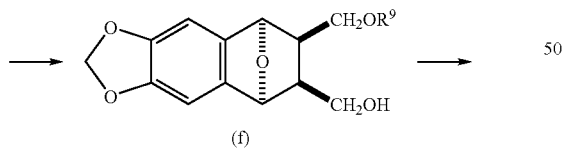

R$^9$ is a silyl protecting group such as a triisopropylsilyl-protecting group.

The compound of formula (f) is converted to a compound of formula (g) by retro-Michael ring opening and protection of the C$_4$—OH followed by aldehyde oxidation. The ring opening occurs under typical Michael addition conditions (such as NaOMe and MeOH). The protection step must be carried out under neutral to basic conditions (to avoid aromatization). Use of a silyl (such as TES=triethylsilyl)ether protecting group for the C-4 hydroxyl is an advantageous feature of the present invention. This sets the stage for an efficient desilylative lactonization at the close of the synthesis, unveiling the (−)-picropodophyllin core in a single operation, immediately following the stereocontrolled installation of ring E.

Aldehyde oxidation proceeds smoothly under Lindgren conditions (NaClO$_2$ as oxidant) to give (g). The efficient retro-Michael ring-opening of (f) unveils the (methylenedioxy)cinnamyl system as the vehicle for late installation of ring E.

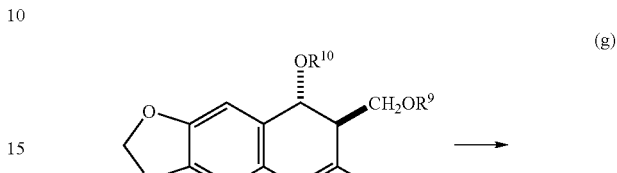

R$^{10}$ is a C$_4$ protecting group such as a triethylsilyl-protecting group.

The compound of formula (g) is converted to a compound of formula (h) by transformation of the carboxylic acid into an acyl oxazolidinone functionality. This requires carboxyl activation (e.g. with carbonyl diimidazole) and then condensation with a metalated oxazolidinone to give (h).

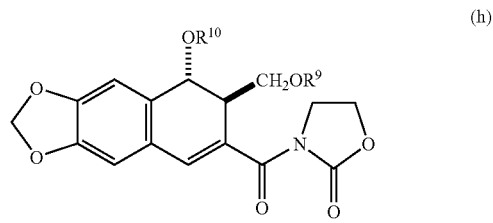

The E ring is introduced to the compound of formula (h) to form a compound of formula (I) by Cu$^1$-mediated conjugate addition of RMgBr at a temperature of −10 to 10° C.

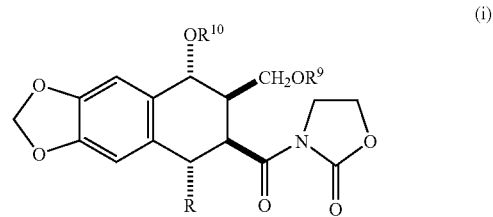

The compound of formula (i) is converted to a compound of formula (j) by desilylative lactonization by heating with a fluoride source and cyclization to produce the corresponding lactone;

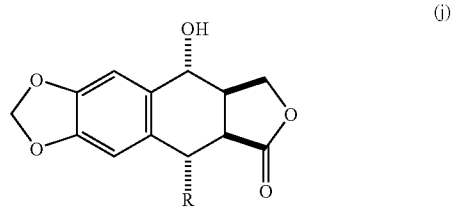

Non-limiting examples of such syntheses are provided in Section 6, Example 1, below, the details of which are incorporated by reference in their entirety into this Section 5.

Further aspects of the invention are directed to (−)-picropodophyllin analogues as shown below.

II

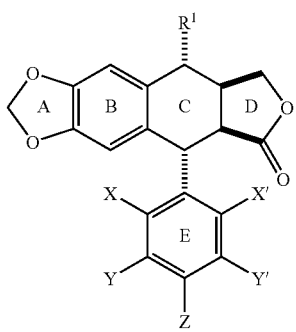

wherein X, X', Y, Y', and Z are defined as above; $R^1$ may be oxo, —OH, —OCH$_3$, —OC$_2$H$_5$, —OC$_3$H$_7$, —OC$_4$H$_9$, —OCH$_2$CH═CH$_2$, —OCH$_2$Ph, —OCH$_2$CH$_2$NH$_2$, —OCOH, OCOCH$_3$, —OCH$_2$OH, OC$_2$H$_4$OH, —OC$_3$H$_6$OH, —OC$_4$H$_8$OH, or a glycoside. In specific, non-limiting embodiments, $R^1$ may be oxo, —OH, —OCH$_3$, —OC$_2$H$_5$, —OC$_3$H$_7$, —OC$_4$H$_9$, —OCH$_2$CH═CH$_2$, —OCH$_2$Ph, —OCH$_2$CH$_2$NH$_2$, —OCOH, OCOCH$_3$, —OCH$_2$OH, OC$_2$H$_4$OH, —OC$_3$H$_6$OH, —OC$_4$H$_8$OH, or a glycoside and X, X', Y, Y' and Z are selected from the group consisting of (1) X, X', Y, Y'═H, and Z═OCH$_3$; (2) X, X', Y', Z═H, and Y═OCH$_3$; (3) X, X', Y, Z═H, and Y'═OCH$_3$; (4) X,X',Y'═H, and Y, Z═OCH$_3$; (5) X,X',Y═H, and Y', Z═OCH$_3$; (6) X, X', Z═H, and Y, Y'═OCH$_3$; X, X', Y, Y'═H, and Z═CH$_3$ and (8) X, X', Y, Y'═H, and Z═CH$_3$, C(4)-epimer-4-epi-picropodophyllin analaogue).

III

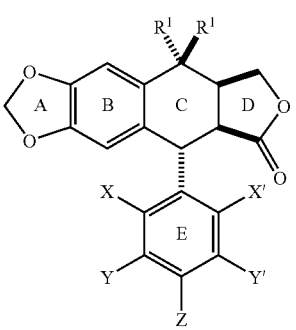

wherein X, X', Y, Y', and Z are defined as above; $R^1$ and $R^2$ may be independently oxo, —OH, —OCH$_3$, —OC$_2$H$_5$, —OC$_3$H$_7$, —OC$_4$H$_9$, —OCH$_2$CH═CH$_2$, —OCH$_2$Ph, —OCH$_2$CH$_2$NH$_2$, —OCOH, OCOCH$_3$, —OCH$_2$OH, OC$_2$H$_4$OH, —OC$_3$H$_6$OH, —OC$_4$H$_8$OH, or a glycoside. In specific, non-limiting embodiments, $R^1$ and $R^2$ may be independently oxo, —OH, —OCH$_3$, —OC$_2$H$_5$, —OC$_3$H$_7$, —OC$_4$H$_9$, —OCH$_2$CH═CH$_2$, —OCH$_2$Ph, —OCH$_2$CH$_2$NH$_2$, —OCOH, OCOCH$_3$, —OCH$_2$OH, OC$_2$H$_4$OH, —OC$_3$H$_6$OH, —OC$_4$H$_8$OH, or a glycoside, and X, X', Y, Y' and Z are selected from the group consisting of (1) X, X', Y, Y'═H, and Z═OCH$_3$; (2) X, X', Y', Z═H, and Y═OCH$_3$; (3) X, X', Y, Z═H, and Y'═OCH$_3$; (4) X, X', Y'═H, and Y, Z═OCH$_3$; (5) X, X', Y═H, and Y', Z═OCH$_3$; (6) X, X', Z═H, and Y, Y'═OCH$_3$; X, X', Y, Y'═H, and Z═CH$_3$ and (8) X, X', Y, Y'═H, and Z═CH$_3$, C(4)-epimer-4-epi-picropodophyllin analaogue).

Examples of suitable $R^1$ and $R^2$ substituents include the substituents disclosed in U.S. Pat. Nos. 5,132,322; 5,300,500; 5,332,811; 5,541,223; and 6,051,721 which are each incorporated herein by reference.

Preferred, non-limiting embodiments of the invention include 5'-Didemethoxy-(−)-picropodophyllin (Compound 18), 3',5'-Didemethoxy-(−)-picropodophyllin (Compound 19), 5'-Demethoxy-(−)-picropodophyllin (Compound 20), and 4'-Demethoxy-(−)-picropodophyllin (Compound 21), the syntheses of which are described in the working examples.

The effects of the compounds described above on activities of IGF1R can be determined in in vitro and in vivo assays, as described in the Examples below. Example 2 describes a method of monitoring the effect of compounds on cell growth. Inhibition of kinase activity of the IGF1R can be measured by any means known in the art. The kinase domain of the receptor is available from Upstate Biotechnology.

In one embodiment, a cell line is used to assay the effects of these compounds on activities of IGF1R, for example, a murine breast cancer cell line derived from Kras* mice. In one embodiment, the cell line is placed in a multi-well-plate, including, but not limited to a 24-well plate, and a 96-well plate. In one embodiment, cells contained in a subset of wells are treated with a substrate, for example, a substrate used in a calorimetric metabolic assay that reflects cell density, for example, MTT (Thiazol Blue Tetrazolium), and cells in another subset of wells are treated with an IGF1R inhibitor, for example, cyclolignan picropodophyllin (PPP), or the compound(s). The effectiveness of these compounds on activities of IGF1R is compared with that of a known IGF1R inhibitor, for example, PPP.

The Kras* mouse is a suitable in vivo model in which to test the effect of IGF1RK inhibitors on tumor growth (see Examples 3 and 4). The Kras* mouse overexpresses a Kras2 gene carrying the oncogenic substitution G12D. The gene has been knocked-in into the highly and ubiquitously expressed locus Eef1a. Cre-mediated removal of a STOP sequence residing upstream from the Kras* cDNA allows for its tissue-specific expression. Mice in which the oncogene is activated in the mammary epithelium by use of the WAPcre line develop tumors very rapidly (as early as 2 days upon parturition; T50=9 days). Moreover, these tumors display high heterogeneity in histopathology. Four major patterns of invasive carcinoma were detected (well differentiated glandular adenocarcinoma (Dunn A and B Tumors), pale cell carcinoma, squamous cell carcinoma and spindle cell (sarcomatous) carcinoma). In addition, histopathological characterization of the tumors showed that, with the exception of the glandular adenocarcinoma, these tumors express basal markers and share great similarities in expression profiles with human and mouse basal-like breast cancers. Expression profile analysis and immunophenotyping showed that the IGF1R was significantly overexpressed in the Kras*-induced neoplasms. This is believed to be the first description of a mouse model in which a malignant neoplasm is induced by a single tumorigenic stimulus in one step without a requirement for secondary oncogenic events, as evidenced by the rapidity of tumor development. This unexpected observation can be attributed to the abnormally high expression levels of a powerful oncogene.

Accordingly, in one set of embodiments, the present invention provides for a system and a method for producing a transgenic animal model of a human tumor, wherein a tumor in the transgenic animal is induced by expression of an oncogene operably linked to a Eef1a (for Eukaryotic translation Elongation Factor 1 Alpha 1) promoter (e.g., the endogenous promoter), and expression of the oncogene is triggered by excision of a "stop" (transcription termination) signal by Cre-mediated recombination. The oncogene may be introduced into the Eef1a1 locus by "knockin" technology into an area of the gene such that, after transcription, it will be translated. In one embodiment, a cDNA encoding the oncogene is inserted into an intron as part of a construct having a splice acceptor site (i) downstream of a "floxed" stop signal and (ii) upstream of the cDNA coding sequence (to prevent the construct sequence being spliced out from the mRNA precursor and lost during mRNA maturation); preferably, the construct is inserted into the first intron. However, the present invention also envisions inserting a construct comprising the cDNA encoding the oncogene into an exon of the Eef1a locus, although this would be less desirable. In various embodiments of the invention, the oncogene may be any oncogene known in the art, including but not limited to Kras and activating mutations thereof (e.g., at codons 12, 13, or 61, e.g., G12D), Hras, c-myc, Her2/neu, src, Wnt 1, PI3 kinase, etc.

In non-limiting set of embodiments of the invention, an Eef1a1 cassette may be prepared comprising (from upstream to downstream) (i) a 5' arm homologous to the Eef1a1 site being targeted; (ii) a splice-acceptor site; (iii) a loxP site; (iv) a transcription termination signal (e.g., a multiple signal serving, before its removal, as a block "STOP" sequence); (v) a loxP site; (vi) a multiple cloning site; (vii) a polyadenylation signal and (viii) a 3' arm homologous to the Eef1a1 locus targeted, further comprising a nucleic acid encoding a selectable marker (e.g., neo), positioned upstream of the transcription termination signal. Any gene of interest, including but not limited to an oncogene such as Kras or an activated form thereof (designated "Kras*" herein), may be inserted into the multiple cloning site. A non-limiting example of such a construct is shown in FIGS. 1A and 1B. ES cells may be electroporated with this cassette, expression of the selectable marker may be used to select for targeted cells, and integration at the correct locus may be confirmed by standard techniques. An ES cell carrying the desired "knockin" transgene may then be used to produce a first transgenic animal that can transmit the genetic modification to its progeny.

According to the present invention, a first transgenic animal carrying an Eef1a1 cassette described in the preceding paragraph may be mated with a second transgenic animal carrying a transgene comprising a Cre-gene operably linked to a promoter, where the promoter is either active or shows increased activity in a specific tissue, and/or at a specific developmental stage, and or under certain conditions (e.g., during late pregnancy and lactation, or in response to an agent such as tetracycline or tamoxifen). Thus, an initially dormant oncogene present in the Eef1a1 cassette may be conditionally activated. In progeny animals carrying both the Eef1a1 cassette and the Cre transgene, the nature of the Cre-linked promoter determines the site and timing of oncogene expression, as Cre expression results in removal of the stop transcription signal and, consequently, permits transcription of the oncogene. Accordingly, the present invention may be used to produce tumors in specific tissues; a Cre gene operably linked to a pancreas-specific promoter such as Pdx1 may be used to induce pancreatic cancer in a progeny animal; a Cre cDNA operably linked to a colon-specific promoter such as villin may be used to produce a colon cancer in a progeny animal, and so forth. In a specific, non-limiting embodiment to develop an animal model system for breast cancer (luminal type, ERBB2+ type, and (in particular) basal-like), the second transgenic animal may carry a transgene in which a Cre gene is operably linked to a milk whey acidic protein ("Wap") promoter, so that a selected progeny animal for use as a model of breast cancer carries the Eef1a1 cassette and the Wap-Cre transgenes. Oncogene expression may be induced in such an animal by lactation. FIG. 1B depicts the targeted Eef1a1 locus after Cre-mediated excision of the termination signal. As reported in the working example below, where the oncogene is an activated Kras* gene, a tumor may be produced in as short a time as 2 days following parturition.

The transgenic animal produced according to the invention may be any non-human species of animal. In a preferred, non-limiting embodiment, the transgenic animal is a mouse.

In a related set of non-limiting embodiments, the present invention provides for a cell line derived from a transgenic animal model, as described above, where the cell line is produced from a cancerous cell of the transgenic animal model in which the oncogene transgene is being expressed. In a specific, non-limiting example, the cell line is prepared from a mammary tumor of a transgenic mouse expressing activated Kras* under transcriptional control of the Eef1a1 promoter, as described in FIG. 1B.

In a further related set of non-limiting embodiments, the present invention provides for a transgenic animal carrying, in addition to Eef1a1 cassette and promoter/Cre transgenes as described above, a heterozygous mutation of Igf1R.

In various non-limiting embodiments, the present invention provides for use of a transgenic animal model of a human tumor, as described above, to identify an agent useful for the treatment of said human tumor, where the nature of the tumor is determined by the site of expression of the oncogenic transgene. In various non-limiting embodiments, the transgenic animal model may be a model for breast cancer, or for pancreatic cancer, or for colon cancer, or for lung cancer, or for skin cancer, or for prostate cancer. In a specific, non-limiting embodiment, the transgenic animal model is a model of basal cell type breast cancer.

Accordingly, the present invention provides for a method comprising (i) providing a transgenic animal, as described above, carrying a Eef1a1 cassette comprising a Cre-activatable oncogene and a transgene comprising Cre under the control of a promoter permitting conditional activation of Cre expression; (ii) providing a condition which results in the expression of Cre in the animal with consequent expression of the oncogene; (iii) administering, to said animal, a test agent; and (iv) determining the effect of the test agent on the growth and/or histology of a tumor in the tissue in which the oncogene is activated by Cre and expressed, and/or determining clinical markers associated with malignancy and/or determining the survival of the animal, where the ability of the test agent to inhibit growth of the tumor, or increase differentiation in the histology of the tumor, or decrease one or more clinical marker of malignancy, or increase the survival of the animal, indicates that the test agent may be used to treat the human tumor being modeled, and may be advanced to human clinical trials. Step (iv) may be achieved by providing a second transgenic animal essentially genetically identical to the animal of step (i), providing essentially the same condition as provided in step (ii), and then determining tumor growth and/or histology and/or clinical markers associated with malignancy and/or survival in the second animal, which is not administered the test agent and serves as a negative control and comparing the results with those obtained with the transgenic animal that had received the test agent. Multiple animals may be administered different dosages of test agent to evaluate dose/benefit effect. Clinical markers of malignancy include, but are not limited to, weight of the animal, as well as features associated with the tumor resulting from oncogene expression (for example, a mammary tumor is readily palpable). In preferred non-limiting embodiments, the test agent is a picropodophyllin analogue, such as, but not limited to, those described herein, or another test agent which is an Igf1r inhibitor. Analogous experiments may be performed using a cell line prepared from the transgenic animal expressing the oncogene, wherein, after administration of test agent, features of the malignant phenotype, including rate of proliferation, contact inhibition, ability to grow in soft agar, and markers of apoptosis, may be measured (and where preferably these features are compared between cells exposed to the test agent and control cells which are not).

In further non-limiting embodiments, the present invention provides for a method of treating a cancer, e.g. a cancer for which intact signaling of Igf1r is related to tumor development and/or K ras is activated, amplified and/or mutated, comprising administering, to a subject in need of such treatment, an effective amount of a picropodophyllin analogue as described herein. Igf1r-related cancers include, but are not limited to breast cancer, prostate cancer, glioblastoma, colon cancer, liver cancer, and ovarian cancer. Optionally, said subject may further be administered a dose of a second cancer therapeutic agent, for example, but not limited to, an epidermal growth factor receptor inhibitor such as erlotinib, a Raf/neoangiogenesis inhibitor such as sorafenib, or other agent known in the art.

In still further, non-limiting embodiments, the present invention provides for a method of treating basal like breast cancer, comprising administering, to a human subject diagnosed as having basal like breast cancer, an effective amount of picropodophyllin or an analogue thereof, including, but not limited to, a picropodophyllin analogue as set forth herein. Optionally, said subject may further be administered a dose of a second cancer therapeutic agent, for example, but not limited to, an epidermal growth factor receptor inhibitor such as erlotinib, a Raf/neoangiogenesis inhibitor such as sorafenib, or other agent known in the art. In specific, non-limiting examples, said basal like breast cancer has a phenotype which is estrogen receptor negative, progesterone receptor negative, and ERBB2 negative. In further specific, non-limiting examples, said basal-like breast cancer has a phenotype which includes one or more of the following: epidermal growth factor receptor positive, cytokeratin 5 positive, cytokeratin 6 positive cytokeratin 14 positive, and/or p63 positive.

In specific, non-limiting embodiments of the invention, an effective amount of picropodophyllin or an analogue thereof, for use in methods of treatment as described above, may be between about 30 mg/kg and 80 mg/kg, and may be adjusted to optimize effectiveness using standard pharmaceutical techniques. In those specific non-limiting embodiments where erlotinib is added, the dose may be, for example and not by limitation, between about 25 mg/day and 200 mg/day, or between about 50 mg/day and 150 mg/day, for a treatment interval between about 1 day and until treatment is deemed successful or adverse effects prevent its continuation. In specific, non-limiting embodiments, the amount administered results in a concentration local to the cancer of between about 200 nM and about 800 nM. In specific, non-limiting embodiments, the analogue is compound 18 or compound 21 in an amount that, when administered, results in a concentration local to the cancer of between about 200 nM and about 800 nM or about 300-600 nM or about 400-500 nM.

Said picrodophyllin and/or analogue thereof may be administered by any route known in the art, including but not limited to, local application at tumor site or at site of tumor excision, intravenous administration, intraarterial administration, intraperitoneal administration, intrathecal administration, intraventricular administration, intramuscular administration, subcutaneous administration, oral administration, topical administration, etc. In one specific non-limiting embodiment the picropodophyllin analogue is compound 18 herein. In another specific non-limiting embodiment the picropodophyllin analogue is compound 21 herein.

IGF1RK inhibitors of the invention can be formulated as pharmaceuticals using methods well known in the art. Pharmaceutical formulations of the invention typically comprise at least one IGF1RK inhibitor of the invention mixed with pharmaceutically acceptable carrier. Preferably the solutions are sterile and non-pyrogenic. Compounds of the invention can be formulated for parental administration by a variety of routes, including by mouth, by injection (e.g., by bolus injection), or by infusion.

IGF1RK inhibitors of the invention can be administered to patient, either alone or in pharmaceutical compositions where they are mixed with suitable carriers or excipient(s) at doses to inhibit cancer cell growth as a single agent. IGF1RK inhibitors of the invention may also make cancer cells more vulnerable to treatment with other agents and therefore can be used to supplement standard chemotherapy regimens, such as "CHOP" therapy (e.g., the use of combination of drugs such as Cyclophosphamide, Doxorubicin Hydrochloride, Oncavin [Vincristine] and Prednisone) for a variety of cancers. Related members of each family may be substituted for an individual component in this combination, and a subset of these agents may also be used. IGF1RK inhibitors of the invention can be administered simultaneously or sequentially with a variety of chemotherapeutic agents, including but not limited to methotrexate, cis-platin and 5-fluorouracil.

For example, IGF1RK inhibitors such as picropodophyllin analogues of the invention can be used in targeted therapy for the following cancers, either alone or in combination with any of the following drugs:

Breast—HERCEPTIN® and/or taxol, epithilone, letrozole (e.g., FEMARA®), anastrozole (e.g., ARIMIDEX), tamoxifen Ovarian—taxol Prostate—bicalutamide (e.g., Casodex)

Pancreatic—gemcitabine

Non-Hodgkins Lymphoma—RITUXAN®

Multiple Myeloma—bortezomide (e.g., VELCADE®)

Lung Cancer—topotecan (e.g., HYCAMTIN®), Etoposide, Tarceva (Genentech)

Testicular—etoposide (e.g., ETOPOPHOS®, VEPESID®)

Skin—imiquimod (e.g., Aldara)

Colorectal—capecitabine (e.g., XELODA®), irinotecan e.g., CAMPTO®), Epothilone

Myeloid Leukemia—GLEEVEC®

The invention will be further described by reference to the following examples. These examples should not be construed

6. EXAMPLE 1

Synthesis

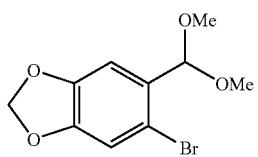

(1)

Bromoacetyl 1 was synthesized by bromination (Conrad, P. C. et al. *J. Org. Chem.*, 1987, 52, 586-591) and subsequent acetalization of piperonal (Keay, B. et al. *Can. J. Chem.* 1983, 61, 1987-1995.)

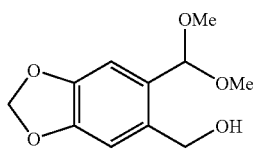

(2)

4-(Dimethoxy)methyl-5-hydroxymethyl(1,2-methylenedioxy)benzene (2)

To a solution of bromoacetal 1 (10.0 g, 36.3 mmol) in THF (100 mL) at −78° C. was added n-BuLi (25.0 mL, 40.6 mmol, 1.6 M in hexanes) dropwise via syringe. The solution was stirred for 1 h at 0° C. and a suspension of paraformaldehyde (3.30 g, 36.7 mmol) in THF (60 mL) was added via cannula. The reaction was warmed to room temperature, stirred for 2 h, and then quenched with $H_2O/Et_2O$. The aqueous layer was extracted with $Et_2O$, and the combined organics were dried ($MgSO_4$), filtered, and concentrated. Flash chromatography (50% EtOAc/hexanes) gave 2 (6.75 g, 82%). On a larger scale, 1 (50 g, 182 mmol) gave 2 in 72% yield (29.7 g). $^1$H NMR. (200 MHz, $C_6D_6$) δ 2.47 (t, J=6 Hz, 1H), 2.97 (s, 6H), 4.50 (d, J=6 Hz, 2H), 5.29 (s, 2H), 5.31 (s, 1H), 6.86 (s, 1H), 7.27 (s, 1H); $^{13}$C NMR. (125 MHz, $C_6D_6$) δ 52.8, 62.6, 101.6, 101.8, 108.4, 110.1, 130.4, 134.8, 147.5, 148.4; HRMS (EI) calculated for $C_{11}H_{14}O_5$ 226.0841, observed 226.0843. Anal. Calculated for $C_{11}H_{14}O_5$: C, 58.39; H, 6.24. Found: C, 58.20; H, 6.07.

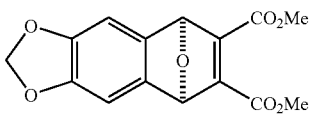

(3)

Dimethyl 1,4-Dihydro-1,4-epoxy-6,7-methylenedioxy-2,3-naphthalene-dicarboxylate (3)

The substrate 2 (23.7 g, 105 mmol) was dissolved in excess DMAD (251 g, 1.76 mol) and glacial AcOH (23.2 mL, 0.4 mol), and the mixture was stirred for 2 h at 80° C. Excess DMAD was removed by vacuum distillation, and flash chromatography (30% EtOAc/hexanes) gave 3 (56.4 g, 90%) as a yellow solid. On a smaller scale, 2 (5.53 g, 24.1 mmol) gave 3 in 92% yield (13.6 g): mp 117-119° C.; $^1$H NMR (300 MHz, $CDCl_3$) δ 3.79 (s, 6H), 5.86 (s, 2H), 5.90 (d, J=1 Hz, 1H), 5.95 (d, J=1 Hz, 1H), 6.95 (s, 2H); $^{13}$C NMR (125 MHz, $CDCl_3$) δ 53.0, 85.7, 102.2, 105.2, 141.4, 146.2, 152.5, 163.5. Anal. Calculated for $C_{15}H_{12}O_7$: C, 59.21; H, 3.98. Found: C, 59.27; H, 4.11.

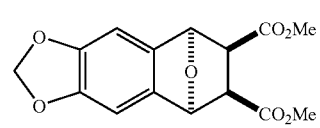

(4)

Dimethyl meso-(1R*,2S*,3R*,4S*)-1,4-Epoxy-6,7-methylenedioxy-1,2,3,4-tetrahydro-2,3naphthalene-dicarboxylate (4)

IBF Diels-Alder product 3 (43.2 g, 0.14 mol) was dissolved in EtOAc (300 mL), and 10% Pd/C (1.5 g) was added. The reaction mixture was hydrogenated at 48 psi for 6 h. The reaction mixture was filtered through Celite and concentrated to give 4 as a white solid: mp 96-99° C.; $^1$H NMR (300 MHz, $CDCl_3$) δ 3.53 (s, 6H), 3.61 (dd, J=2.3 Hz, 2H), 5.41 (dd, J=2.3 Hz, 2H), 5.92 (d, J=2 Hz, 1H), 5.96 (d, J=1 Hz, 1H), 6.82 (s, 2H); $^{13}$C NMR (125 MHz, $CDCl_3$) δ 48.3, 52.3, 81.5, 101.9, 103.9, 137.2, 147.5, 170.5. Anal. Calculated for $C_{15}H_{12}O_7$: C, 58.83; H, 4.61. Found: C, 58.90; H, 4.71.

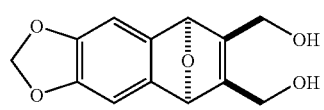

(5)

meso-(1R*,2R*,3S*,4S*)-2,3-Bis(hydroxymethyl)-1,4-epoxy-6,7-methylenedioxy-1,2,3,4tetrahydronaphthalene (5)

To a solution of the dimethyl ester 4 (25.0 g, 82 mmol) in $Et_2O$ (500 mL) at 0° C. was carefully added $LiAlH_4$ (6.2 g, 0.16 mol), and the resulting reaction mixture was refluxed for 1 day. Quenching was carried out by the sequential careful addition of $H_2O$ (6 mL; 30 min stirring), 15% NaOH (6 mL, 30 min stirring), and $H_2O$ (19 mL; 30 min stirring). The mixture was neutralized with 1 N HCl solution (100 mL), followed by the addition of $H_2O$ (2.5 L) and extraction with EtOAc (6.5 L). The organics were dried ($Na_2SO_4$) and concentrated to give 5 as a white solid (16.8 g, 82%): mp 177-179° C.; $^1$H NMR (500 MHz, $CD_3OD$) δ 2.65-2.68 (ddd, J=4,6,9 Hz, 2H), 2.77 (dd, J=9, 10 Hz, 2H), 3.15 (dd, J=6, 10 Hz, 2H), 5.24 (d, J=4 Hz, 2H), 5.90 (d, J=1 Hz, 1H), 5.94 (d, J=1 Hz, 1H), 6.85 (s, 2H); $^{13}$C NMR (125 MHz, $C_5D_5N$) δ 44.6, 60.1, 82.4, 101.6, 103.6, 138.2, 146.7. Anal. Calculated for $C_{13}H_{14}O_5$: C, 62.39; H, 5.64. Found: C, 62.26; H, 5.59.

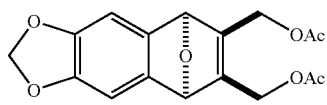

(6)

meso-(1R*,2R*,3S*,4S*)-2,3-Bis(acetoxymethyl)-1,4-epoxy-6,7-methylenedioxy-1,2,3,4tetrahydronaphthalene (6)

To a solution of 5 (57 g, 0.23 mol) and DMAP (1.4 g, 11.4 mmol) in pyridine (750 mL) at −10° c. Was added Ac₂O (69.9 g, 0.68 mol). The mixture was stirred for 16 h at room temperature and EtOAc was added. The organic phase was washed with saturated NaHCO₃ solution, 1 N HCl, and CuSO₄ (aqueous, saturated). Drying (MgSO₄) and concentration provided 6 (76 g, 100%): mp 120-122° C.; $^1$H NMR (300 MHz, CDCl₃) δ 2.05 (s, 6H), 2.82-2.85 (m, 2H), 3.24 (dd, J=10, 11 Hz, 2H), 3.75 (dd, J=6, 11 Hz, 2H), 5.26 (d, J=4 Hz, 2H), 5.94 (d, J=1 Hz, 1H), 5.99 (d, J=1Hz, 1H), 6.76 (s, 2H); $^{13}$C NMR (75 MHz, CDCl₃) δ 21.5, 40.6, 63.1, 82.2, 102.1, 103.8, 136.7, 147.6, 171.2; Anal. Calculated for C₁₇H₁₈O₇: C, 61.07; H, 5.43. Found: C, 61.20; H, 5.61.

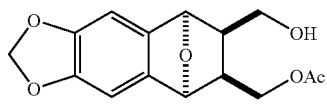

(7)

(1R,2R,3S,4S)-2-Acetoxymethyl-1,4-epoxy-3-hydroxymethyl-6 7-methylenedioxy-1,2,3,4tetrahydronaphthalene (7)

A 5 L RB flask was charged with PPL (263 g, crude, Sigma) and buffer solution (50 mM KPO₄, pH 7.8, 3.5 L). Diacetate 6 (20.0 g, 59.8 mmol) in DMSO (380 mL) was added via a sidearm while stirring with a mechanical stirrer. The reaction was quenched with 4 L of EtOAc after 2.5 h at room temperature. Following centrifugation to remove insoluble material, the organic layer was separated and washed with water. The organics were dried over MgSO₄ and concentrated. Flash chromatography (50-80% EtOAc/hexane) gave in the following order 6 (4.1 g, 21%); 7 [11.5 g, 66%; (83% based on recovered 6)], and diol 5 (0.7 g, 5%). The monoacetate 7 was determined to be 95% ee by examination of the $^1$H NMR spectrum of its derivative Mosher ester: mp 131-134° C.; $^1$H NMR (360 MHz, CDCl₃) δ1.43-1.58 (br. s, 1H), 2.06 (s, 3H), 2.77-2.84 (ddd, J=6, 9, 13 Hz, 2H), 2.87 (dd, J=9, 10 Hz, 1H), 3.23 (dd, J=10, 11 Hz, 1H), 3.28 (dd, J=6, 10 Hz, 1H), 3.76 (dd, J=6, 11 Hz, 1H), 5.25 (d, J=4 Hz, 1H), 5.32 (d, J=4 Hz, 1H), 5.94 (d, J=1 Hz, 1H), 5.98 (d, J=2 Hz, 1H), 6.75 (s, 1H), 6.83 (s, 1H); $^{13}$C NMR (75 MHz, CDCl₃) δ 21.5, 40.3, 43.8, 61.0, 63.4, 82.3, 82.4, 102.0, 103.7, 103.8, 136.7, 137.2, 147.3, 147.4, 171.5; [α]$^{24}$D=+52.6° (c 0.6, CHCl₃); HRMS (FAB, 3-NBA) calculated for C₁₅H₁₆O₆ 292.0947 [M+], observed 292.0952. Anal. Calculated for C₁₅H₁₆O₆: C, 61.64; H, 5.52. Found: C, 61.72; H, 5.65.

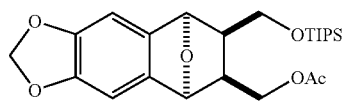

(8)

(1S,2S,3R,4R)-2-Acetoxymethyl-1,4-epoxy-6,7-methylenedioxy-3triisopropylsilyl-oxymethyl-1,2,3,4-tetrahydronaphthalene (8)

To a solution of 7 (14.5 g, 49.6 mmol) and imidazole (7.4 g, 0.11 mol) in DMF (150 mL) at 0° C. was added of TIPSCI (11.7 mL, 54.6 mmol) and the mixture was stirred for 7 h at room temperature. Et₂O was added and the mixture was washed with saturated aqueous NaHCO₃ and water. The organic phase was dried over MgSO₄, filtered and concentrated to give 7 as an oil (22.3 g, 100%). $^1$H NMR (300 MHz, CDCl₃) 0 1.03 (d, J=3 Hz, 18H), 1.03-1.22 (m, 3H), 2.06 (s, 3H), 2.76-2.77 (m, 3H), 3.14 (apt 1, J=10 Hz, 1H), 3.40-3.43 (m, 1H), 3.78 (dd, J=5, 11 Hz, 1H), 5.24 (d, J=4 Hz, 1H), 5.33 (d, J=3 Hz, 1H), 5.94 (d, J=1 Hz, 1H), 5.97 (d, J=1 Hz, 1H), 6.74 (s, 1H), 6.83 (s, 1H); $^{13}$C NMR (75 MHz, CDCl₃) δ 12.5, 18.6, 21.5, 40.2, 44.3, 61.8, 63.3, 82.3, 82.9, 101.8, 103.6, 104.1, 136.9, 137.5, 147.1, 147.2, 171.3; [α]$^{24}$D=+3.00 (c 0.9, CHCl); HRMS (FAB, 3-NBA, LiI) calculated for C₂₄H₃₆O₆SiLi 455.2442, observed 455.2443.

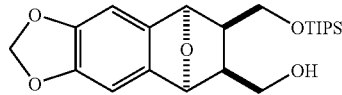

(9)

(1S,2S,3R,4R)-1,4-Epoxy-2-hydroxymethyl-6,7-methylenedioxy-3triisopropylsilyl-oxymethyl-1,2,3,4-tetrahydronaphthalene (9)

To a solution of acetate 8 (7.1 g, 15.8 mmol) in methanol (60 mL) was added K₂CO₃ (438 mg, 3.17 mmol). The resulting suspension was stirred for 1.5 h at room temperature, Dowex 50×8 resin (H⁺ form, 900 mg) was then added, and stirring was continued for 30 min. The solution was filtered, concentrated and the residue purified by flash chromatography (30% EtOAc in hexanes) to yield alcohol 9 (6.43 g, 100%). $^1$H NMR (300 MHz, CDCl₃) δ 0.98-1.07 (m, 21H), 2.79-2.85 (m, 2H), 2.97-3.11 (m, 2H), 3.17 (dd, J=5, 11 Hz, 1H), 3.31 (dd, J=6, 10 Hz, 1H), 5.19 (d, J=4 Hz, 1H), 5.20 (d, J=5 Hz, 1H), 5.96 (s, 2H), 6.73 (s, 1H), 6.76 (s, 1H); $^{13}$C NMR (75 MHz, CDCl₃) δ 12.4, 18.6, 44.4, 44.5, 61.1, 62.1, 82.0, 82.1, 101.9, 103.3, 103.4, 137.3, 137.6, 147.0, 147.1; IR (ATR) 3419 cm-1; [α]$^{24}$D=−26.8° (c 1.3, CHCl₃); HRMS (FAB, 3-NBA, LiI) calculated for C₂₂H₃₄O₅SiLi 413.2336, observed 413.2341.

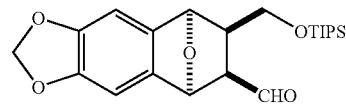

(10)

(1S,2R,3R,4R)-1,4-Epoxy-2-formyl-6,7-methylenedioxy-3-triisopropylsilyloxy-methyl-1,2,3,4-tetrahydronaphthalene (10)

To a solution of oxalyl chloride (29 mL of a 2.0 M solution in CH$_2$Cl$_2$, 58.1 mmol) at –78° C. was added a solution of DMSO (4.86 mL, 32.6 nmol) in CH$_2$Cl$_2$ (20 mL) via cannula. After 10 min of stirring at –78° C., a solution of 9 (13.9 g, 34.2 mmol) in CH$_2$Cl$_2$ (20 mL) was added dropwise via cannula. After an additional 30 min at –78° C., a solution of NEt$_3$ (16.2 mL, 116 mmol) in CH$_2$Cl$_2$ (14 mL) was added. The resulting reaction was allowed to warm to –40° C. and kept there for 2 h. EhO (500 mL) was then added at –40° C., and the reaction mixture was allowed to warm to room temperature. The mixture was washed with H$_2$O, aqueous NI—LiCl, and brine. The organics were dried (MgSO$_4$), filtered, and concentrated to give 10 (14.3 g, 100%). $^1$H NMR (300 MHz, CDCl$_3$) δ0.97-1.20 (m, 21H), 2.99-3.12 (m, 2H), 3.22 (ddd, J=3,5,8 Hz, 1H), 3.46-3.51 (m, 1H), 5.38 (s, 1H), 5.40 (s, 1H), 5.96 (d, J=1 Hz, 1H), 5.98 (d, J=1 Hz, 1H), 6.84 (s, 1H), 6.85 (s, 1H), 9.07 (d, J=3 Hz, 1H); $^{13}$C NMR (125 MHz, CDCl$_3$) δ 12.6, 18.6, 47.3, 54.2, 62.8, 81.0, 82.7, 102.0, 103.9, 104.0, 136.9, 137.5, 147.4, 147.5, 202.5; [α]$^{24}$D=–26.3° (c 0.8, CHCl$_3$); HRMS (FAB, 3-NBA, NaI) calculated for C$_{22}$H$_{32}$O$_5$SiNa 427.1917, observed 427.1925.

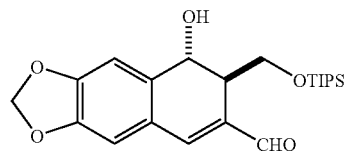

(11)

(3R,4R)-2-Formyl-4-hydroxy-6,7-(methylenedioxy)-3-triisopropylsilyloxymethyl-3,4-dihydronaphthalene (11)

To a solution of aldehyde 10 (10.5 g, 26.0 mmol) in MeOH (500 mL) was added NaOMe (1.40 g, 26 mmol) and the mixture was heated to reflux for 5 h. H$_2$O (245 mL) was then added, and CO$_2$ was bubbled through the solution until the pH reached 8 (pH paper). MeOH was removed in vacuo, and the resulting aqueous layer was extracted with CH$_2$Cl$_2$. The combined organics were dried (MgSO$_4$), filtered, and evaporated to provide 11 as a white solid (9.50 g, 90%): mp 87-89° C.; $^1$H NMR (500 MHz, CDCl$_3$) δ 0.93-1.03 (m, 21H), 1.74 (d, J=5 Hz, 1H), 3.17 (app t, J=10 Hz, 1H), 3.34 (ddd, J=2, 4, 6 Hz, 1H), 3.80 (dd, J=4, 10 Hz, 1H), 4.97 (app t, J=Hz, 1H), 6.01 (s, 1H), 6.02 (s, 1H), 6.83 (s, 1H), 6.93 (s, 1H), 7.24 (s, 1H), 9.61 (s, 1H); $^{13}$C NMR (125 MHz, CDCl$_3$) δ 12.5, 18.5, 43.4, 62.7, 70.0, 102.4, 109.8, 110.9, 125.3, 133.8, 136.0, 145.6, 148.8, 150.7, 192.9; IR (ATR) 3395, 1674, 1645 cm$^{-1}$; [α]$^{24}$D +82.0° (c 1.0, CHCl$_3$); HRMS (FAB, 3-NBA) calculated for C$_{22}$H$_{33}$O$_5$Si [(M+H)$^+$] 405.2097, observed 405.2096. Anal. Calculated for C$_{22}$H$_{32}$O$_5$Si: C, 65.31; H, 7.97. Found: C, 65.45; H, 7.98.

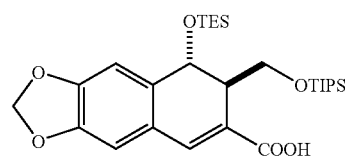

(12)

(3R,4R)-6,7-Methylenedioxy-4-triethylsilyloxy-3-triisopropylsilyloxymethyl-3,4-dihydronaphthalene-2-carboxylic acid (12)

To a solution of aldehyde 11 (900 mg, 2.25 mmol) in DMF (20 mL) was added TESCI (715 JtL, 3.38 mmol) and imidazole (460 mg, 6.75 mmol) at 0° C. and the reaction mixture was allowed to warm to r.t. overnight. Water was added and the product was extracted with Et20, the organic layer dried over MgSO$_4$ and evaporated. The residue was then dissolved in t-BuOH (40 mL) and 2-methyl-2-butene (12 mL). A solution of NaClO$_2$ (1.81 g, 20 mmol) and NaH$_2$PO$_4$ (1.93 g) in water (20 mL) was added and the mixture was stirred overnight. The product was extracted with Et$_2$O, dried over MgSO$_4$, concentrated and purified by silica gel column chromatography (10-30% EtOAc in hexanes) to give the acid 12 as a white powder (1.02 g, 85% over 2 steps). $^1$H NMR (400 MHz, CDCl$_3$) 00.65 (q, J=8.0 Hz, 6H), 0.94 (t, J=8.0 Hz, 9H), 1.06 (m, 21H), 3.05, (apt t, J=10 Hz, 1H), 3.34 (ddd, J=10.0, 4.5, 1.6 Hz, 1H), 3.77 (dd, J=10.0, 4.5 Hz, 1H), 5.03 (s, 1H), 6.03 (s, 2H), 6.81 (d, J=4.8 Hz, 2H), 7.67 (s, 1H).

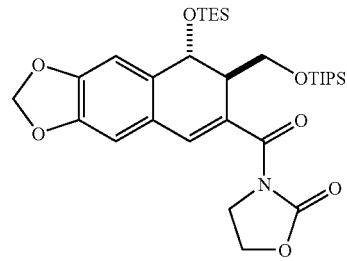

(13)

(3R,4R)-6,7-Methylenedioxy-2-(N-oxazolidinonyl)carbonyl-3-triisopropylsilyloxy-methyl-4-triethylsilyloxy-3,4-dihydronaphthalene (13)

To a solution of acid 12 (940 mg, 1.76 mmol) in THF (20 mL) at room temperature was added carbonyl diimidazole (428 mg, 2.64 mmol). The reaction mixture was stirred overnight, water was added and the product was extracted with Et$_2$O. The organic phase was dried over MgSO$_4$ and evaporated to provide the crude acyl imidazolide, which was used in the next step without further purification. To a deoxygenated solution of 2-oxazolidinone (306 mg, 3.52 mmol) in THF (10 mL) at 78° C. was added n-BuLi (1.65 mL of a 1.6 M solution in hexanes, 2.64 mmol). After 1 h, a solution of acylimidazolide (1.06 g, 1.76 mmol) in THF (8 mL) was added dropwise at –78° C. and the reaction mixture was allowed to stir for 5 h at this temperature. The reaction was quenched with water and extracted with Et$_2$O. The organic layer was dried (MgSO$_4$), concentrated and the residue purified by column chromatography on silica gel (hexanes/EtOAc/Et$_3$N, 90:10:05 to 70:30:0.5) to yield 13 (650 mg, 62%). $^1$H NMR (400

MHz, CDCl₃) J 0.65 (q, J=8.0 Hz, 6H), 0.94 (t, J=8.0 Hz, 9H), 1.03 (m, 21H), 3.17, (apt t, J=10 Hz, 1H), 3.38 (ddd, J=10.0, 6.0, 1.6 Hz, 1H), 3.71 (dd, J=10.0, 6.0 Hz, 1H), 4.00 (m, 1H), 4.16 (apt q, J=9.0 Hz, 1H), 4.49 (m, 2H), 4.99 (s, 1H), 6.00 (s, 1H), 6.74 (s, 1H), 6.79 (s, 1H), 7.13 (s, 1H); $^{13}$C NMR (100 MHz, CDCl₃) δ 5.0, 6.8, 11.9, 18.0, 44.1, 45.8, 61.8, 62.1, 68.5, 76.7, 77.1, 77.4, 101.4, 109.2, 110.3, 125.0, 126.3, 131.4, 137.2, 147.5, 148.8, 153.5, 169.7.

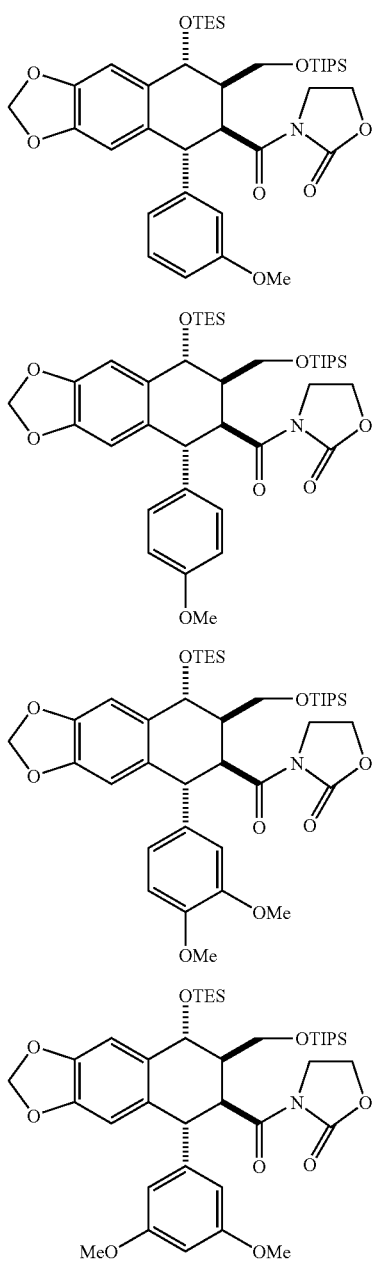

Typical Procedure for Introduction of E Rings (14-17)

To a suspension of CuCN (297 mg, 3.30 mmol) in THF (8 mL) at 5° C. was added 3.3 mL of a solution of the desired mono or di-methoxy phenylmagnesium bromide (1M in THF, 3.30 mmol). The resulting mixture was stirred for 30 min and a solution of Michael acceptor 13 (250 mg, 0.41 mmol) in THF (6 mL) was added dropwise at the same temperature. After 1.5 h at 5° C., a saturated aqueous solution of NH₄Cl was added and the product was extracted with Et₂O, the organic phase dried over MgSO₄ and evaporated. The product was filtered through a short silica gel column (hexanes/EtOAc 80:20) and used directly for the next step.

Typical Procedure for Desilylative Lactonization

To a solution of precursor 14-17 (0.21 mmol) in THF was added TBAF (1.0 M solution in THF, 4 eq.). The mixture was refluxed for 30 minutes and allowed to cool to r.t. A saturated solution of NH₄Cl was added and the product was extracted with Et₂O, the organic layer dried over MgSO₄ and evaporated. The crude product was purified by silica gel column chromatography (Hexanes/EtOAc, 7:3).

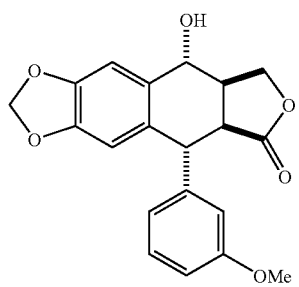

4',5'-Didemethoxy-(−)-picropodophyllin (18)

From Michael acceptor 13 (0.23 mmol, 140 mg) 55 mg of 18 (68% over 2 steps) were obtained as a white powder. $^1$H NMR (400 MHz, DMSO-d6) 02.50 (m, 1H), 3.38 (m hidden under water peak, 1H), 3.76 (s, 3H), 3.95 (d, J=7.2 Hz, 1H), 4.36 (dd, J=1004, 604 Hz, 1H), 4040 (dd, J=9.2, 604 Hz, 1H), 4049 (dd, J=9.2, 1.6 Hz, 1H), 5.92 (s, 2H), 5.94 (s, 1H), 5.97 (d, J=604 Hz, 1H), 6.84-6.89 (m, 3H), 7.07 (s, 1H), 7.32 (t, J=8.2 Hz, 1H); $^{13}$C NMR (100 MHz, DMSO-d6) δ 43.2, 4304, 44.3, 55.5, 67.7, 69.8, 101.2, 105.0, 107.7, 11204, 11504, 121.8, 130.1, 131.8, 135.3, 145.1, 146.2, 146.2, 159.9, 17804; HRMS (FAB, 3-NBA) calculated for C₂₀H₁₈O₆ 354.1103, observed 354.1100.

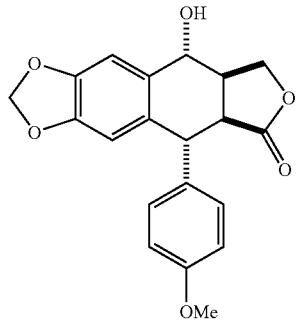

3',5'-Didemethoxy-(−)-picropodophyllin (19)

From Michael acceptor 13 (0.23 mmol, 139 mg) 50 mg of 19 (63% over 2 steps) were obtained as a white powder. $^1$H NMR (400 MHz, DMSO-d6) δ 2.49 (app. q, J=7.0 Hz, 1H), 3.29 (dd, J=9.6, 7.8 Hz, 1H), 3.78 (s, 3H), 3.92 (d, J=7.8 Hz, 1H), 4.36 (dd, J=10.0, 6.4 Hz, 1H), 4.39 (dd, J=9.2, 6.4 Hz, 1H), 4.49 (dd, J=9.2, 1.2 Hz, 1H), 5.91 (s, 2H), 5.92 (s, 1H), 5.95 (d, J=6.4 Hz, 1H), 6.96 (d, J=8.8 Hz, 1H), 7.06 (s, 1H), 7.19 (d, J=8.8 Hz, 1H); $^{13}$C NMR (100 MHz, DMSO-d6) δ 42.6, 43.3, 44.6, 55.5, 67.7, 69.7, 101.2, 104.9, 107.7, 114.4, 130.6, 132.4, 135.2, 135.4, 146.1, 146.1, 158.4, 178.5; HRMS (FAB, 3-NBA) calculated for $C_{20}H_{18}O_6$ 354.1103, observed 354.1113.

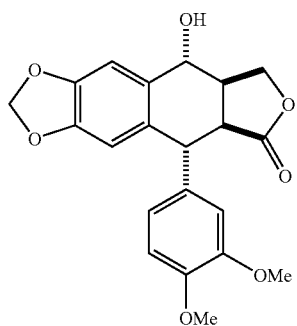

5'-Demethoxy-(−)-picropodophyllin (20)

From Michael acceptor 13 (0.26 mmol, 160 mg) 40 mg of 20 (41% over 2 steps) were obtained as a white powder. $^1$H NMR (400 MHz, DMSO-d6) δ 2.49 (m, 1H), 3.37 (dd, J=9.6, 8.0 Hz, 1H), 3.73 (s, 3H), 3.78 (s, 3H), 3.89 (d, J=8.0 Hz, 1H), 4.35 (dd, J=10.0, 6.4 Hz, 1H), 4.40 (dd, J=8.8, 6.4 Hz, 1H), 4.50 (d, J=8.8 Hz, 1H), 5.91 (d, J=2.0 Hz, 2H), 5.96 (s, 1H), 5.97 (d, J=5.6 Hz, 1H), 6.79 (d, J=8.0 Hz, 1H), 6.87 (s, 1H), 6.96 (d, J=8.0 Hz, 1H), 7.06 (s, 1H); $^{13}$C NMR (100 MHz, DMSO-d6) δ 43.1, 43.4, 44.3, 55.9, 67.7, 69.7, 101.1, 104.9, 107.7, 112.2, 113.0, 121.7, 132.4, 135.4, 135.5, 146.1, 146.1, 148.0, 149.2, 178.5; HRMS (FAB, 3-NBA) calculated for $C_{20}H_{18}O_6$ 384.1209, observed 384.1213.

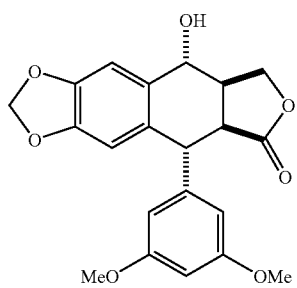

4'-Demethoxy-(−)-picropodophyllin (21)

From Michael acceptor 13 (0.25 mmol, 150 mg) 48 mg of 21 (50% over 2 steps) were obtained as a white powder. $^1$H NMR (400 MHz, DMSO-d6) δ 2.49 (m, 1H), 3.38 (dd, J=9.2, 8.0 Hz, 1H), 3.74 (s, 6H), 3.91 (d, J=7.2 Hz, 1H), 4.34 (dd, J=9.60, 6.4 Hz, 1H), 4.40 (dd, J=9.0, 6.4 Hz, 1H), 4.50 (d, J=9.0 Hz, 1H), 5.92 (s, 2H), 5.96 (d, J=6.0 Hz, 1H), 6.00 (s, 1H), 6.45 (s, 3H), 7.06 (s, 1H); $^{13}$C NMR (100 MHz, DMSO-d6) δ 43.1, 43.5, 44.1, 55.6, 67.7, 69.8, 98.8, 101.2, 105.0, 107.7, 131.6, 135.3, 145.8, 146.2, 161.0, 178.4; HRMS (FAB, 3NBA) calculated for $C_{20}H_{18}O_6$ 384.1209, observed 384.1221.

7. EXAMPLE 2

In Vitro Testing of Inhibition of Cell Growth

A murine breast cancer cell line derived from Kras* mice was used to assay the effect of IGF1RK inhibitors. Approximately 30,000 cells/well were plated in a 24-well plate which corresponds to 20% confluence. The next day (Day 0 for the experiment) two of wells were treated with MTT (Thiazol Blue Tetrazolium), a substrate used in a colorimetric metabolic assay that reflects cell density. The cells in the rest of the wells were treated with DMSO(PPP solvent), PPP or a derivative of PPP at 500 nM concentration. Forty-eight hours later the duplicate wells were assayed. The effectiveness of each of the PPP derivatives was compared with that of the original PPP.

The five compounds listed in Table 1 were tested. The results of the experiments with compounds 3 and 6 are shown in Table 2.

TABLE 1

| Entry | Compound |
|---|---|
| 1 (comparative) | (−)-picropodophyllin (PPP) |
| 2 (inventive) | (−)-picropodophyllin analogue with 3'-methoxy substitution on the E-ring (18) |
| 3 (inventive) | (−)-picropodophyllin analogue with 4'-methoxy substitution on the E-ring (19) |
| 4 (inventive) | (−)-picropodophyllin analogue with 3',4'-dimethoxy substitution on the E-ring (20) |
| 5 (inventive | (−)-picropodophyllin analogue with 3',5'-dimethoxy substitution on the E-ring (21) |

TABLE 2

| Kras* cells | Day 0 | Day 2 18 | Day 2 21 | Day 2 PPP | Day 2 No drug |
|---|---|---|---|---|---|
| 1 | 0.373 | 0.483 | 0.505 | 0.478 | 0.959 |
| 2 | 0.362 | 0.566 | 0.464 | 0.477 | 0.625 |
| Average | 0.3675 | 0.5245 | 0.4845 | 0.4775 | 0.792 |

Compound 18 appeared to be as effective as PPP at inhibiting growth of the Kras* breast cancer cell line. By varying the concentration of compound 18, we obtained a preliminary estimate of ~400 nM for $IC_{50}$ value, which very similar to the behavior seen with PPP itself on this test cell line. Moreover, the 4-methoxy compound (19) shows essentially no activity under exactly the same conditions. Such a dramatic SAR (Structure Activity Relationship) is quite remarkable.

8. EXAMPLE 3

In Vivo Testing

8.1. Materials and Methods

Mice

In addition to the mice conditionally expressing oncogenic Kras (for details see EXAMPLE 5, Materials and Methods), three mouse strains were used which have been described previously; two cre-expressing strains, Hs-cre1 and Wap$^{cre/+}$ (Dietrich P, et al., Mamm. Genome (2000), 11:196-205; Ludwig T, et al., Oncogene (2001), 20:3937-3948), and Igf1r$^{flox/flox}$ mice (Dietrich P, et al., Mamm. Genome (2000), 11:196-205). Molecular, histological, microarray and other analyses were performed as described in EXAMPLE 5, Materials and Methods and Table 9.

Drug Treatments

Details of the preclinical trial using picropodophyllin synthesized as described (Buchardt O, et al. *J. Pharm. Sci.* (1986), 75:1076-1080) and Erlotinib (purchased from Hwasun Biotechnology Co) are described in Results. The drugs were dissolved in DMSO and cremophor (9:1) and injected intraperitoneally. To calculate tumor volumes, the formula for a prolate spheroid ($\pi/6 \times a \times b2$ or $\sim a \times b2/2$, where a and b are the major and minor axis, respectively) was used. The lengths of axes were determined microscopically from sections of tumor nodules using a computer assisted morphometry system (SpotAdvanced VS. 4.0.1, Nikon Eclipse E400). For xenograft experiments, $5 \times 10^6$ MDA-MB-231 cells were injected bilaterally into the fat pads of mammary glands 3 and 4 of female SCID/NOD mice. At ten days post injection, when tumors were readily palpable, the mice were randomly divided into two groups of five mice each and received the same treatment (vehicle or PPP) described above for the Kras* mice for 3 weeks. For in vitro experiments, MDA-MB-231 cells were grown in DMEM supplemented with 10% fetal bovine serum. Equal numbers of cells were seeded in multiple wells of 24-well plates at low density ($\leq 20\%$ confluence at day 0) and either DMSO or PPP dissolved in DMSO was added to the medium (final concentrations: DMSO 01%, PPP 500 nM). Cell viability (duplicates) was measured on days 2, 4 and 6 by using the Thiazolyl Blue Tetrazolium Bromide (MTT) colorimetric assay (Mosmann T, *J. Immunol. Methods* (1983), 65:55-63).

8.2. Results and Discussion

Tumor Development in Mice Expressing Oncogenic Kras*

A suitable mouse model has been identified to evaluate Igf1r as a potential therapeutic target in the context of our research program aiming to generate mouse tumors by design using a variant of a genetic scheme involving cre/loxP recombination (Politi K, et al, *Oncogene* (2004), 23:1558-1565). Depending on the tissue-specificity of the promoter driving cre expression, tumors develop at chosen anatomical sites of progeny derived by mating Cre-producers with mice carrying a dormant oncogenic transgene that becomes functional after excision of a floxed DNA segment blocking its expression.

For development of a targeting cassette for high-level expression of any chosen cDNA introduced into a defined genomic site by knock-in, the Eef1a1 locus (encoding a translation elongation factor) was used as a recipient site for transgenic knock-in of various sequences, including a constitutively active oncogenic Kras cDNA [Kras 4B(G12D); Kras*]. Eef1a1 is strongly transcribed (Soares et al., *Proc. Natl. Acad. Sci. U.S.A.* (1994), 9, 9228-32) and yields an abundant protein product (~2% of the total cell protein; Codeelis, *Trends Biochem. Sci.* (1995), 20, 169-70). In the Eef1a1 targeting cassette (FIGS. 1A and 1B) which was used here, 5' and 3' regions of Eef1a1 gene homology are flanking a segment, eventually targeted into the first intron of the locus, which consists of a splice acceptor site, a floxed selectable marker associated with a "stop" sequence and a cDNA, for example Kras*, inserted into chosen restriction sites of a polylinker.

Ubiquitous activation of Kras* expression by removing the floxed block using a cre transgene transcribed in 2-cell stage embryos (Dietrich et al., *Mammalian Genome* (2000), 11: 196-205) caused embryonic lethality (not shown). On the other hand, crosses of Kras* mice with partners expressing Cre in particular tissues resulted in tumor development in the pancreas, prostate, skin, intestine and the hematopoietic system.

To activate expression of Kras* in mammary glands, a transgenic line (Ludwig et al., *Oncogene* (2001), 20, 3937-48) carrying cre inserted into the Wap locus, encoding a milk protein, which is specifically transcribed in alveolar and ductal mammary epithelial cells during late pregnancy and throughout lactation (Robinson et al., *Development* (1995), 121, 2079-90) was used. Unexpectedly, lactating females with an Eef1a1-Kras*/Wap$^{cre}$e genotype (n=28) developed palpable multifocal, fully invasive tumors extremely rapidly. Specifically, these malignant breast carcinomas appeared within a period of 2 days to ~2 months after the first delivery of pups with a median time of tumor-free survival ($T_{50}$) of only 9 days (FIG. 1D). This is believed to be the first description of a mouse model in which a malignant neoplasm is induced by a single tumorigenic stimulus in one step without a requirement for secondary oncogenic events, as evidenced by the rapidity of tumor development. This surprising observation of apparently single-step tumorigenesis can be attributed to Kras* overexpression at a very high level ($23.5 \pm 5.8$-fold higher than that of endogenous Kras mRNA, n=4; see an example of Northern analysis in FIG. 1C). However, Western analysis indicated that the amount of total Kras (including the mutant protein form) was only moderately elevated in the neoplastic tissue in comparison with the wild-type (~4-fold; FIG. 1C). Whether this is caused by poor translatability or rapid turnover of the fusion Eef1a1/Kras* transcript or some other posttranscriptional mechanism remains unclear.

Histopathological Analysis of Kras*-induced Mammary Carcinomas (see FIG. 2)

Female mice developing tumors were sacrificed when moribund within a period of 9 days to ~3 months (this brief time of observation only rarely permitted the detection of lung metastases). In all examined cases (n=37), the Kras*-induced carcinomas involved most or all mammary glands and were either multifocal or consisted of large masses generated by coalescence of smaller components. The tumors were histologically heterogeneous and four coexistent types of invasive carcinomas were identified at variable proportions: adenocarcinomas (Dunn Type A/B tumors), and pale, squamous and spindle cell (sarcomatous) carcinomas [PCC, SCC and SRC; FIG. 2A; the features of cancer forms are summarized in EXAMPLE 5, Table 3].

Overall, however, the slow-growing adenocarcinomas, which exhibited a very low proliferation index (~10-20% of the corresponding value for any other component), were on average the smallest tumor constituent (14% of the total tumor mass; ~40-50% of the size of any other form; Table 3).

TABLE 3

| Histopathological Analysis of Mammary Carcinomas | | | | |
|---|---|---|---|---|
| | Adenocarcinoma (Dunn A/B) | Pale Cell Carcinoma$^a$ | Squamous Cell Carcinoma | Spindle Cell Carcinoma |
| A. Kras* Tumors | | | | |
| Component size (%) | $14.0 \pm 2.2$ (n = 37) | $24.7 \pm 5.1$ (n = 37) | $37.2 \pm 4.7$ (n = 37) | $24.7 \pm 4.5$ (n = 37) |
| Proliferation index (%) | $4.4 \pm 0.6$ (n = 10) | $46.7 \pm 2.3$ (n = 10) | $22.1 \pm 1.5$ (n = 8) | $23.0 \pm 5.6$ (n = 6) |

TABLE 3-continued

Histopathological Analysis of Mammary Carcinomas

|  | Adenocarcinoma (Dunn A/B) | Pale Cell Carcinoma[a] | Squamous Cell Carcinoma | Spindle Cell Carcinoma |
|---|---|---|---|---|
| Morphology | Well-differentiated microacinar structures resembling budding alveoli and consisting of small, uniform-size cells with small, round, hyperchromatic nuclei (Dunn Type A). Occasionally, solid cords, nests or trabeculae without glandular differentiation are detected (Dunn B). | Solid nests of large pleomorphic cells with some (usually small) degree of keratinization, which possess lightly staining ("pale") cytoplasm and nuclei. The pale cells are sometimes associated with small basophilic cells with scant cytoplasm and ovoid nuclei. | Irregular nests of flattened eosinophilic cells of variable size that exhibit distinct cell borders and clear evidence of keratinization (squamous metaplasia). These nests are commonly separated by broad bands of tumor stroma and surrounded by inflammatory infiltrate. | Fascicles of spindle-shaped cells with elongated large nuclei exhibiting infiltrative growth (there are no defined borders with the adjacent non-neoplastic tissue; sarcomatous metaplasia). |
| B. Kras* Tumors After Conditional Ablation of Igf1r | | | | |
| Component size (%) | 43.4 ± 5.5 (n = 9) | 15.9 ± 6.9 (n = 9) | 19.4 ± 8.3 (n = 9) | 21.4 ± 6.6 (n = 9) |
| Proliferation index (%) | 3.8 ± 0.4 (n = 9) | 49.4 ± 3.0 (n = 8) | 18.4 ± 6.4 (n = 3) | 24.0 ± 2.9 (n = 4) |

[a]It was observed that this form of carcinoma was histologically indistinguishable from a rare tumor type that appears specifically in the GR mouse strain carrying an active endogenous MMTV provirus (Mtv2) on chromosome 18 (van Nie R and Dux A, *J. Natl. Cancer Inst.* (1971), 46: 885-897; Strum JM *Am. J. Pathol.* (1981) 103: 283-291), but differed in immunophenotype (not shown).

The Dunn adenocarcinomas were well-differentiated microacinar structures (Dunn Type A) or occasionally solid nests without glandular differentiation (Dunn Type B) and corresponded morphologically to tumor types induced by the mouse mammary tumor virus (MMTV; Hoeber-Harper, New York), (1959) pp. 38-84; Sass B and Dunn T B, *J Natl Cancer Inst* (1979); 62:1287-1293). On average, they were the smallest and slowest-growing tumor constituents (Table 3). The PCC, which consisted of large, lightly-staining ("pale") cells, were also adenocarcinomas, but exhibited in some areas signs of keratinization. Morphologically, they are indistinguishable from a rare tumor type that appears specifically in the GR strain of mice carrying an active endogenous MMTV provirus (Mtv2) on chromosome 18. However, immunophenotypic differences between the Kras*- and MMTV-induced PCC were identified. Clear evidence of keratinization (squamous metaplasia) was seen in SCC, whereas the spindle-cell tumors exhibited sarcomatous metaplasia. The microacinar (Dunn A), pale and squamous cell tumors were correlated with the presence of corresponding forms of carcinoma in situ (CIS; also referred to in mice as "mammary intraepithelial neoplasm", MIN; Cardiff R D et al., *The Mouse in Biomedical Research. Volume II. Diseases*, Second ed., eds. Fox J G et al., (Elsevier, New York), (2007), pp. 581-622; FIG. 2A, insets). Because the squamous CIS was rarely observed, we surmise that it gives rise to invasive SCC very rapidly. A distinct spindle-cell CIS was not found, but occasionally squamous CIS exhibiting foci of sarcomatous metaplasia could be recognized.

One type of carcinoma in situ (small-cell, low nuclear grade CIS) exhibited a pattern similar to that of lobular neoplasia in human CIS. It was composed of small cells filling lobules, but never extralobular ducts, and could be discriminated from the cytologically and immunophenotypically identical invasive microacinar carcinoma solely on the basis of preservation of a myoepithelial layer. A second CIS type, also retaining a discontinuous layer of myoepithelial (p63-positive) cells, formed multiple cellular layers in ducts, and was also present in lobuloalveolar units, where it filled alveolar spaces in the form of solid nests or nodules. This high-grade CIS was found either in isolation or adjacent to an invasive component and consisted of large cells indistinguishable in appearance and immunostaining characteristics from those seen in PCC. Interestingly, in several independent cases, conglomerates of large ductal CIS cells were observed budding from a suprabasal location outward to acquire a position between the (still intact) luminal epithelial layer and the overlying myoepithelial layer (at least in the human mammary epithelium, multilineage progenitor cells are thought to reside in a suprabasal position). A third type of CIS was composed of squamous cells and was the only one exhibiting foci of sarcomatous metaplasia. Apparently, this CIS was giving rise to invasive squamous cell carcinoma quite early, as it was observed less frequently than the other forms.

To assess the origin, relationships and signaling characteristics of the carcinomas by immunophenotyping, an extensive panel of markers was used (FIG. 2A, Table 4 and FIG. 6). The results indicated that the $ER^+/PR^+$ Dunn adenocarcinomas, which express exclusively luminal cell markers, such as cytokeratin 18 (CK18; Krt18), are luminal-type cancers presumably derived from differentiated luminal epithelial cells. In contrast, on the basis of their distinct features, the pale, squamous and sarcomatous carcinomas appear to correspond to basal-like breast carcinomas.

TABLE 4

Immunophenotyping Data[a]

|  | Normal | | | | | CIS | | | Carcinoma | | | |
|---|---|---|---|---|---|---|---|---|---|---|---|---|
|  | V | P | L | I | PI | Small Cell | Large Cell | Sq. Cell | Dunn A/B | PCC | SCC | SRC |
| Luminal markers | | | | | | | | | | | | |
| Ck18 (Krt18) | +++ | +++ | +++ | +++ | +++ | +++ | ++ | + | +++ | ++ | ++ | ++ |
| ER | ND | ND | ND | ND | ND | ++ | + | − | ++ | − | − | − |

TABLE 4-continued

Immunophenotyping Data[a]

|  | Normal | | | | | CIS | | | Carcinoma | | | |
| --- | --- | --- | --- | --- | --- | --- | --- | --- | --- | --- | --- | --- |
|  | V | P | L | I | PI | Small Cell | Large Cell | Sq. Cell | Dunn A/B | PCC | SCC | SRC |
| PR | ND | ND | ND | ND | ND | ++ | +/− | − | ++ | − | − | − |
| GATA3 | +++ | +++ | +++ | +++ | +++ | +++ | ++ | − | +++ | ++ | − | − |
| Basal markers | | | | | | | | | | | | |
| Ck5 (Krt5) | +++ | +++ | +++ | +++ | +++ | − | +/− | +++ | − | ++ | +++ | ++ |
| Ck14 (Krt14) | +++ | +++ | +++ | +++ | +++ | − | ++ | +++ | − | ++ | +++ | +++ |
| SMA (Actg2) | +++ | +++ | +++ | +++ | +++ | − | − | − | − | − | +/− | +/− |
| p63 (Trp63) | +++ | +++ | +++ | +++ | +++ | − | + | +++ | − | + | +++ | − |
| "Stem Cell" markers | | | | | | | | | | | | |
| Itga6 | ++ | +/− | +/− | +/− | ++ | − | +/− | ++ | − | +/− | ++ | − |
| Itgb1 | ND | ND | ND | ND | +++ | ND | ND | ND | ++ | +++ | +++ | ++ |
| CD24 | ND | ND | ND | ND | + | ND | ND | ND | ++ | + | + | +/− |
| Ck6 (Krt6) | ++ | +/− | +/− | +/− | ++ | − | ++ | +++ | − | ++ | +++ | +/− |
| Nestin | +/− | +/− | − | +/− | − | − | +++ | + | − | +++ | + | ++ |
| Annexin VIII | − | +/− | − | +/− | ++ | − | +/− | +++ | − | +/++ | +++ | +/− |
| Sca1 | +/− | +/− | − | +/− | +/− | − | ++ |  | − | ++ | +++ | − |
| Signaling markers | | | | | | | | | | | | |
| pErk | +/− | ++ | − | − | − | ++ | +++ | ++ | ++ | +++ | +++ | +++ |
| pAkt1 | + | ++ | − | + | +/− | − | +++ | +++ | − | +++ | ++ | ++ |
| pS6 | + | +++ | − | ++ | +/− | − | +++ | +++ | − | +++ | +++ | + |
| Igf1r | +/− | + | + | +/− | − | ++ | +++ | ++ | ++ | +++ | ++ | +/− |
| Igf1 | +/− | − | + | − | − | − | − | − | − | − | − | − |
| Igf2 | − | − | − | − | − | − | − | − | − | − | − | − |
| Egfr | ++ | + | + | + | ++ | + | +++ | +++ | + | ++ | +++ | − |
| Erbb2 (Neu) | + | + | +/− | + | + | + | + | + | + | ++ | + | − |
| Erbb3 | − | − | − | − | − | + | +++ | +++ | + | ++ | +++ | +++ |
| Notch 1 | ++ | ++ | +++ | +/++ | +/− | + | +++ | ++ | + | +++ | ++ | + |
| Jagged |  |  |  |  |  | − | +++ | +++ | − | +++ | +++ | +++ |
| Myc | ++ | +++ | − | ++ | + | − | +++ | ++ | − | +++ | ++ | +++ |
| Fosl 1 | + | + | + | + | + | − | − | +++ | − | +/− | +++ | +++ |
| Other markers | | | | | | | | | | | | |
| E-cadherin | +++ | +++ | +++ | +++ | +++ | +++ | +++ | +++ | +++ | +++ | +++ | − |
| Vimentin | − | − | − | − | − | − | + | − | − | +/− | − | +++ |
| β-catenin (nuclear) | − | − | − | − | − | − | − | − | − | −/++ | − | − |
| β-catenin (cell surface) | +++ | +++ | +++ | +++ | +++ | +++ | +++ | +++ | +++ | ++ | +++ | − |

[a]The intensity of marker immunostaining signal (−: absent; +: weak in >15% of the cells; ++: focally strong; +++: generally strong) is compared between wild-type mammary glands of virgin (V), pregnant (P), lactating (L), involuting (I) and postinvolutional (PI) female mice and in situ or invasive carcinomas.

The results indicated that the cancer forms induced by Kras* could be classified into two groups differing in the cell-of-origin. Whereas expression of exclusively luminal epithelial cell markers (such as keratin 18; Krt18) was detected in small-cell CIS and Dunn A/B adenocarcinomas, the large-cell CIS and the pale, squamous and sarcomatous carcinomas exhibited positive immunostaining both for luminal markers (Krt18) and for basal cell markers (Krt5, Krt14, p63), and also for presumptive stem cell markers. Apparently, the Dunn adenocarcinomas, which are also hormone receptor-positive (ER+/PR+), are luminal-type neoplasms, presumably derived from differentiated luminal epithelial cells, whereas the ER−/PR− pale, squamous and sarcomatous tumors are basal-like cancers derived from undifferentiated, bipotential precursor cells and not from myoepithelial cells, as they do not co-express p63 and smooth muscle actin (SMA), which are the functional markers of myoepithelial differentiation. This interpretation is also strongly supported by expression profiling data.

On the other hand, a potential relationship between the three basal forms is not a straightforward issue. For example, it was considered that the PCC and the metaplastic and more extensively keratinized squamous cell carcinomas (SCC), which are often found intimately interspersed, might be related and could represent two extreme forms of a spectrum of adenosquamous carcinomas. However, it may be more likely that these two tumor forms originate from different cell precursors, as suggested from the identification of distinct CISs and the results of immunophenotyping. In regard to the spindle-cell (sarcomatous) carcinomas (SRC), it is important to note that they have lost the epithelial marker E-cadherin, which is present in PCC and SCC, but strongly express vimentin, a mesenchymal cell marker. Nevertheless, as in other cases of histopathologically heterogeneous mammary tumors, the SRC presumably are epithelial and not mesenchymal tumors that could be derived from an adenosquamous component by EMT (epithelial-mesenchymal transition).

The term "precursor cell" is used herein to refer to the cell-of-origin of the basal-like carcinomas that have been identified in these experiments. It is notable that the PCC expresses Gata3, a luminal cell marker for mature mammary epithelium, which is absent from SCC. This difference may by indicative of distinct cells of origin, but it cannot be interpreted as suggesting that PCC could be derived from terminally differentiated luminal cells, as Gata3 is expressed in precursor cells of mammary primordia. Differences in the expression of particular markers, such as CK5/14 and p63, also exist between SRC and the other two basal-like components (PCC and SCC). Nevertheless, the overall similarities between the three basal forms, including the expression of putative stem cell markers and particular signaling components validated by molecular data, permit a clear-cut demarcation from the luminal Dunn adenocarcinomas.

"Stem cell markers" should not be confused with "markers of stemness", i.e. cellular constituents that bestow stem cell behavior (self-renewal capacity and potential to generate differentiated derivatives) and/or are uniquely expressed in stem cells. In fact, with the apparent exception of the Lgr5 gene, markers of sternness are generally unavailable. Instead, "stem cell markers" correspond to an "expression signature" (i.e. a combinatorial, rather than exclusive expression of some set of cellular elements) capable of discriminating a cell population enriched in operationally defined stem cells. Analysis of the distribution of the CD29 (integrin β1; Itgb1) and CD49f (integrin α6; Itga6) by using double immunofluorescence showed that both of these markers were co-localized in the basement membrane of the myoepithelial layer while, in addition, Itgb1 was present in the basolateral, but not the luminal aspect of luminal cells. This distribution was maintained in microacinar adenocarcinomas, but only for Itgb1, whereas the basal-like forms had altered patterns. Thus, all SCC cells exhibited intense labeling for both markers co-localized circumferentially, while the intensity of signal in PCC and SRC was variable and did not involve all cells. An additional marker that was examined was Sca1, which was found to be present in PCC and SCC, but not in SRC or Dunn tumors.

Of the three major molecularly classified subtypes of human breast cancer (Perou C M, et al. *Nature* (2000), 406: 747-752; Sorlie T, et al. *Proc Natl Acad Sci USA* (2001), 98:10869-10874; Sorlie T, et al. *Proc Natl Acad Sci USA* (2003), 100:8418-8423), luminal cancers are estrogen receptor-positive (ER$^+$), whereas the other two classes are ER-negative and either overexpress ERBB2 (ERBB2$^+$) or exhibit phenotypic features of basal/myoepithelial cells (basal-like cancers). The latter also lack progesterone receptor (PR) and ERBB2 ("triple negative breast cancers"; see Da Silva L, et al., *J. Clin. Pathol*. (2007), 60: 1328-1332; Reis-Filho J S and Tutt A N, *Histopathology* (2008), 52:108-118), but frequently express EGFR and basal markers, such as cytokeratins (CK) 5/6 and/or 14 and p63 (Nielsen T O, et al., *Clin. Cancer Res*. (2004), 10:5367-5374.). The basal-like group (15-20% of all breast cancers), which is quite heterogeneous, includes high proportions of BRCA1-associated and also medullary and metaplastic (squamous, spindlecell and other) subtypes. Interestingly, KRAS amplification was detected in 56% (9/16) of examined basallike human breast cancers (Herschkowitz J. et al., *Genome Biol*. (2007), 8:R76).

On the basis of their distinct features, the Kras*-induced ER$^-$/PR$^-$ pale, squamous and sarcomatous mouse carcinomas, which are immunopositive for both luminal (CK18) and basal cell markers (CK5, CK14, p63, and rarely smooth muscle actin), and also for presumptive stem-cell markers (Table 4), are analogous to some of the forms of human basal-like cancers. It is likely that these basal-like murine tumors are derived from undifferentiated, bipotential precursor cells and not from myoepithelial cells (this hypothesis concerning "cells-of-origin" is discussed in detail in EXAMPLE 5). Consistent with this view is the fact that the Kras* activating cre is embedded in the Wap locus that is not expressed in fully differentiated myopithelial cells.

A morphological similarity between mouse pale cell carcinoma and a type of human basal-like breast cancer that was also correlated with KRAS copy gain, was observed. In a collection of human breast cancer specimens (n=94), 17 samples (18%) were found to be basal-like (triple-negative and positive for CK5/6), while 77 (82%) were non-basal (R. Parsons and H. H., unpublished). Analysis of the 17 basal cancers for amplification of the KRAS locus by using CGH showed that 5 of the specimens scored positive, while further analysis of a subset by using FISH identified a sixth positive sample. The corresponding KRAS amplification frequency in the non-basal samples detected by CGH was 4/77 (~5% vs. ~35%, 6/17; P=0.002, Fisher's exact test). Three of the basal-like specimens with amplified KRAS displayed medullary features (large tumor nodules with pushing, rather than infiltrative borders, composed of large cells with irregular, sometimes bizarre nuclei growing in a syncytial fashion) but none of them met all of the criteria for classical medullary carcinoma classification (they are referred to here as "atypical medullary breast cancer", AMBC; Fadare O and Tavassoli F A, *Adv. Anat. Pathol*. (2007), 14:358-373). Interestingly, two of these AMBCs, contained abundant large cells with pale or clear cytoplasm and exhibited a strong resemblance to the histomorphological signature of the PCC observed in our mouse model. To validate this correlation, an available set of triple-negative AMBCs (n=8) was examined and it was observed that most of them (7/8) were at least focally comparable to the PCC in Kras* mice (FIG. 2B). Immuno-histochemical analysis showed that all 8 of these AMBCs were positive for basal cytokeratins 5 and 14 and showed IGF1R staining along their cellular surface (FIG. 2B). FISH analysis was performed to assess potential amplification of the KRAS locus and found that 3 of these cancers, all of which possessed as a major component large pale cells, tested positive (FIG. 2C; P=0.015; using the data 3/8 for basal and 4/77 for non-basal specimens). Therefore, the results showed that a subset of basal-like human breast cancers preferentially exhibit amplification of the KRAS locus frequently associated with a pale cell carcinoma character.

Molecular Analysis of Kras*-induced Mammary Carcinomas

To complement the morphological information described above, the expression profiles of normal postinvolutional mammary glands (n=5) and Kras*-induced carcinomas (n=14) were examined by microarray analysis, and it was found that they were readily discriminated by unsupervised hierarchical clustering (FIG. 7). Although the dendrogram also stratified the tumors according to the predominating basal-like component, only average differential expression levels in tumors vs. normal glands was compared to simplify the analysis (the microarray data were validated in part by immunohistochemistry and Northern or Western blotting).

Comparisons of the profiling results with lists of basal and luminal markers chosen for classification of human breast cancers (Sorlie et al., *BMC Genomics* (2006), 7:127; Herschkowitz et al., *Genome Biol*. (2007), 8, R76) and also with datasets of upregulated and downregulated genes in basal and non-basal breast cancers (Farmer et al., *Oncogene* (2005), 24, 4660-71; Richardson et al, *Cancer Cell* (2006), 9, 121-32) showed unequivocally that the Kras*-induced tumors are basal-like carcinomas, in agreement with the histological evidence. In fact, the null hypothesis that there is no statistical difference in the representation of basal and luminal markers in the groups of upregulated and downregulated genes in Kras* tumors was overwhelmingly rejected (Table 5). In addition, consistent with the hypothesis that the basal-like Kras* cancers evolve from precursor cells of the mammary epithelium, the data showed that the pattern of overexpressed genes in the tumors resembled much more the profile of a mammary cell population enriched in stem cells than that of another population consisting predominantly of luminal cells (Stingl et al., *Nature* (2006), 439, 993-97; high statistical significance; Table 5). Not unexpectedly, there was a high degree of similarity between the profiles of Kras*-induced mouse lung (Sweet-Cordero et al., *Nature Genet*. (2005), 37, 48-55) and mammary tumors (Table 5). Finally, comparisons of the microarray results with those for other mouse mammary tumors supported strongly the view that Kras* deregulates to a much larger extent all major signaling pathways (Tables 6-8).

TABLE 5

Expression profiling data

| Comparison Datasets (D) | Markers (total #) | Markers in the Profile of Kras*-induced Mammary Cancers Represented in the Comparison Datasets | | | | | |
|---|---|---|---|---|---|---|---|
| | | Upregulated (3154 total) | | | Downregulated (2092 total) | | |
| | | Markers in Common (#) | % | P | Markers in Common (#) | % | P |
| Human Breast Cancer | | | | | | | |
| D1a: Basal Markers | 317 | 101 | 31.9 | $<10^{-6}$ | 37 | 11.7 | 0.01 |
| D1b: Luminal Markers | 263 | 38 | 14.4 | | 47 | 17.9 | |
| D2a: Basal Markers | 150 | 41 | 27.3 | 0.002 | 15 | 10.0 | 0.02 |
| D2b: Luminal Markers | 105 | 13 | 12.4 | | 20 | 19.0 | |
| D3a: Upregulated in Basal-like Cancers | 1341 | 453 | 33.8 | $<10^{-5}$ | 154 | 11.5 | $2 \times 10^{-5}$ |
| D3b: Downregulated in Basal-like Cancers | 1520 | 327 | 21.5 | | 263 | 17.3 | |
| D4a: Upregulated in Basal-like Cancers | 1191 | 362 | 30.4 | 0.007 | 131 | 11.0 | $10^{-4}$ |
| D4b: Downregulated in Basal-like Cancers | 858 | 229 | 26.7 | | 140 | 16.3 | |
| Mouse Mammary Cells | | | | | | | |
| D5a: "Stem Cell" Markers | 243 | 119 | 49.0 | $3 \times 10^{-5}$ | 35 | 14.4 | 0.015 |
| D5b: Luminal Markers | 222 | 64 | 28.8 | | 47 | 21.2 | |
| Kras*-Dependent Expression | | | | | | | |
| D6a: Upregulated in Mouse Lung Cancer | 487 | 183 | 37.6 | $<10^{-6}$ | 54 | 11.1 | $<10^{-6}$ |
| D6b: Downregulated in Mouse Lung Cancer | 439 | 92 | 21.0 | | 164 | 37.4 | |

[a]Markers of the indicated datasets D1-D6 (filtered as described in EXAMPLE 5 Methods) are from Sorlie T, et al. *BMC Genomics* (2006) 7: 127; Herschkowitz J., et al. *Genome Biol* (2007), 8: R76; Farmer P, et al. *Oncogene* (2005), 24: 4660-4671; Richardson AL, et al. *Cancer Cell* (2006), 9: 121-132; Stingl J, et al. *Nature* (2006), 439: 993-997; Sweet-Cordero A, et al. *Nat Genet* (2005), 37: 48-55. For sets D3 and D4, we used the meta-analysis data of the Oncomine database (www.oncomine.org).

TABLE 6

Expression of signaling pathway components in mouse mammary tumors[a]

| Pathway | Kras* | | | Neu | | | Myc | | | Tag | | | DMBA | | |
|---|---|---|---|---|---|---|---|---|---|---|---|---|---|---|---|
| | # Total A | # | % | # Total B | # | % | P | # | % | P | # | % | P | # | % | P |
| Mapk | 162 | 35 | 21.6 | 140 | 14 | 10.0 | 0.003 | 8 | 5.7 | $4 \times 10^{-5}$ | 13 | 9.3 | 0.02 | 13 | 9.3 | 0.002 |
| Pi3k | 66 | 19 | 28.8 | 62 | 9 | 14.5 | 0.025 | 4 | 6.5 | $7 \times 10^{-4}$ | 3 | 4.8 | 0.0002 | 3 | 4.8 | 0.0002 |
| mTOR | 20 | 10 | 50.0 | 19 | 2 | 10.5 | 0.008 | 6 | 31.6 | NS | 1 | 5.3 | 0.002 | 3 | 15.8 | 0.02 |
| Erbb | 25 | 13 | 52.0 | 20 | 3 | 15.0 | 0.009 | 0 | 0 | $7 \times 10^{-5}$ | 1 | 5.0 | 0.0006 | 1 | 5.0 | 0.0006 |
| Wnt | 85 | 26 | 30.6 | 74 | 1 | 1.4 | $>10^{-5}$ | 3 | 4.1 | $6 \times 10^{-6}$ | 7 | 9.5 | 0.0006 | 8 | 10.8 | 0.001 |
| Notch | 42 | 15 | 35.7 | 37 | 1 | 2.7 | 0.0002 | 3 | 8.1 | 0.003 | 2 | 5.4 | 0.0008 | 2 | 5.4 | 0.0008 |
| Tgfb | 61 | 23 | 37.7 | 48 | 4 | 8.3 | 0.0002 | 2 | 4.2 | $2 \times 10^{-5}$ | 4 | 8.3 | 0.0003 | 4 | 8.3 | 0.0003 |
| Jak/Stat | 111 | 22 | 19.8 | 89 | 6 | 6.7 | 0.0045 | 2 | 2.2 | $6 \times 10^{-5}$ | 4 | 4.5 | 0.0008 | 2 | 2.2 | $6 \times 10^{-5}$ |
| Hedgehog | 19 | 7 | 36.8 | 19 | 0 | 0 | 0.004 | 1 | 5.3 | 0.02 | 0 | 0 | 0.004 | 0 | 0 | 0.004 |
| Vegf | 10 | 4 | 40.0 | 10 | 1 | 10.0 | NS | 0 | 0 | 0.04 | 2 | 20.0 | NS | 1 | 10.0 | NS |
| Cell Cycle | 88 | 48 | 54.5 | 82 | 19 | 23.2 | $2 \times 10^{-5}$ | 32 | 39.0 | 0.02 | 41 | 50.0 | NS | 25 | 30.5 | 0.0008 |
| Apoptosis | 61 | 18 | 29.5 | 56 | 5 | 8.9 | 0.0035 | 4 | 7.1 | 0.001 | 4 | 7.1 | 0.001 | 1 | 1.8 | $2 \times 10^{-5}$ |
| >1 Pathway | 43 | 16 | 37.2 | 39 | 4 | 10.3 | 0.0035 | 3 | 7.7 | 0.001 | 5 | 12.8 | 0.008 | 1 | 2.6 | $6 \times 10^{-5}$ |

[a]Only upregulated genes are considered (see Table 9 for a list of genes encoding signaling components that are upregulated in carcinomas induced by Kras*). The total number (#) of unique components in each major signaling pathway (listed in Table 8) is shown in column A, except for the last row (components participating in more than one pathway). The number of a pathway components that are overexpressed in Kras*-induced cancers are compared with the corresponding numbers reported (Herschkowitz, J. I. et al. *Genome Biol* (2007), 8: R76) for two luminal type mammary tumors induced by Neu (Erbb2) or Myc, a basal-like cancer induced by DMBA administration and a tumor with mixed basal and mesenchymal characteristics induced by Tag (SV40 large T antigen). For the reported cases, the total number of components (column B) is less than that in column A (the missing entries are not represented in the Affymetrix 430 2.0 chip that we have used). The percentages of overexpressed, pathwayspecific genes are higher in the Kras* than in the other tumors. Statistical analysis (Fisher's exact test) comparing the expressed and nonexpressed components in Kras* tumors with the corresponding data of each of the other cases shows that there are highly significant differences (columns P) with very few exceptions (NS). Analogous differences were not observed for downregulated genes.

TABLE 7

Components of signaling pathways overexpressed in Kras*-induced carcinomas

| SYMBOL | NAME | C/N | ↓ | ↑ |
|---|---|---|---|---|
| | Rac/MAPK Pathway | | | |
| Arrb2 | arrestin beta 2 | 2.8 | | 2.8 |
| Atf2 | activating transcription factor 2 | 2.7 | | |
| Atf4 | activating transcription factor 4 | 2 | | 2.5 |
| Braf | Braf transforming gene | 3.1 | | |
| Dusp14 | dual specificity phosphatase 14 | 10.2 | | 3.7 |

TABLE 7-continued

Components of signaling pathways overexpressed in Kras*-induced carcinomas

| SYMBOL | NAME | C/N | ↓ | ↑ |
|---|---|---|---|---|
| Dusp15 | Dual specificity phosphatase 15 | 2.6 | | |
| Dusp5 | dual specificity phosphatase 5 | 3.5 | | |
| Dusp6 | dual specificity phosphatase 6 | 6 | | |
| Dusp7 | dual specificity phosphatase 7 | 13.8 | | |
| Dusp9 | dual specificity phosphatase 9 | 7.7 | | |
| Flna | filamin, alpha | 2.7 | | |
| Flnb | filamin, beta | 9.2 | | |
| Gna12 | guanine nucleotide binding protein, alpha 12 | 7 | | 2.8 |
| Hras1 | Harvey rat sarcoma virus oncogene 1 | 3 | | |
| Map2k3 | mitogen activated protein kinase kinase 3 | 2.1 | | |
| Map2k4 | Mitogen activated protein kinase kinase 4 | 2.5 | | |
| Map3k1 | mitogen activated protein kinase kinase kinase 1 | 2 | | |
| Map3k7 | mitogen activated protein kinase kinase kinase 7 | 2.7 | | |
| Map3k7ip2 | mitogen-activated protein kinase kinase kinase 7 interacting protein 2 | 2.5 | | |
| Map4k4 | mitogen-activated protein kinase kinase kinase kinase 4 | 2.9 | | |
| Mapk13 | mitogen activated protein kinase 13 | 3.1 | | |
| Mapk14 | mitogen activated protein kinase 14 | 2.7 | | |
| Mapk9ip2 | mitogen-activated protein kinase 9 interacting protein 2 | 2.4 | | |
| Mapk8ip3 | mitogen-activated protein kinase 8 interacting protein 3 | 3.1 | | |
| Mapkapk2 | MAP kinase-activated protein kinase 2 | 3 | | |
| Nras | neuroblastoma ras oncogene | 3.7 | | |
| Pak1 | p21 (CDKN1A)-activated kinase 1 | 3.3 | | |
| Pdgfa | platelet derived growth factor, alpha | 2.5 | 2 | |
| Pdgfrb | platelet derived growth factor receptor, beta polypeptide | 2.5 | | |
| Ppm1b | Protein phosphatase 1B, magnesium dependent, beta isoform | 2.2 | | 2.5 |
| Ppp5c | protein phosphatase 5, catalytic subunit | 3.3 | | |
| Rasa1 | RAS p21 protein activator 1 | 3.1 | | |
| Rras2 | related RAS viral (r-ras) oncogene homolog 2 | 2.5 | | |
| Stmn1 | stathmin 1 | 3.4 | | 2.4 |
| Taok1 | TAO kinase 1 | 5.4 | | |
| Phosphatidylinositol Pathway | | | | |
| Akt1 | thymoma viral proto-oncogene 1 | 19 | | |
| Akt3 | thymoma viral proto-oncogene 3 | 2.5 | | 2.2 |
| Calm3 | calmodulin 3 | 2.5 | | |
| Calm4 | calmodulin 4 | 2.9 | | 2.3 |
| Calml3 | calmodulin-like 3 | 34.2 | | |
| Dgkz | diacylglycerol kinase zeta | 2.4 | | |
| inppl1 | inositol polyphosphate phosphatase-like 1 | 4.2 | | |
| itpr1 | inositol 1,4,5-triphosphate receptor 1 | 2 | | |
| itpr3 | inositol 1,4,5-triphosphate receptor 3 | 6.7 | | |
| Ocrl | oculocerebrorenal saydrome of Lowe | 2.5 | | |
| Pik3cg | phosphoinositide-3-kinase, catalytic, gamma polypeptide | 2.2 | 5 | |
| Pik3r3 | phosphatidylinositol 3 kinase regulatory subunit, polypeptide 3 (p55) | 2.3 | | |
| Pip5k1a | phosphatidylinositol-4-phosphate-5-kinase, type 1 alpha | 2.9 | | |
| Pip5k1b | Phosphatidylinositol-4-phosphate-5-kinase, type 1 beta | 2.4 | | |
| Pip5k2a | phosphatidylinositol-4-phosphate-5-kinase, type II alpha | 2 | 2.1 | |
| Plp5k2c | phosphatidylinostiol-4-phosphate 5-kinase, type III, gamma | 5.8 | | |
| Plcd3 | phospholipase C, delta 3 | 3.3 | | |
| Synij1 | Synapiojanin 1 | 2.4 | | |
| Synij2 | synapiojanin 2 | 3.2 | | |
| mTOR Pathway | | | | |
| Ddit4 | DNA-damage-inducible transcript 4 | 10.2 | | |
| Eif4E | eukaryotic traslation initiation factor 4E | 2.9 | | |
| Eif4e2 | eukaryotic translation initiation factor 4E member 2 | 2.7 | | |
| Frap1 | FK5D5 binding protein 12-rapamycin associated protein 1 | 2.4 | | |
| Hf1a | hypoxia inducible factor 1, alpha subunit | 2.4 | | |
| Rps6ka1 | ribosomal protein B6 kinase polypeptide 1 | 2.1 | | 3.5 |
| Rps6ka6 | ribosomal protein B6 kinase polypeptide 6 | 7 | | 6.4 |
| Rps6kb1 | ribosomal protein B6 kinase, polypeptide 1 | 2.8 | | |
| Rps6kb2 | ribosomal protein B6 kinase, polypeptide 2 | 2.2 | | |
| Ulk1 | Unc-51 like kinase 1 (*C. elegans*) | 2.3 | | |
| Erbb Pathway | | | | |
| Areg | amphiregulin | 57.5 | | |
| Ctl | Casitas B-lineage lymphoma | 4.1 | | |
| Ctlc | Casitas B-lineage lymphoma c | 2.3 | | 2.5 |
| Ertb2 | v-erb-b2 erythroblastic leukemia viral oncogene homolog 2 | 3.1 | | 2.6 |
| Ereg | epiregulin | 33.5 | 4.5 | |
| Hbegf | heparin-binding EGF-like growth factor | 101.5 | | |
| Nck2 | non-catalytic region of tyrosine kinase adaptor protein 2 | 3.7 | | 2.3 |
| Nrg1 | neuregulin 1 | 3.9 | 4.2 | |
| Nrg3 | neuregulin 3 | 4.9 | | |
| Shc1 | src homolog 2 domain-containing transforming protein C1 | 6.5 | | |
| Shc4 | SHC (Src homology 2 domain containing) family, member 4 | 5.5 | | |

TABLE 7-continued

Components of signaling pathways overexpressed in Kras*-induced carcinomas

| SYMBOL | NAME | C/N | ↓ | ↑ |
|---|---|---|---|---|
| Src | Rous sarcoma oncogene | 4.1 | | |
| Tgfa | transforming growth factor alpha | 7.6 | | |

Wnt Pathway

| SYMBOL | NAME | C/N | ↓ | ↑ |
|---|---|---|---|---|
| Axin1 | axin 1 | 3.5 | | 2.3 |
| Csnk2a1 | casein kinase 2, alpha 1 polypeptide | 3.4 | | |
| Csnk2a1 | casein kinase 2, alpha 1 polypeptide | 15.4 | | |
| Csnk2a1 | casein kinase 2, alpha 1 polypeptide | 2.5 | | |
| Csnk2a2 | casein kinase 2, alpha prime polypeptide | 3 | | |
| Csnk2a2 | casein kinase 2, alpha prime polypeptide | 2.4 | | |
| Ctanb1 | catenin (cadherin associated protein), beta 1 | 4.7 | | |
| Ctanb1 | catenin (cadherin associated protein), beta 1 | 2.4 | | |
| Ctnnbip1 | catenin beta interacting protein 1 | 2.5 | | 2.1 |
| Daam1 | dishevelled associated activator of morphogenesis 1 | 3.3 | | 2.6 |
| Dkk2 | dickkopf homolog 2 (Xenopus laevis) | 5.4 | 8.3 | |
| Dvl1 | dishevelled, dsh homolog 1 (Drosophila) | 2 | | |
| Dvl1 | dishevelled, dsh homolog 1 (Drosophila) | 2 | | |
| Fzd2 | frizzled homolog 2 (Drosophila) | 14.5 | | |
| Fzd2 | frizzled homolog 2 (Drosophila) | 3.5 | | |
| Fzd6 | frizzled homolog 6 (Drosophila) | 2.3 | | |
| Fzd6 | frizzled homolog 6 (Drosophila) | 2.5 | | |
| Lrp5 | low density lipoprotein receptor-related protein 6 | 3.7 | | |
| Nfat5 | Nuclear factor of activated T-cells 5 | 3.1 | | |
| Nfat5 | nuclear factor of activated T-cells 5 | 2.5 | | |
| Nkd1 | naked cuticle 1 homolog (Drosophila) | 2.2 | | 5.8 |
| Nkd2 | Naked cuticle 2 homolog (Drosophila) | 2.9 | | |
| Fpp2r1a | protein phosphatase 2 (formerly 2A), regulatory subunit A (PR 55), alpha isoforme | 2.4 | | |
| Prickle1 | prickle like 1 (Drosophila) | 14.8 | | 3.6 |
| Prickle1 | prickle like 1 (Drosophila) | 2.7 | | 2.6 |
| Prickle1 | prickle like 1 (Drosophila) | 3.2 | | |
| Prickle1 | prickle like 1 (Drosophila) | 5.9 | | |
| Ruvbl1 | RuvB-like protein 1 | 2 | | |
| Senp2 | SUMO/sentrin specific peptidase 2 | 2.2 | | |
| Sfrp1 | secreted frizzled-related sequence protein 1 | 2.8 | 2.7 | |
| Sfrp1 | secreted frizzled-related sequence protein 1 | 5.8 | 5.4 | |
| Sfrp1 | secreted frizzled-related sequence protein 1 | 3 | 8.2 | |
| Sfrp1 | secreted frizzled-related sequence protein 1 | 3.9 | 12.1 | |
| Tbl1x | transducin (beta)-like 1 X-linked | 13.3 | | |
| Tbl1x | Transducin (beta)-like 1 X-linked | 3 | | |
| Tcf7l2 | Transcription factor 7-line 2, T-cell specific, HMG-box | 3.2 | | |
| Vangl2 | vang-like 2 (wan gogh, Drosophila) | 3.2 | | 2.4 |
| Wint10a | wingless-related MMTV integration site 10a | 4.5 | 4 | |
| Wint5a | wingless-related MMTV integration site 5A | 5.1 | | 3.4 |
| Wint7b | wingless-related MMTV integration site 7B | 3.2 | 2.7 | |
| Wint7b | wingless-related MMTV integration site 7B | 4.1 | 3.6 | |
| Wint5a | wingless-type MMTV integration site 5A | 2.9 | 6.4 | |

Notoh Pathway

| SYMBOL | NAME | C/N | ↓ | ↑ |
|---|---|---|---|---|
| Adam10 | a disintegrin and metallopeptidase domain 10 | 2.5 | | |
| Adam17 | a disintegrin and metallopeptidase domain 17 | 3.1 | | |
| Aph1a | anterior pharynx defective 1s homolog (C. elegans) | 4 | | |
| Dll4 | cells-like 4 (Drosophila) | 2 | | |
| Dtx3l | cellex 3-like (Drosophila) | 2.1 | | |
| Fhl1 | four and a half domains 1 | 4.5 | | |
| Gcnsl2 | GCN5 general control of amino acid synthesis-like 2 (yeast) | 2.7 | | |
| Hdse2 | histone desacetylase 2 | 4.3 | | |
| Hes1 | hairy and enhancer of split 1 (Drosophila) | 2.7 | | |
| Jag1 | jagged 1 | 7.6 | 5.1 | |
| Jag2 | jagged 2 | 2.3 | 2.3 | |
| Ncor2 | nuclear receptor ca-repressor 2 | 3 | | |
| Notch1 | Notch gene homolog 1 (Drosophila) | 2.3 | | |
| Notch3 | Notch gene homolog 1 (Drosophila) | 6.1 | | 2 |
| Snw1 | SNW domain containing 1 | 4.5 | | |

Tgrb Pathway

| SYMBOL | NAME | C/N | ↓ | ↑ |
|---|---|---|---|---|
| Acwr1 | activin A receptor, type 1 | 3.1 | | |
| Acwr1b | activin A receptor, type 1B | 2.1 | | |
| Acwr2a | Activin receptor IIA | 2.9 | | |
| Bmp7 | bone morphogenetic protein 7 | 4 | | 3.6 |
| Bmpr1b | bone morphogenetic protein receptor, type 1B | 2.8 | 2.5 | |
| Bmpr2 | bone morphogenetic protein receptor, type II (serinethreonine kinase) | 3.5 | | |
| Fst | folistatin | 4.1 | | |
| Id1 | inhibitor of DNA binding 1 | 2.5 | | |
| Id4 | inhibitor of DNA binding 4 | 5 | | 2.1 |
| Inhba | inhibin beta-A | 20.2 | 5.7 | |
| Smad1 | MAD homolog 1 (Drosophila) | 3.4 | | |

TABLE 7-continued

Components of signaling pathways overexpressed in Kras*-induced carcinomas

| SYMBOL | NAME | C/N | ↓ | ↑ |
|---|---|---|---|---|
| Smad3 | MAD homolog 3 (*Drosophila*) | 2.1 | | |
| Smad5 | MAD homolog 5 (*Drosophila*) | 3.1 | | |
| Smad7 | MAD homolog 7 (*Drosophila*) | 3.4 | | |
| Smurf1 | SMAD specific E3 ubiquitin protein ligase 1 | 2.9 | | 2.4 |
| Smurf2 | SMAD specific E3 ubiquitin protein ligase 2 | 3.7 | | |
| Sp1 | trans-acting transcription factor 1 | 5.7 | | |
| Tgfb1 | transforming growth factor, beta 1 | 4.5 | | |
| Tgfb2 | transforming growth factor, beta 2 | 2.4 | | 3.7 |
| Tgfbr1 | Transforming growth factor, beta receptor I | 2.9 | | |
| Tgfbr2 | Transforming growth factor, beta receptor II | 2.2 | | |
| Thbs1 | thrombospondin 1 /// similar to thrombospondin 1 | 5 | | |
| Thbs2 | thrombospondin 2 | 3.5 | 6.3 | |
| Jak/Stat Pathway | | | | |
| Ctcf1 | cardiotrophin-like crystalline factor 1 | 2.9 | 5.1 | |
| Cntf | cIlary neurotrophic factor | 2.5 | | |
| Csf2 | calony stimulating factor 2 (granulocyte-macrophage) | 2.1 | | 2 |
| Csf3 | calony stimulating factor 3 (granulocyte) | 2.5 | 2.7 | |
| Csf3r | calony stimulating factor 3 receptor (granulocyte) | 2.3 | | |
| Ilngr2 | interleukin gamma receptor 2 | 3.4 | | |
| Il13ra1 | interleukin 13 receptor, alpha 1 | 2.8 | | |
| Il20rb | interleukin 20 receptor beta | 4 | | 13.5 |
| Il23a | interleukin 23, alpha subunit p15 | 3.3 | 2.6 | |
| Il24 | interleukin 24 | 14.1 | 12.7 | |
| Il28ra | interleukin 28 receptor alpha | 3 | | |
| Il4ra | interleukin 4 receptor, alpha | 2.3 | | |
| Il6 | interleukin 6 | 2.2 | 2.5 | |
| Jak3 | Janus kinase 3 | 2.1 | | |
| Lif | leukemia inhibitory factor | 4.1 | | |
| Pias4 | protein inhibtor of activated STAT 4 | 3.3 | | |
| Socs3 | suppressor of cytokine signaling 3 | 2.8 | | |
| Socs5 | Suppressor of cytokine signaling 5 | 3.6 | | 2.2 |
| Spred1 | sprouty protein alth EVH-1 domain 1, related sequence | 3.5 | | |
| Spred2 | sprouty-related, EVH1 domain containing 2 | 4.6 | | |
| Spred3 | sprouty-related, EVH1 domain containing 3 | 6.3 | 2.5 | |
| Stam2 | Signal transducing adaptor molecule (SH3 domain and ITAM motif) 2 | 3.4 | | 2.4 |
| Hedgehog Pathway | | | | |
| Cank1d | casein kinase 1, delta | 2.8 | | |
| Cank1g1 | casein kinase 1, gamma 1 | 5 | | |
| Cank1g2 | casein kinase 1, gamma 2 | 2.1 | | 2 |
| Dhh | desert hedgehog | 4 | | |
| Gli3 | GLI-Kruppel family member GLI3 | 2.2 | | |
| Ptch2 | patched homolog 2 | 2.5 | | |
| Stk35 | serinethreonine kinase 35 (fused homolog, *Drosophila*) | 2.2 | | |
| Vegf Pathway | | | | |
| Pxn | paxlin | 4.5 | | 2.1 |
| Sphk1 | sphingosine kinase 1 | 4.8 | | |
| Vegfa | vascular endothelial growth factor A | 2.5 | | 2 |
| Vegfc | vascular endothelial growth factor C | 3 | | |
| Cell Cycle | | | | |
| Anapc5 | anaphase-promoting complex subunit 5 | 2.2 | | |
| Bub1 | budding uninhibited by benzimidazoles 1 homolog (*S. cerevisiae*) | 10.3 | | |
| Bub1b | budding uninhibited by benzimidazoles 1 homolog, beta (*S. cerevisiae*) | 5.4 | | 2.1 |
| Bub3 | budding uninhibited by benzimidazoles 3 homolog (*S. cerevisiae*) | 2.3 | | |
| Ccna2 | cyclin A2 | 7.6 | | |
| Ccnb1 | cyclin B1 | 17 | | 2 |
| Ccnb2 | cyclin B2 | 11.5 | | |
| Ccnd1 | cyclin D1 | 10 | | |
| Ccnd2 | cyclin D2 | 3 | | |
| Ccne2 | cyclin E2 | 3.3 | | |
| Cdc20 | cell division cycle 20 homolog (*S. cerevisiae*) | 7.3 | | |
| Cdc23 | CDC23 (cell division cycle 23, yeast, homolog) | 5.5 | | |
| Cdc25c | cell division cycle 25 homolog C (*S. pombe*) | 3 | | 2.2 |
| Cdc2a | cell division cycle 2 homolog A (*S. pombe*) | 14.8 | | |
| Cdc45l | cell division cycle 45 homolog (*S. cerevisiae*)-like | 3.5 | | |
| Cdc6 | cell division cycle 6 homolog (*S. cerevisiae*) | 2.9 | | |
| Cdc7 | cell division cycle 7 (*S. cerevisiae*) | 2.1 | | |
| Cdk4 | cyclin-dependent kinase 4 | 3.1 | | |
| Cdk6 | cyclin-dependent kinase 6 | 5.2 | | |
| Cdk7 | cyclin-dependent kinase 7 (homolog of *Xenopus* MO15 cdk-activating kinase) | 2.3 | | |
| Cdkn1a | cyclin-dependent kinase inhibtor 1A (P21) | 11.2 | | |
| Cdkn1b | cyclin-dependent kinase inhibtor 1B | 10.8 | | |
| Cdkn2b | cyclin-dependent kinase inhibtor 2B (p15, inhibits CDK4) | 5.4 | | |

TABLE 7-continued

Components of signaling pathways overexpressed in Kras*-induced carcinomas

| SYMBOL | NAME | C/N | ↓ | ↑ |
|---|---|---|---|---|
| Chek1 | checkpoint kinase 1 homolog (*S. pombe*) | 6.7 | | |
| Dbf4 | DBF4 homolog (*S. cerevisiae*) | 4.2 | | |
| E2f1 | E2F transcription factor 1 | 2.4 | | |
| E2f3 | E2F transcription factor 3 | 2.1 | | |
| Espl1 | extra spindle poles-like 1 (*S. cerevisiae*) | 3.4 | | |
| Fzr1 | fizzy/cell division cycle 20 related 1 (*Drosophila*) | 2.3 | | 2.1 |
| Mad1l1 | mitotic arrest deficient 1-like 1 | 2.2 | | |
| Mad2l1 | MAD2 (mitotic arrest deficient, homolog)-like 1 (yeast) | 2.6 | | |
| Mcm2 | minichromosome maintenance deficient 2 mitotic (*S. cerevisiae*) | 2.5 | | |
| Mcm3 | minichromosome maintenance deficient 3 (*S. cerevisiae*) | 2.9 | | |
| Mcm4 | minichromosome maintenance deficient 4 homolog (*S. cerevisiae*) | 2.7 | | |
| Mcm5 | minichromosome maintenance deficient 5, cell division cycle 46 (*S. cerevisiae*) | 3.7 | | |
| Mcm7 | minichromosome maintenance deficient 7 (*S. cerevisiae*) | 2.2 | | |
| Mcm2 | transformed mouse 373 cell double minute 2 | 4.1 | | |
| Orc1l | origin recognition complex, subunit 1-like (*S. cerevisiae*) | 2.1 | | |
| Orc2l | origin recognition complex, subunit 2-like (*S. cerevisiae*) | 2 | | |
| Orc4l | origin recognition complex, subunit 4-like (*S. cerevisiae*) | 2.7 | | 2.8 |
| Plt1 | polo-like kinase 1 (*Drosophila*) | 10 | | 2 |
| Sfn | stratfin | 11 | 3.2 | |
| Skp2 | S-phase kinase-associated protein 2 (p45) | 4.9 | | |
| Smc1a | structural maintenance of chromosomes 1A | 2.1 | | |
| Wee1 | wee 1 homolog (*S. pombe*) | 2.1 | | |
| Ywhag | 3-monooxygenase/tryptophan 5-monooxygenase activation protein, gamma | 3.8 | | |
| Ywhah | tyrosine 3-monooxygenase/tryptophan 5-monooxygenase activation protein, eta | 2.6 | | |
| Ywhaz | tyrosine 3-monooxygenase/tryptophan 5-monooxygenase activation protein, zeta | 3.4 | | |
| Apoptosis | | | | |
| Apaf1 | apoptotic peptidase activating factor 1 | 3 | | |
| Bad | Bcl-associated death promoter | 2 | | |
| Bax | Bcl2-associated X protein | 4.7 | | 2.2 |
| Bcl2l1 | Bcl2-like 1 | 3.4 | | 2 |
| BIrc4 | Baculoviral IAP repeat-containing 4 | 2.8 | | |
| Capn1 | calpain 1 | 5.6 | | |
| Casp3 | caspase 3 | 9.4 | | |
| Casp6 | caspase 6 | 2.5 | | |
| Il1a | interleukin 1 alpha | 3.3 | 3.9 | |
| Il1b | interleukin 1 beta | 13 | 4.7 | |
| Il1rap | interleukin 1 receptor accessory protein | 4.5 | | 2.2 |
| Irak2 | interleukin-1 receptor-associated kinase 2 | 8.6 | | 2 |
| Ngfb | nerve growth factor, beta | 3 | 3.5 | |
| Prkar1a | protein kinase, cAMP dependent regulatory, type I, alpha | 3.2 | | |
| Prkar2a | protein kinase, cAMP dependent regulatory, type II alpha | 2.3 | | |
| Tnfrsf10b | tumor necrosis factor receptor superfamily, member 10b | 2.2 | | |
| Tradd | TNFRSF1A-associated via death domain | 2.8 | | |
| TrpS3 | transformation related protein S3 | 4.8 | | |
| More than one Pathway | | | | |
| Crebbp | CRES binding protein | 5.5 | | |
| Cank1a1 | casein kinase 1, alpha 1 | 5.1 | | |
| Cank1e | casein kinase 1, epsilon | 10.1 | | 2.5 |
| Ctbp2 | C-terminal binding protein 2 | 2.3 | | 2.2 |
| Fbow11 | F-box and WD-40 domain protein 11 | 3.6 | | |
| Fosl1 | fos-like antigen 1 | 9.2 | 4.6 | |
| Gsk3b | glycogen synthase kinase 3 beta | 6.2 | | |
| Jun | Jun oncogene | 4.8 | | |
| Myc | myelocytomatosis oncogene | 2.4 | | 2.1 |
| Nfatc3 | nuclear factor of activated T-cells, cytoplasmic, calcineurin-dependent 3 | 3.4 | | |
| Nfatc4 | nuclear factor of activated T-cells, cytoplasmic, calcineurin-dependent 4 | 2.4 | 2.3 | |
| Nlk | Nemo like kinase | 4.3 | | |
| Ppp2cb | protein phosphatase 2 (formerly 2A), catalytic subunit, beta isoform | 2.3 | | |
| Prkacb | protein kinase, cAMP dependent, catalytic, beta | 3.6 | | |
| Prkca | protein kinase C, alpha | 2.4 | | |

C/N is the ratio or the level of expression in Kras* tumors over normal mammary glands. The same ratio was calculated in tumors that eventually developed after ablation of Igf1r. The fold differences between the two ratios for genes that were upregulated (↑) on downregulated (↓) in the absence of IGF signaling is indicated.

TABLE 8

List of components of signaling pathways
For details see SI Methods.

| MAPK | PI3K | mTOR | Erbb | Wnt | Notch | Tgfb | Jak/Stat | Hedgehog | Vegf | Cell Cycle | Apoptosis | >1 |
|---|---|---|---|---|---|---|---|---|---|---|---|---|
| Arrb1 | Atk1 | Ddit4 | Araf | Apc | Adam10 | Acvr1 | Cish | Csnk1d | Figf | Abl1 | Aifm1 | Btrc |
| Arrb2 | Akt2 | Eif4b | Areg | Apc2 | Adam17 | Acvr1b | Clcf1 | Csnk1g1 | Kdr | Anapc1 | Apaf1 | Crebbp |
| Atf2 | Akt3 | Eif4e | Btc | Axin1 | Aph1a | Acvr1c | Cntf | Csnk1g2 | Nos3 | Anapc10 | Atm | Csnk1a1 |
| Atf4 | Calm1 | Elf4e2 | Cbl | Axin2 | Asct1 | Acvr2a | Cntfr | Dhh | Pxn | Anapc11 | Bad | Csnk1e |
| Bdnf | Calm2 | Elf4ebp1 | Cblb | Cacybp | Dll1 | Acvr2b | Csf2 | Gas1 | Sh2d2a | Anapc2 | Bax | Ctbp1 |
| Braf | Calm3 | Frap1 | Cblc | Camk2a | Dll3 | Acvrl1 | Csf2ra | Gli1 | Sphk1 | Anapc4 | Bcl2 | Ctbp2 |
| Cacna1a | Calm4 | Hif1a | Egf | Camk2b | Dll4 | Amh | Csf3 | Gli2 | Sphk2 | Anapc5 | Bcl2l1 | Cul1 |
| Cacna1b | Calml3 | Rheb | Egfr | Camk2d | Dtx1 | Amhr2 | Csf3r | Gli3 | Vegfa | Anapc7 | Bid | Fbxw11 |
| Cacna1c | Carkl | Rps6 | Erbb2 | Camk2g | Dtx2 | Bmp2 | Ctf1 | Hhip | Vegfb | Bub1 | Birc2 | Fosl1 |
| Cacna1d | Cdipt | Rps6ka1 | Erbb3 | Cer1 | Dtx3 | Bmp4 | Epor | Ihh | Vegfc | Bub1b | Birc3 | Grb2 |
| Cacna1e | Cds1 | Rps6ka2 | Erbb4 | Csnk2a1 | Dtx3l | Bmp5 | Gh | Lrp2 | | Bub3 | Birc4 | Gsk3b |
| Cacna1f | Dgka | Rps6ka3 | Ereg | Csnk2a2 | Dtx4 | Bmp6 | Ghr | Ptch1 | | Ccna1 | Capn1 | Ifng |
| Cacna1g | Dgke | Rps6ka6 | Gab1 | Csnk2b | Fbxw7 | Bmp7 | Ifna1 | Ptch2 | | Ccna2 | Capn2 | Jun |
| Cacna1h | Dgkg | Rps6kb1 | Hbegf | Ctnnb1 | Fhl1 | Bmp8a | Ifna11 | Rab23 | | Ccnb1 | Casp12 | Jund1 |
| Cacna1s | Dgkq | Rps6kb2 | Nck1 | Ctnnbip1 | Gcn5l2 | Bmp8b | Ifna2 | Shh | | Ccnb2 | Casp3 | Myc |
| Cacna2d1 | Dgkz | Tsc1 | Nck2 | Cxxc4 | Hdac1 | Bmpr1a | Ifna4 | Smo | | Ccnb3 | Casp6 | Nfatc1 |
| Cacna2d2 | Fn3k | Tsc2 | Nrg1 | Daam1 | Hdac2 | Bmpr1b | Ifna5 | Stk36 | | Ccnd1 | Casp7 | Nfatc2 |
| Cacna2d3 | Impa1 | Ulk1 | Nrg3 | Daam2 | Hes1 | Bmpr2 | Ifna6 | Sufu | | Ccnd2 | Casp8 | Nfatc3 |
| Cacnb1 | Impa2 | Ulk2 | Nrg4 | Dkk1 | Hes5 | Chrd | Ifna9 | Zic2 | | Ccnd3 | Casp9 | Nfatc4 |
| Cacnb2 | Inpp1 | Ulk3 | Shc1 | Dkk2 | Jag1 | Comp | Ifnab | | | Ccne1 | Cflar | Nlk |
| Cacnb3 | Inpp4a | | Sch2 | Dkk4 | Jag2 | Dcn | Ifnar1 | | | Ccne2 | Chuk | Plcb3 |
| Cacnb4 | Inpp4b | | Sch3 | Dvl1 | Lfng | Fst | Ifnar2 | | | Ccnh | Csf2rb1 | Plcb4 |
| Cacng1 | Inpp5a | | Sch4 | Dvl2 | Maml1 | Gdf5 | Ifnb1 | | | Cdc14a | Csf2rb2 | Ppp2ca |
| Cacng2 | Inpp5b | | Src | Dvl3 | Mfng | Id1 | Ifngr1 | | | Cdc14b | Cycs | Ppp2cb |
| Cacng3 | Inpp5d | | Tgfa | Frat1 | Ncor2 | Id2 | Ifngr2 | | | Cdc16 | Dffa | Ppp3ca |
| Cacng4 | Inpp5e | | | Frat2 | Nestn | Id3 | Il10 | | | Cdc20 | Dffb | Ppp3cb |
| Cacng5 | Inpp1 | | | Fzd1 | Notch1 | Id4 | Il10ra | | | Cdc23 | Endog | Ppp3cc |
| Cacng6 | Itgb1-bp3 | | | Fzd10 | Notch2 | Inhba | Il10rb | | | Cdc25a | Fadd | Ppp3r1 |
| Cacng7 | Itpka | | | Fzd2 | Notch3 | Inhbb | Il11 | | | Cdc25b | Fas | Ppp3r2 |
| Cacng8 | Itpkb | | | Fzd3 | Notch4 | Inhbc | Il12a | | | Cdc25c | Fasl | Prkaca |
| Cd14 | Itpr1 | | | Fzd4 | Numb | Inhbe | Il12b | | | Cdc27 | Ikbkb | Prkacb |
| Cdc42 | Itpr2 | | | Fzd5 | Numbl | Lefty1 | Il12rb1 | | | Cdc2a | Ikbkg | Prkca |
| Crk | Itpr3 | | | Fzd6 | Pcaf | Lefty2 | Il12rb2 | | | Cdc45l | Il1a | Prkcb1 |
| Crkl | Ocrl | | | Fzd7 | Pofut1 | Ltbp1 | Il13 | | | Cdc6 | Il1b | Prkcc |
| Daxx | Pdpk1 | | | Fzd8 | Psen1 | Nodal | Il13ra1 | | | Cdc7 | Il1r1 | Prkx |
| Ddit3 | Pib5pa | | | Fzd9 | Psen2 | Nog | Il13ra2 | | | Cdk2 | Il1rap | Rbl1 |
| Dusp1 | Pik3c2a | | | Lef1 | Psenen | Pitx2 | Il15 | | | Cdk4 | Il3 | Rbl2 |
| Dusp10 | Pik3c2g | | | Lrp6 | Ptcra | Rhoa | Il15ra | | | Cdk6 | Il3ra | Rbx1 |
| Dusp14 | Pik3c3 | | | Nfat5 | Rbpj | Rock1 | Il19 | | | Cdk7 | Irak1 | Skp1a |
| Dusp16 | Pik3ca | | | Nkd1 | Rfng | Rock2 | Il2 | | | Cdkn1a | Irak2 | Sos1 |
| Dusp2 | Pik3cb | | | Nkd2 | Snw1 | Smad1 | Il20 | | | Cdkn1b | Irak3 | Sos2 |
| Dusp3 | Pik3cd | | | Porcn | Wdr12 | Smad2 | Il20ra | | | Cdkn1c | Irak4 | Tfdp1 |
| Dusp4 | Pik3cg | | | Ppard | | Smad3 | Il20rb | | | Cdkn2b | Myd88 | |
| Dusp5 | Pik3r1 | | | Ppp2r1a | | Smad4 | Il21 | | | Cdkn2c | Nfkb1 | |
| Dusp6 | Pik3r2 | | | Ppp2r1b | | Smad5 | Il21r | | | Cdkn2d | Nfkb2 | |
| Dusp7 | Pik3r3 | | | Ppp2r2b | | Smad7 | Il22 | | | Chek1 | Nfkbia | |
| Dusp8 | Pik3r5 | | | Ppp2r2c | | Smad9 | Il22ra1 | | | Chek2 | Ngfb | |
| Dusp9 | Pik4ca | | | Ppp2r2d | | Smurf1 | Il22ra2 | | | Dbf4 | Ntrk1 | |
| Ecsit | Pik4cb | | | Prickle1 | | Smurf2 | Il23a | | | E2f1 | Prka1a | |
| Elk1 | Pip5k1a | | | Prickle2 | | Sp1 | Il24 | | | E2f3 | Prka1b | |
| Elk4 | Pip5k1b | | | Ruvbl1 | | Tgfb1 | Il28ra | | | Esp11 | Prka2a | |
| Evi1 | Pip5k1c | | | Senp2 | | Tgfb2 | Il2ra | | | Fzr1 | Prka2b | |
| Fina | Pip5k2a | | | Sfrp1 | | Tgfb3 | Il2rb | | | Gadd45a | Rela | |
| Finb | Pip5k2b | | | Sfrp2 | | Tgfbr1 | Il2rg | | | Gadd45b | Ripk1 | |
| Finc | Pip5k2c | | | Sfrp4 | | Tgfbr2 | Il4 | | | Gadd45g | Tnf | |
| Fos | Pip5k3 | | | Sfrp5 | | Thbs1 | Il4ra | | | Msd1l1 | Tnfrsf10b | |
| Gna12 | Plcd1 | | | Siah1a | | Thbs2 | Il5 | | | Msd2l1 | Tnfrsf1a | |
| Gng12 | Plcd3 | | | Sox17 | | Thbs3 | Il5ra | | | Msd2l2 | Tnfsf10 | |
| Hras1 | Plcd4 | | | Tbl1x | | Thbs4 | Il6 | | | Mcm2 | Tradd | |
| Kras | Plce1 | | | Tbl1xr1 | | Zfyve16 | Il6ra | | | Mcm3 | Traf2 | |
| Map2k1 | Plcg1 | | | Tcf3 | | Zfyve9 | Il6st | | | Mcm4 | Trp53 | |
| Map2k1-ip1 | Plcg2 | | | Tcf7 | | | Il7 | | | Mcm5 | | |
| Map2k2 | Plcz1 | | | Tcf7l2 | | | Il7r | | | Mcm6 | | |
| Map2k3 | Pten | | | Vangl1 | | | Il9 | | | Mcm7 | | |
| Map2k4 | Synj1 | | | Vangl2 | | | Il9r | | | Mdm2 | | |
| Map2k5 | Synj2 | | | Wif1 | | | Isgf3g | | | Orc1l | | |
| Map2k6 | | | | Wnt1 | | | Jak1 | | | Orc2l | | |
| Map2k7 | | | | Wnt10a | | | Jak2 | | | Orc3l | | |

Conditional Ablation of Igf1r Delays Kras*-induced Mammary Tumorigenesis

One of the most interesting changes detected in Kras*-induced mammary cancers by RNA profiling was an increased expression of Igf1r, which was confirmed by Northern analysis. This prompted an investigation about the potential involvement of IGF signaling in the development of mammary tumors in this mouse model.

A compelling reason for asking this question is evidence in the prior art suggesting that cells lacking Igf1r cannot be transformed by any one of several tested oncoproteins (Baserga, *Expert Opin. Ther. Targets* (2005), 9, 753-68). Apparently, Igf1r-mediated signaling is not an oncogenic component per se, but a crucial prerequisite for oncogenesis considering that, among other effects, it provides a necessary and strong antiapoptotic signal for tumor growth. The Igf1r gene is neither amplified nor obligatorily overexpressed in human breast cancer. Thus, despite reported cases of overexpression, it is not uncommon to detect Igf1r mRNA levels that are equal or even lower in cancer cells than in normal breast tissue (Chong et al., *Anticancer Res.* (2006), 26(1A), 167-73). Nevertheless, it is interesting that 36% of examined basal-like breast cancers (n=64) were shown by immunohistochemistry to be Igf1r-positive (Lerma et al., *Mod. Pathol.* (2007), 20, 1200-07).

To examine the impact of the absence of Igf1r on the development of mammary tumors induced by Kras* overexpression, tumorigenic progression was compared between animals carrying the oncogenic transgene in a background either wild-type for Igf1r (Eef1a1-Kras*/Wapcre mice serving as controls) or possessing one or two floxed Igf1r alleles that could be conditionally ablated (Eef1a1-Kras*/Wapcre/Igf1r$^{fl/+}$ and Eef1a1-Kras*/Wap$^{cre}$/Igf1r$^{fl/fl}$ genotypes; n=11 and n=14, respectively).

It was observed that, in contrast to cancer manifestation after the first birth with a T50 of 9 days in control mice, ablation of both floxed Igf1r alleles in experimental animals resulted in tumor development only after three pregnancies, while the latency increased dramatically (11-fold; T50=101 days; P<0.0001, log-rank test; FIG. 1D). However, complete rescue was not observed, perhaps owing to the occurrence of mutational and/or epigenetic alterations compensating for the absence of IGF signaling (Southern analysis confirmed that Cre-mediated recombination had occurred in the Igf1r locus, while the tumors lacked Igf1r expression detectable by immunohistochemistry or by Northern/Western analysis; data not shown). Immunostaining for all examined markers (including pAkt, pErk1/2 and pS6) was virtually unaltered in the Igf1r−/− tumors, while significant differences in the multifocality and overall size of the carcinomas or in the proliferation indices of the components were not noted (Table 3). On the other hand, with the exception of SRC, significant alterations were observed in the relative sizes of the components (Table 3). Interestingly, absence of only one Igf1r allele (Eef1a1-Kras*/Wap$^{cre}$/Igf1r$^{fl/+}$ animals) also resulted in a statistically significant delay in tumor appearance after a first pregnancy (~5-fold increase in latency; P=0.01; FIG. 1D).

Comparison of the expression profiles of Kras* cancers developing in the presence or absence of Igf1r signaling revealed, among other effects (Table 9), significant differences in transcript levels for Egf ligands that were confirmed by Northern analysis. Specifically, with intact Igf1r, there was >100-fold increase over normal in the amount of steady-state mRNA for Hbegf present in the tumors, while the levels of overexpressed transcripts for Areg, Ereg and Tgfa were less dramatic (~4-, 15- and 6-fold, respectively). Interestingly, a similar overexpression of Egf ligands was observed in an HrasG12V breast cancer model (Sarkisian C J, et al. *Nat. Cell Biol.* (2007), 9:493-505), implying a more general feedback loop involving Ras protein function. It was found that elimination of Igf1r only slightly affected the overexpression of Areg, but resulted in the reduction of the Ereg and Tgfa transcripts to almost normal levels, while the previously enormous amount of Hbegf mRNA was reduced approximately by half. In contrast, Igf1 and Igf2 transcripts encoding IGF ligands were virtually absent from the tumors and Igf1 and Igf2 polypeptides were below detection limits by immunohistochemistry (Table 4) indicating absence of IGF autocrine/paracrine signaling cues. Accordingly, unless it is eventually found that Igf1r-mediated signaling is triggered by EGF ligands acting through non-canonical IGF1R-EGFR heterodimers (Riedemann, J., et al., *Biochem. Biophys. Res. Commun.* (2007), 355, 707-714), it is likely that the IGF functions are served in the Kras* mammary cancers by endocrine action of IGF1 circulating in serum. Assuming this to be the case, it appears that IGF signaling potentiates Erbb-mediated activities by upregulating Egf ligands through an unknown mechanism, which could be transcriptional and could involve Ap1 sites present in the promoter regions of some of these ligands (Ornskov D, et al., *Biochem. Biophys. Res. Commun.* (2007), 354:885-891). Interestingly, Fosl1, an Ap1 component, is highly overexpressed in the Kras* tumors (FIG. 6 and Table 4). Three of the four Erbb receptors (Egfr, Erbb2 and Erbb3) are present in the Kras* tumors, but they are not overexpressed. In fact, Erbb2 transcripts remain undetectable by Northern analysis, although the receptor itself can be seen in the carcinomas by immunostaining (FIG. 6).

TABLE 9

List of primary antibodies

| Antigen | Source | Name/Clone$^a$; Catalog No. | Retrieval$^b$ | Incubation$^c$ |
|---|---|---|---|---|
| CK18 (Krt18) | Abcam, Cambridge, MA | Clone C-04; ab668 | pH6.0 | 1 h RT, 1:200 |
| ER | Santa Cruz Biotechnology, Santa Cruz, CA | Polyclonal(Rb); sc-543 | none | 1 h RT, 1:400 |
| PR | ABR Affinity Bioreagents, Golden, CO | Clone PR-AT 4.14; MA1-410 | pH6.0 | O/N 4° C., 1:50 |
| Gata3 | Santa Cruz Biotechnology, Santa Cruz, CA | Polyclonal(Gt); sc-1236 | pH6.0 | O/N 4° C., 1:100 |
| CK5 (Krt5) | Covance, Princeton, NJ | Polyclonal(Rb); PRB-160P | pH6.0 | 1 h RT, 1:500 |
| CK14 (Krt14) | Covance, Princeton, NJ | Polyclonal(Rb); PRB-155P | pH6.0 | 1 h RT, 1:500 |
| SMA (Actg2) | Dako, Carpinberia, CA | Clone 1A4; M085129 | pH6.0 | O/N 4° C., 1:200 |
| p63 (Trp63) | BD Pharmingen, San Diego, CA | Clone 4A4; 559951 | pH6.0 | O/N 4° C., 1:500 |
| Itga6 | Santa Cruz Biotechnology, Santa Cruz, CA | Polyclonal(Gt); sc-6596 | pH6.0 | O/N 4° C., 1:50 |
| Itgb1 | Millipore Corp, Billerica, MA | Clone P4G11; MAB-1951 | none | O/N 4° C., 1:50 |
| CD24 | BD Pharmingen, San Diego, CA | Clone M1/69; 557436 | pH6.0 | 1 h RT, 1:200 |
| CK6 (Krt6) | Covance, Princeton, NJ | Polyclonal(Rb); PRB-169P | pH6.0 | 1 h RT, 1:200 |
| Nestin | DSHB, Iowa City, IA | Clone Rat 401c | pH6.0 | O/N 4° C., 1:50 |
| Annexin VIII | Santa Cruz Biotechnology, Santa Cruz, CA | Polyclonal(Rb); sc-28825 | pH6.0 | O/N 4° C., 1:200 |

TABLE 9-continued

List of primary antibodies

| Antigen | Source | Name/Clone[a]; Catalog No. | Retrieval[b] | Incubation[c] |
|---|---|---|---|---|
| Sca1 | Cedarlane Labs, Hornby, ON | Clone CT-6A/6E; CL8934AP | none | O/N 4° C., 1:50 |
| pErk | Cell Signalling Technology, Danvers, MA | Clone E10; 9106 | pH6.0 | O/N 4° C., 1:50 |
| pAkt1 | Cell Signalling Technology, Danvers, MA | Polyclonal(Rb); 9277 | pH6.0 | O/N 4° C., 1:50 |
| pS6 | Cell Signalling Technology, Danvers, MA | Polyclonal(Rb); 2211 | pH6.0 | O/N 4° C., 1:200 |
| Igf1r | Cell Signalling Technology, Danvers, MA | Polyclonal(Rb); 3027 | pH7.5 | O/N 4° C., 1:200 |
| Igf1 | Dr. Louis E. Underwood | — | none | O/N 4° C., 1:200 |
| Igf2 | Upstate Biotechnology, Lake Placid, NY | Clone S1F2; 05-166 | pH6.0 | O/N 4° C., 1:50 |
| Egfr | Cell Signalling Technology, Danvers, MA | Polyclonal(Rb); 2232 | pH7.5 | O/N 4° C., 1:100 |
| Erbb2 (Neu) | Santa Cruz Biotechnology, Santa Cruz, CA | Polyclonal(Rb); sc-284 | pH6.0 | O/N 4° C., 1:200 |
| Erbb3 | BD PharMingen, San Diego, CA | Clone RTJ.1.554208 | pH6.0 | O/N 4° C., 1:200 |
| Fosl1 | Santa Cruz Biotechnology, Santa Cruz, CA | Polyclonal(Rb); sc-605 | pH6.0 | O/N 4° C., 1:100 |
| Casp3(Asp175) | Cell Signalling Technology, Danvers, MA | Polyclonal(Rb); 9661 | pH6.0 | O/N 4° C., 1:200 |
| KI-67 | Novus Biologicals, Littleton, CO | Clone SP6; NB110-57147 | pH6.0 | O/N 4° C., 1:500 |
| E-cadherin | BD Biosciences, San Jose, CA | Clone 36; 610182 | pH6.0 | O/N 4° C., 1:500 |
| β-catenin | BD Biosciences, San Jose, CA | Clone 14; 610153 | pH6.0 | O/N 4° C., 1:100 |
| Vimentin | Fitzgerald Industries, Concord, MA | Polyclonal(Gp); PROGP53 | pH6.0 | O/N 4° C., 1:500 |

[a]Rb: rabbit; Gt: goat; Gp: guinea pig
[b]pH6.0: antigen retrieval by boiling 15 minutes in 0.01M citrate buffer pH6.0
pH7.5: antigen retrieval by boiling 15 minutes in 0.01M EDTA pH7.5
[c]O/N: overnight; RT: room temperature Pharmacological Treatment of Kras*-induced Mammary Tumors The strong genetic evidence for an Igf1r role in mammary tumorigenesis at least in the examined model is significant in the context of efforts to develop therapeutic approaches for treating breast cancer by blocking of IGF signaling. This could turn out to be significant for basal-like carcinomas, which have poor prognosis (Sorlie T, et al. *Proc. Natl. Acad. Sci. USA* (2001), 98:10869-10874) and pose a serious problem to targeted therapies (Cleator S, et al., *Lancet Oncol.* (2007). 8:235-244; Carey L A, et al., *Clin. Cancer Res.* (2007), 13:2329-2334), considering that the use of antiestrogens in combination with trastuzumab (anti-ERBB2 antibody) is not an option, while there is no clear choice for chemotherapy. Therefore, the Kras* model was used in a preclinical study testing the efficacy of the cyclolignan picropodophyllin (PPP), which has recently emerged as a potent, nontoxic and highly specific Igf1r inhibitor (Girnita, et. al., *Cancer Res.* (2004), 64, 236-42). Although the molecular mechanism of PPP action is still unknown, its inhibitory effects appear to be exerted by abrogation of Igf1r phosphorylation and promotion of its degradation, while the homologous insulin receptor is not affected (Girnita, et. al., *Cancer Res.* (2004), 64, 236-42; Vasilcanu, et al., *Oncogene*, (2008), 27: 1629-1638). Cell lines of Igf1r null fibroblasts are apparently insensitive to PPP, whereas the drug reduces the viability of cancer cell lines and causes tumor regression in mouse xenografts of multiple myeloma (Menu et al., *Int. J. Cancer* (2007), 121, 1857-61) and uveal melanoma (Girnita et al., *Clin. Cancer Res.* (2006), 12, 1383-91). Therefore, the Kras* model described herein was used for testing the potential therapeutic effects of PPP on breast cancer. For this purpose, PPP was administered either alone or in combination with erlotinib, an Egfr inhibitor (Yang S X, et al., *Clin. Cancer Res.* (2005), 11: 6226-6232), taking into consideration the overexpression of Erbb ligands and Igf1r/Egfr signaling relationships described above.

Mice at a progressed stage of tumorigenesis bearing at least one readily palpable tumor were injected intraperitoneally once daily either with vehicle or with PPP and Erlotinib, alone or in combination, at doses of 30 mg/kg and 50 mg/kg, respectively, for a period of 3 weeks, considering that the weight of some tumors in the controls could reach or exceed ~1 g by that time. At the end of treatment, we measured tumor growth relative to control values by calculating tumor mass, and we did not attempt sequential measurements using a caliper because a pilot study indicated that they were inaccurate. First, the tumors developing in each gland tended to be multifocal and uneven, and progressively coalesced into larger masses precluding reliable evaluation. In addition, the treatment resulted in extensive tumor necrosis and fibrosis detectable only histologically, which would have artificially inflated macroscopic measurements.

All glands carrying tumors in treated and control animals were analyzed, and for statistical evaluation, it was taken into account that the cancers exhibited pronounced size heterogeneity (see FIGS. 3A-3F). On average, either Erlotinib or PPP was effective and did not permit expansion of tumor volume per mammary gland beyond a level of ~30% and ~7% of the control value, respectively (Table 6). The effect of the drugs used in combination (~4% of control) was perhaps only additive (dose-response relationships were not yet studied). Monitoring of body weights and histological examination of various organs from vehicle- and drug-treated mice did not reveal signs of non-specific toxicity.

TABLE 6

Drug treatments

| | Mice (n) | Glands (n) | Tumor volume per gland (mm³)[a] | % | P[b] |
|---|---|---|---|---|---|
| Mouse Tumors | | | | | |
| Vehicle | 7 | 21 | 217.8 ± 65.6 | 100 | |
| Erlotinib | 4 | 16 | 66.9 ± 29.3 | 30.7 | 0.005 |
| PPP | 5 | 17 | 16.0 ± 9.1 | 7.3 | <0.001 |
| PPP + Erlotinib | 5 | 18 | 8.6 ± 3.9 | 3.9 | <0.0001 |
| Xenografts | | | | | |
| Vehicle | 5 | 20 | 304 ± 40.8 | 100 | |
| PPP | 5 | 20 | 215 ± 18.6 | 70.7 | 0.02 |

[a]Mean ± S.E.M.
[b]Because of data skewness, in tumor volume comparisons between the drug treatments and the control (vehicle), probabilities (P) were calculated using Student's t-test after logarithmic transformation of the values to meet the distribution criterion of the test.

Not unexpectedly, vehicle administration did not alter the histopathological or immunophenotypic profile of tumors, whereas the specimens of mice treated either with PPP or with a PPP/Erlotinib combination displayed a marked reduction or even absence of the pale and squamous cell components accompanied by extensive keratinization and vacuolation (FIGS. 3A-3F). Thus, small cancerous lesions observed post-treatment consisted only of glandular and spindle cell types. The extent of the latter, however, which exhibited degenerative changes, is difficult to quantitate. Erlotinib acting alone reduced predominantly the pale cell component. However, residual squamous cell carcinomas, whenever encountered together with glandular and spindle cell components, exhibited extensive degenerative changes and marked tumor necrosis.

To ascertain whether the reduction in tumor volume was a consequence of decreased proliferation or increased cell death, proliferation indices were determined, and as a measure of apoptosis, the expression of activated caspase-3 after only 3 days of PPP or PPP plus Erlotinib treatment, i.e. prior to a drastic decrease of the pale and squamous cell components was examined. It was observed that, while proliferation was still at control levels, the numbers of caspase-3-positive cells in the microacinar and non-glandular components were 2- and 9-fold higher, respectively, than in controls (FIG. 3C).

To evaluate IGF1R as a drug-target in human cells, the receptor in MDA-MB-231 mammary cancer cells, which possess a KrasG13D mutant gene (Kozma S C, et al., *Nucleic Acids Res*. (1987), 15:5963-5971; Hollestelle A, et al., *Mol Cancer Res*. (2007), 5:195-201) and share similarities in transcriptional profile with basal-like mammary tumor cell line (Charafe-Jauffret E, et al., *Oncogene* (2006), 25:2273-2284) was targeted. Pharmacological inhibition using PPP drastically reduced the in vitro viability of MDA-MB-231 cells (FIG. 8A). In addition, IGF1R knockdown using either a dominant-negative form of the receptor or siRNA had an analogous effect (FIGS. 8B and 8C). In a xenograft model in NOD/SCID mice, it showed that tumor growth from orthotopically injected MDA-MB-231 cells was also attenuated in PPP-treated mice in comparison with vehicle-treated controls (Table 6). Although the in vivo effect of PPP on the highly invasive MDA-MB-231 xenografts was overall less pronounced than that observed with the mouse carcinomas, it was statistically significant. In addition to other factors, such as poor vascularization making the drug less accessible, the behavior of these xenografts derived from MDA-MB-231 cells that are more spindly than epithelial may be analogous to the relatively reduced response of the SRC component of mouse Kras* tumors to PPP. Nevertheless, in conjunction with the mouse data, these observations provide strong justification for further evaluations of the drug against human breast cancer.

KRAS and Human Breast Cancer

Figure 5E:
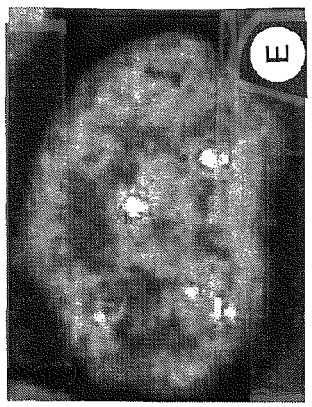
Figure 5F:
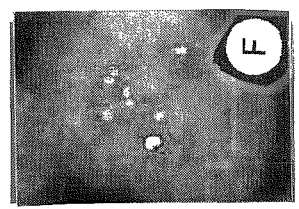
Figure 5G:

A comparison between the mouse mammary tumors induced by K-ras*activation and human breast cancer is shown in FIGS. 5A-5D. In a set of human breast cancer specimens collected in the period between 1994 and 2003, $17/94$ (18%) were found to be basal-like (triple-negative), while $77/94$ (82%) were non-basal. Analysis of the 17 basal cancers for KRAS amplification by using Southern blotting, CGH and FISH showed that 5 of the specimens (~29%) scored positive in at least two of these three assays (FIGS. 5E-5G show an example of the FISH results), whereas amplification of the locus (detected by CGH) was found in only 4 of the 77 non-basal samples (~5%; P=0.008, Fisher's exact test). All 5 basal-like specimens with amplified KRAS displayed medullary features, as they formed large tumor nodules with pushing, rather than infiltrative borders and were composed of large cells with irregular, sometimes bizarre nuclei growing in a syncytial fashion consistently lacking tubule formation. However, none of these carcinomas met all of the criteria for medullary carcinoma and, thus, they are referred to here as "atypical medullary breast cancer" (AMBC). Interestingly, $3/5$ AMBCs with KRAS amplification, which in addition to their syncytical/nodular growth pattern contained high numbers of large cells with pale or clear cytoplasm, exhibited a strong resemblance to the histomorphological signature of the pale cell carcinoma observed in our mouse model. To confirm the validity of this correlation, all of the available triple-negative ABMCs (n=9) collected between 2005 and 2007 were examined, and it was observed that most of them ($8/9$) were at least focally comparable to the PCC in Kras* mice. Immunohistochemical analysis showed that all 9 of these ABMCs were positive for basal cytokeratins 5 and 14 and showed IGF1R staining along their cellular surface. FISH analysis was then performed to assess potential amplification of the KRAS locus and found that 3 of these cancers, all of which possessed as a major component large pale cells, tested positive (P=0.02; using the data $3/5$ for basal and $4/77$ for non-basal specimens). These data indicate that a subset of basal-like human breast cancers exhibit preferentially amplification of the KRAS locus frequently associated with a pale cell carcinoma character.

8.3. Conclusion

It has been shown that overexpression of oncogenic Kras* in mouse mammary glands leads to rapid development of histopathologically heterogeneous malignant tumors predominantly simulating human basal-like breast cancers, but also including a luminal type. Although the incidence of KRAS mutations in human breast cancer is not very high, it is still appreciable (~7% in tumors and ~13% in cancer cell lines; see Hollestelle A, et al., *Mol. Cancer. Res*. (2007), 5:195-201; Malaney S and Daly R J, *J. Mammary Gland Biol. Neoplasia* (2001), 6:101-113). Moreover, in ~70% of primary breast cancers, the level of RAS is higher than that in normal tissue (Dati C, et al. *Int. J. Cancer* (1991). 47:833-838). Such elevated RAS activity is apparently required even for mammary carcinogenesis induced by RAS mutations (Sarkisian C J, et al. *Nat. Cell Biol*. (2007), 9:493-505). Clearly, regardless of cause (mutation and/or overexpression), the important element contributing to oncogenesis is the perturbation of the Ras pathway, which can be dissected genetically by mouse modeling. The diversity of cancerous forms and especially the rapidity of tumor manifestation increases further the utility of the mouse model that have been described here, which can be used advantageously after appropriate genetic testing for preclinical evaluation of treatment regimes, as exemplified by our results.

Seemingly, the single-step tumorigenesis that has been observed does not conform to the widely accepted multi-hit model of carcinogenesis (Vogelstein B and Kinzler K W, *Trends Genet*. (1993), 9:138-141; Hanahan D and Weinberg R A, *Cell* (2000), 100:57-70). However, from the standpoint that cancer is a disease of malfunctioning cell signaling, all cases of tumor development can be viewed, regardless of timing, as variants of a more general hypothesis positing that contributing "hits" correspond to recruitment and combinatorial engagement of deregulated pathways predominantly involved in apoptosis and growth control. Apparently, in the case of our model, highly overexpressed, constitutively active Kras* can elicit synergism of downstream pathways that are simultaneously deregulated to a degree sufficient for rapid development of invasive cancer. Analogous inverse reciprocity between Kras* expression levels and tumor latency in other mouse models has been observed other than the extremely rapid development of carcinomas of the skin and the oral mucosa induced by Kras* observed by others (Vitale-Cross L, et al, *Cancer Res.* (2004), 64:8804-8807). It remains to be seen whether, by exceeding normally affordable limits, oncogene overexpression overrides homeostatic capabilities and/or if the excessive deregulation that it causes permits novel and abnormal signaling interactions.

An additional open question is why the constitutively acting oncogenic Kras*, which has ceased to respond to upstream effectors in signaling relays and has presumably acquired autonomy in deregulating signaling, is not refractory to the silencing of Igf1r. Ras proteins control proliferation through the Raf→MEK→Erk pathway, but also interact directly with the p110 catalytic subunit of the PI3K complex, thus affecting anti-apoptosis. It is notable, in this regard, that loss-of-function missense mutations in the Ras binding domain of p110 inhibit almost completely Kras and Hras oncogenicity in mouse models of lung and skin tumors, respectively (Gupta S, et al. *Cell* (2007), 129:957-968). The mechanistic details in this case (involving a different tissue) are unclear. However, a testable hypothesis is that, without the crucial participation of Igf1r signaling that exerts both PI3K-dependent and PI3K-independent anti-apoptotic effects, the direct activation of the PI3K pathway by Kras* is, despite its overexpression, inadequate for attaining a level of anti-apoptosis able of promoting oncogenicity. It is noted that the results of a previous study (Cristofanelli et al. *Oncogene* (2000), 19:3245-3255) showing that 32D cells could become tumorigenic by the combined action of Hras and Irs1 (a downstream effector of Igf1r), but not by either one of these components acting alone, could also be interpreted as indicating a collaboration between the Erk and PI3K pathways. Perhaps, among other effects, Kras* triggers in this case the operation of a positive feedback loop that enhances its action through the upregulation of Igf1r expression which, in turn, could amplify proliferative and anti-apoptotic signaling by increasing the expression of Egf ligands. The downregulation of such ligands by genetic inactivation of Igf1r could explain why PPP is more effective than Erlotinib in the treatment of Kras*-induced tumors. Presumably, pharmacological inhibition of Egfr alone does not attenuate tumor growth sufficiently because the Egf ligands are still expressed at high levels and can function through other receptors of the family (the most likely candidates are Erbb2:Erbb3 heterodimers). In contrast, in addition to the direct pharmacological inhibition of Igf1r activity by PPP, there is an indirect effect on Egf ligand downregulation preventing the robust formation of homo or heterodimers between the Erbb receptor family members.

9. EXAMPLE 4

In Vivo Testing

Mice were generated that carried the Ef1/Kras* oncogenic mutation together with one or two alleles of the IGF1R locus conditionally knocked out (Xuan et al., *J. Clin. Invest.* 2002, 110, 1011-19) and the WAPcre transgene (which would activate the oncogene and ablate the IGF1R gene in the same cells during pregnancy/lactation). Parous mice were observed for the development of invasive tumors and compared the tumor latency with control females that carried only the oncogene and the WAPcre gene. In such mice, IGF1R inactivation has a profound effect on tumor latency, even in mice where only one of the two alleles is ablated.

To test the effect of IGF1RK inhibitors on tumor growth, parous Ef1/Kras*; WAPcre mice are monitored for tumor development every day upon parturition and examined with palpation for tumor development. Once tumors are readily palpable (1-2 mm diameter), the tumor size and body weight of the mice are documented. Mice are then treated with either vehicle or an IGF1RK inhibitor. Typically, mice are injected daily with 100-150 µl of a solution containing 90% DMSO and 10% of an emulsifier (Cremophor EL, Sigma). In this solution, for example, PPP is completely soluble at a concentration of 6 mg/ml.

After 21 days of treatment, the mice are sacrificed, weighed, and the initial tumors measured individually. In addition, tumors which were not palpable at the time of initial palpation, but had grown during the therapy period, are also isolated. In an experiment comparing vehicle treatment with PPP, the total tumor volume per mouse in the vehicle group was 653±219 mm$^3$ (number of mice: 7, total mammary gland affected: 21). Mice treated with PPP showed a much slower tumor growth with a total tumor volume per mouse of 54±28 mm$^3$ (p=0.05) at the end of the study.

10. EXAMPLE 5

10.1. Materials and Methods
Mice

Knock-in transgenic mice conditionally expressing oncogenic Kras were generated by standard procedures using targeted W9.5 ES cells. The targeting vector was prepared using the Eef1a1 cassette described in FIG. 1. The starting DNA to provide homology arms (5' 812 bp; 3' 3,606 bp) was a 4,418 bp SacII/NheI fragment containing the entire Eef1a1 locus except for the non-coding exon1. This fragment, isolated from a genomic library of mouse strain 129/Sv in phage λ (λFIX II vector; Stratagene), was modified by introducing into a unique SpeI site proximal to the end of intron1 a PacI/PmeI/AscI linker to facilitate cloning. A mouse Kras cDNA (referred to here as Kras*) containing a G→A nucleotide substitution in codon 12 (GGT→GAT) was excised from a plasmid (pBS.KS.G12D.Ras4B.pA; kindly provided by Drs. D. Tuveson and T. Jacks, Massachusetts Institute of Technology, Cambridge, Mass.) and subcloned into the pBigT vector (Srinivas S, et al., *BMC Dev. Biol.* (2001), 1: 4). A segment from this intermediate construct containing a splice acceptor site, a floxed Pgk-neo-triple poly(A) and the Kras* cDNA was excised as a PacI/AscI fragment and cloned into the corresponding sites of the PacI/PmeI/AscI linker described above.
Molecular Analysis Standard protocols were followed for Southern, Northern and Western analyses. The probes used were a 616 bp XbaI/SacII fragment immediately upstream from the 5' arm (Southern) and the Kras* cDNA described above (Northern). The anti-Kras-specific antibody used for Western analysis was sc-521 (Santa Cruz Biotechnology). To examine the effects of dominant-negative IGF1R, plasmid 486Stop (D'Ambrosio C, et al., *Cancer Res.* (1996), 56:4013-4020; kindly provided by Dr. R. Baserga, Thomas Jefferson University, Philadelphia) or control pcDNA3 plasmid were introduced into MDA-MB-231 cells grown in DMEM supplemented with 10% fetal bovine serum by using a nucleofector (Amaxa Biosystems). RNA interference experiments with MDA-MB-231 cells were performed as described (Rochester Mass., et al., *Cancer Gene Ther.* (2005), 12:90-100) using the siRNA duplex R4 [sense strand 5'CAAUGAGUACAACUAC-CGCTT3' (SEQ ID NO: 1); antisense strand 5'GCGGUAG-UUGUACUCAUUGTT3' (SEQ ID NO: 2)], which targets the human IGF1R mRNA at nucleotides 639-657, and a scrambled control duplex [Scr4; sense strand 5' GUCACAC- CGAUAAGUCACATT3' (SEQ ID NO: 3); antisense strand 5'UGUGACUUAUCGGUGUGACTT3' (SEQ ID NO: 4)].

Histological Analysis, Immunophenotyping, Flow Cytometry and FISH

Mouse tissues were fixed in 10% formalin, embedded in paraffin, sectioned, and stained with hematoxylin and eosin. The primary antibodies and the conditions used for immunohistochemistry are listed in Table 9. Semiquantitative scoring (− to +++) was according to the system used for HercepTest™ (Dako), with − representing no staining, + weak staining in >15% of the cells, ++ strong focal staining in <15-20% of the cells, and +++ strong staining in >15-20% of the cells. Immunofluorescence was performed on paraffin sections by standard procedures. For flow cytometry, single cell suspensions from mammary glands and tumors prepared as described (Stingl J, et al. *Nature* (2006), 439: 993-997) were processed using the EasySep kit (StemCell Technologies) and analyzed on a FACS Aria instrument (Becton Dickinson). For fluorescence in situ hybridization analysis we used three BAC clones (Invitrogen; RP11-157L06, RP11-583L24 and RP11-707G18) spanning the human chromosome 12p12.1 region containing the KRAS locus. BAC DNA was labeled by nick-translation using spectrum red dUTP fluorochrome (Abbott Molecular). A Spectrum green-labeled centromeric 12 (CEP 12) probe (Abbott Molecular) was used to enumerate chromosome 12. FISH was performed by standard methods and hybridization signals were scored on at least 100 interphase nuclei on DAPI-stained slides. The human breast cancer specimens analyzed histologically or by FISH were obtained from Surgical Pathology files of the College of Physicians, Columbia University, following approval of the Institutional Review Board.

Microarray Analysis

For expression profiling, total RNA was extracted from mammary tumors of Kras*/WAP-cre bitransgenic or age-matched postinvolutional female mice. The samples were profiled individually. For each assay, 5-8 µg of total RNA were used to generate biotinylated cRNA that was fragmented (15 µg) and then hybridized to Mouse Genome 430 2.0 Array DNA Chips (Affymetrix). The microarrays were scanned (Affymetrix Scanner) and expression values for the genes were determined using Affymetrix GeneChip Operating Software 1.2. Filtering and further analysis using the raw data was performed with GeneSpring 6.0 software. A ratio of ≥2 (experimental/control for "upregulated and control/experimental for "downregulated" entries) was used as a widely accepted cut-off point indicative of a significant difference in transcript levels. An unsupervised clustering dendrogram was generated by using Cygwin software. Literature data compared with our results (see Table 5) were filtered to select and use only markers represented in the Affymetrix 430 2.0 chip, which also corresponded to known genes (unknown ESTs were ignored) and were at least 2-fold upregulated or downregulated in comparison with corresponding controls. For comparative identification of signaling molecules (see Tables 6 and Table 7), key-members of all major signaling pathways were listed in Table 8) and they were selected in a non-redundant fashion from the following databases: KEGG (www.genome.ad.jp/kegg/kegg2.html), BioCarta (cgap.nci.nih.gov/Pathways/BioCarta_Pathways), Cancer Cell Map (cancer.cellmap.org/cellmap), Pathway-Express (vortex.cs.wayne.edu/ontoexpress) and Wikipathways (www.wikipathways.org).

Statistical Analysis

Values were expressed as mean±S.E.M. Results were considered as statistically significant if P<0.05. For analysis of survival curves, a log-rank test was used. Differences between groups were examined using Student's t test. The null hypothesis that there is no marker difference in pairwise comparisons between microarray datasets was evaluated using Fisher's exact test.

10.2. Results and Discussion

Example 3 has shown that the Kras*-induced murine mammary carcinomas are histopathologically heterogeneous and include, in addition to three basal-like components, a luminal type. On the basis of morphological and molecular criteria, an advanced hypothesis is that the cells-of-origin of the basal-like carcinomas are epithelial progenitors. This is consistent with observations indicating that populations of flow-sorted $CD24^+/CD29^{hi}$ or $CD24^+/CD49f^{hi}$ cells (depleted of hematopoietic contaminants; Lin−), which were enriched in mammary gland-forming stem cells defined operationally by cleared fat pad transplantation assays (Shackleton M, et al., *Nature* (2006), 439:84-88; Stingl J, et al., *Nature* (2006), 439: 993-997), exhibit phenotypic similarities with basal-like tumors (Asselin-Labat M L, et al., *J. Natl. Cancer Inst.* (2006), 98:1011-1014). Interestingly, comparative FACS analysis of cell suspensions isolated from Kras*-induced tumors (n=3) and normal mammary glands of age-matched parous females (n=5) showed an increase in the number of $CD24^+/CD49f^{hi}$ neoplastic cells (FIG. 9); the distribution of the markers CD49f (Itga6; integrin α6) and CD29 (Itgb1; integrin β1) in Kras* tumors is shown in FIG. 10). An additional interesting marker present in PCC and SCC, but not in SRC or Dunn tumors, was Sca1 (FIG. 6 and Table 4). Although $CD24^+/CD49f^{hi}$ cells express high levels of Sca1 only after culturing (Vaillant F, et al., *Stem Cell Rev.* (2007), 3:114-123), this marker still belongs to a stem cell signature, considering that cultured mammary epithelial cells with this phenotype are able to repopulate cleared fat pads (Welm B E, et al., *Dev. Biol.* (2002), 245:42-56). Nevertheless, the observations are not sufficient to identify exact cell types and their hierarchical standing in the cell lineage of the presumptive precursors, despite some clues. For example, Gata3, a marker of mature luminal epithelium also expressed in precursor cells of mammary primordia (Asselin-Labat M L, et al. *Nat. Cell Biol.* (2007), 9:201-209), is present in PCC but not in SCC (FIG. 6 and Table 4). This difference may be indicative of distinct cells-of-origin, also suggested by the identification of distinct CISs. Differences in the expression of particular markers, such as CK5/14 and p63, also exist between SRC and the other two basal-like components (PCC and SCC). It is noted that the SRC, despite loss of E-cadherin (epithelial marker) and strong expression of vimentin (mesenchymal cell marker; see FIG. 6), are presumably epithelial and not mesenchymal tumors that could be derived from an adenosquamous component by epithelial-mesenchymal transition (Cardiff R D, et al., *The Mouse in Biomedical Research.* (2007), *Volume II. Diseases, Second ed.*, eds. Fox J G et al., (Elsevier, New York), pp. 581-622).

Since the exact stages in the developmental progression from stem cells to differentiated luminal and myoepithelial cells remain largely undefined, a likely scenario accounting for the Kras* tumor heterogeneity in conjunction with the hypothesis described above, is parallel transformation of three different cell types. There are three reasons for such a scenario. First, the originator of the Dunn A/B tumors is a fully committed luminal-type cell that can still respond to oncogenic stimuli without becoming apoptotic. Second, the Wap gene, and therefore cre, is expressed in bipotent alveolar progenitor cells of virgin and parous mice (Booth B W, et al., *J Cell Physiol.* (2007), 212:729-736; Matulka L A, et al., *Dev. Biol.* (2007), 303:29-44), and also that a significant expansion of the $Cd24^+/Cd49^{high}$ compartment containing mammary bipotent progenitors/stem cells (Shackleton M, et al., *Nature* (2006), 439:84-88) occurs in Kras* mice, it is speculated that the squamous cell carcinoma probably originates from such cell precursors. Squamous metaplasia has been widely reported in mouse models of breast cancer, including MMTV-Wnt mice, in which progenitor cells are thought to be the target of oncogenic transformation (Li Y, et al., *Proc. Natl. Acad. Sci. USA* (2003), 100:15853-15858). In the context of this scheme, to account for Gata3 expression and the presence of a distinct CIS, it is proposed that a third cellof-origin, also bearing the CD24 and CD49f markers, gives rise to pale cell carcinoma.

11. EXAMPLE 6

Efficacy of Compounds 18 and 21 to Ameliorate Kras*-induced Mammary Carcinomas The efficacy of compounds 18 "(NB3)" and 21 "(NB6)" to ameliorate Kras*-induced mouse mammary carcinomas was tested. While testing NB3 and NB6 (4 mice each), 2 controls were added (2 tumor-bearing mice treated with vehicle). The control data were pooled with the previous, and the new results are listed in Table 10:

TABLE 10

| Mouse Tumors | Drug treatments | | | | |
| --- | --- | --- | --- | --- | --- |
| | Mice (n) | Glands (n) | Tumor volume per gland (mm$^3$)[a] | % | P[b] |
| Vehicle | 9 | 29 | 243.3 ± 68.9 | 100 | |
| NB3 | 4 | 15 | 20.9 ± 10.8 | 6.5 | <0.0001 |
| NB6 | 4 | 13 | 2.1 ± 1.0 | 0.9 | <0.0001 |

[a]Mean ± S.E.M.
[b]Because of data skewness, in tumor volume comparisons between the drug treatments and the control (vehicle), probabilities (P) were calculated using Student's t-test after logarithmic transformation of the values to meet the distribution criterion of the test.

If, on the basis of the new control data, the previous "% tumor volume in comparison with the control" for PPP (7.3%) is normalized, it becomes 6.5%, i.e. NB3 has the same potency as PPP. Importantly, however, NB6 (compound 21) appears to be 7 times more potent.

While the invention has been described with respect to specific examples including presently preferred modes of carrying out the invention, those skilled in the art will appreciate that there are numerous variations and permutations of the above described systems and techniques that fall within the spirit and scope of the invention.

Various publications are cited above, the contents of which are hereby incorporated by reference in their entireties.

We claim:

1. A compound of formula I:

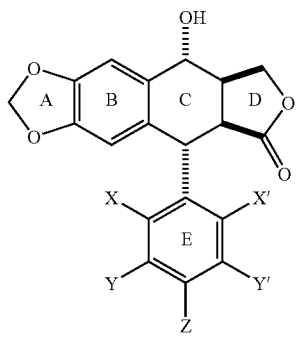

I wherein X, X', Y, Y' and Z are independently hydrogen, a $C_1$-$C_8$ alkyl, or $C_1$-$C_8$ alkoxy group with the proviso that when X and X' are H, Y, Y', and Z cannot all be $OCH_3$.

2. The compound of claim 1 wherein X, X', Y, Y' and Z are hydrogen, methyl, or methoxy.

3. The compound of claim 1 wherein

X, X', Y, Y'=H, and Z=$OCH_3$;

X, X', Y', Z=H, and Y=$OCH_3$;

X, X', Y'=H, and Y, Z=$OCH_3$;

X, X', Z=H, and Y, Y'=$OCH_3$; or

X, X', Y, Y'=H, and Z=$CH_3$.

4. A compound selected from the group consisting of:

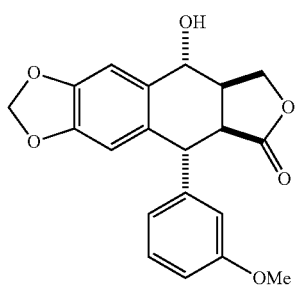

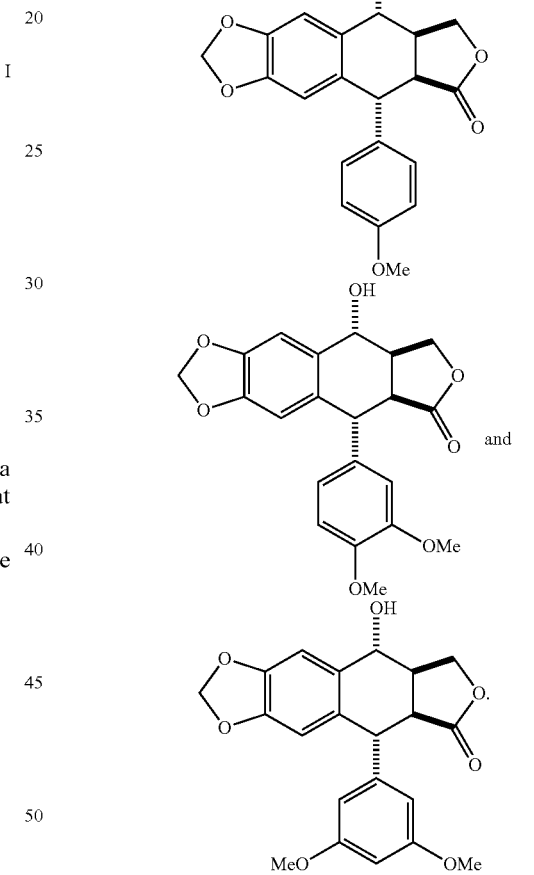

and

5. The compound of claim 1 wherein the $C_1$-$C_8$ alkoxy is a $C_1$-$C_4$ alkoxy.

6. A pharmaceutical composition comprising a compound of claim 1 and a pharmaceutically acceptable carrier thereof.

7. A pharmaceutical composition comprising a compound of claim 2 and a pharmaceutically acceptable carrier thereof.

8. A pharmaceutical composition comprising a compound of claim 3 and a pharmaceutically acceptable carrier thereof.

9. A pharmaceutical composition comprising a compound of claim 4 and a pharmaceutically acceptable carrier thereof.

10. A pharmaceutical composition comprising a compound of claim 5 and a pharmaceutically acceptable carrier thereof.

* * * * *